(12) United States Patent
Cheng et al.

(10) Patent No.: US 11,839,639 B2
(45) Date of Patent: Dec. 12, 2023

(54) INHIBITION OF ANDROGEN RECEPTOR BY EXTRACTS OF MEDICINAL HERBS AND COMPOSITIONS THEREOF

(71) Applicant: YALE UNIVERSITY, New Haven, CT (US)

(72) Inventors: Yung-Chi Cheng, Woodbridge, CT (US); Wing Lam, New Haven, CT (US); Zaoli Jiang, Woodbridge, CT (US)

(73) Assignee: YALE UNIVERSITY, New Haven, CT (US)

( * ) Notice: Subject to any disclaimer, the term of this patent is extended or adjusted under 35 U.S.C. 154(b) by 0 days.

(21) Appl. No.: 16/754,610

(22) PCT Filed: Oct. 18, 2018

(86) PCT No.: PCT/IB2018/001296
§ 371 (c)(1),
(2) Date: Apr. 8, 2020

(87) PCT Pub. No.: WO2019/077407
PCT Pub. Date: Apr. 25, 2019

(65) Prior Publication Data
US 2020/0376067 A1    Dec. 3, 2020

Related U.S. Application Data

(60) Provisional application No. 62/574,440, filed on Oct. 19, 2017.

(51) Int. Cl.
| | | |
|---|---|---|
| *A61K 36/82* | (2006.01) | |
| *A23L 33/105* | (2016.01) | |
| *A61K 36/24* | (2006.01) | |
| *A61K 36/28* | (2006.01) | |
| *A61K 36/47* | (2006.01) | |
| *A61K 36/59* | (2006.01) | |
| *A61K 36/708* | (2006.01) | |
| *A61K 36/73* | (2006.01) | |
| *A61K 36/756* | (2006.01) | |
| *A61K 36/886* | (2006.01) | |
| *A61K 9/00* | (2006.01) | |
| *A61K 45/06* | (2006.01) | |

(52) U.S. Cl.
CPC ........... *A61K 36/82* (2013.01); *A23L 33/105* (2016.08); *A61K 36/24* (2013.01); *A61K 36/28* (2013.01); *A61K 36/47* (2013.01); *A61K 36/59* (2013.01); *A61K 36/708* (2013.01); *A61K 36/73* (2013.01); *A61K 36/756* (2013.01); *A61K 36/886* (2013.01); *A61K 9/0014* (2013.01); *A61K 9/0053* (2013.01); *A61K 45/06* (2013.01); *A61K 2236/331* (2013.01); *A61K 2236/333* (2013.01)

(58) Field of Classification Search
None
See application file for complete search history.

(56) References Cited

U.S. PATENT DOCUMENTS 6,790,464 B2 *   9/2004   Kuok ................... A61K 36/71
                                                    424/773
2003/0171334 A1   9/2003   Aylard et al.
(Continued)

FOREIGN PATENT DOCUMENTS

BR   PI0803136 A2   3/2010
CN   1660306 A     8/2005
(Continued)

OTHER PUBLICATIONS

"PSA Screening" https://zerocancer.org/learn/about-prostate-cancer/detection-diagnosis/psa-test/—accessed Sep. 2021.*
"Basic Tools of Herbalism" (http://web.archive.org/web/20041211085720/http://earthnotes.tripod.com/basics.htm—web archived version from Dec. 11, 2004).*
Merseburger (Adv Ther (May 2016), vol. 33, pp. 1072-1093).*
Shamaan NA, et al. Vitamin C and Aloe Vera Supplementation Protects From Chemical Hepatocarcinogenes in the Rat. Nutrition, 1998;14(11/12):846-852.
Haiden L; et al. Aloe-emodin suppresses prostate cancer by targeting the mTOR complex 2. Carcinogenesis, 2012;33(7):1406-1411.
Vardy DA; et al. A double-blind, placebo-controlled trial of an Aloe vera (*A. barbadensis*) emulsion in the treatment of seborrheic dermatitis. Journal of Dermatological Treatment, 1999; 10:7-11.
(Continued)

*Primary Examiner* — Susan Hoffman
(74) *Attorney, Agent, or Firm* — Henry D. Coleman; R. Neil Sudol

(57) ABSTRACT

In one embodiment, the present invention is directed to a composition comprising an aqueous or ethanolic extract of at least one herb selected from the group consisting of *Aloe barbadensis* (蘆薈:F3), *Rheum palmatum* L. (大黄:B6), *Stephania tetrandra* (汉防己:C4), *Phellodendron chinense* Schneid. (黄柏:D8), *Euphorbia humifusa* (地錦草:S6), *Eclipta prostrata* (墨旱蓮:I2), *A. venetum* L. (羅布麻:F1), *Portulaca oleracea* L. (马齿苋:F5), and *Sanguisorba officinalis* L. (地榆:E5), *Camellia sinensis* var. *assamica* (Mast.) Kitamura (普洱:PE) and *Punica granatum*. (石榴:PG), and mixtures thereof. The composition is administered to a patient, in an effective amount, in a method of treating, inhibiting, preventing, reducing the incidence of, ameliorating or resolving a disease state or condition caused in part or exacerbated by hyperactivity of the androgen receptor (AR), by inhibiting the androgen receptor protein. These compositions may also be used inhibit or stabilize hair loss or grow hair in a subject in need.

25 Claims, 38 Drawing Sheets

Specification includes a Sequence Listing.

(56) References Cited

U.S. PATENT DOCUMENTS

| | | | |
|---|---|---|---|
| 2008/0194675 A1 | 8/2008 | Bettuzzi et al. | |
| 2008/0274213 A1 | 11/2008 | Sekita et al. | |
| 2010/0285110 A1 | 11/2010 | Cid Vivanco et al. | |
| 2010/0291249 A1* | 11/2010 | Klein | A61P 17/00 424/776 |
| 2014/0045928 A1* | 2/2014 | Walters | A61P 31/12 514/456 |

FOREIGN PATENT DOCUMENTS

| | | | |
|---|---|---|---|
| CN | 103169632 A | 6/2013 | |
| CN | 104257800 A | 1/2015 | |
| CN | 105233258 A | 1/2016 | |
| JP | 2004168769 A | 6/2004 | |
| JP | 2007197387 A | 8/2007 | |
| KR | 20050079377 A | 8/2005 | |
| KR | 100572003 B1 | 7/2006 | |
| KR | 1 2015010897 2 A * | 10/2015 | |
| KR | 20160116721 A | 10/2016 | |
| WO | WO 01/22934 A2 | 4/2001 | |
| WO | 2011089602 A2 | 7/2011 | |
| WO | 2011089602 A3 | 7/2011 | |
| WO | WO 2012/122295 A2 | 9/2012 | |
| WO | WO-2013037843 A1 * | 3/2013 | A61K 36/27 |
| WO | 2014041542 A2 | 3/2014 | |
| WO | 2014052225 A1 | 4/2014 | |
| WO | 2016021872 A1 | 2/2016 | |

OTHER PUBLICATIONS

Maharjan R; et al. Effect of Aloe barbadensis Mill. formulation on Letrozole induced polycystic ovarian syndrome rat model. Journal of Ayurveda & Integrative Medicine, 2010; 1(4):273-279.

Cha TL, et al. Emodin Down-regulates Androgen Receptor and Inhibits Prostate Cancer Cell Growth. Cancer Res, 2005;65(6):2287-95.

Jain HC, et al. Sialic Acid Depletion Test for the Possible Androgenic-Antiandrogenic Effects of Aloe-Barbadensis 50 Percent Ethanol Extract in Male Dogs Canis-Indicus. Biosciences Information Service, Philadelphia, PA. 1986: Abstract.

Database GNPD [Online], Mintel. anonymous: Active Clear Acne Clearing Cleanser, 2016. Database accession No. 4434337.

Tetsuo Maeda, et al. Sanguisorba Officinalis Root Extract Has FGF-5 Inhibitory Activity and Reduces Hair Loss by Causing Prolongation of the Anagen Period. Nishinihon Journal of Dermatology, 2007;69(1):81-86.

CN 106176787 A; Use of chemical components of Herba Ecliptae to phytoestrogens; Abstract; Jul. 12, 2016.

CN 105267078; A Rheum officinale emulsion having function of preventing and treating freckles and acnes in skin; Abstract; Jan. 27, 2016.

CN101259166 A; Use of stephania tetrandra extract in preparing anti-tumor medicaments; Abstract; Sep. 10, 2008.

CN 103356515 A; Use of emodin anthraquinone derivative in preparation of anti-hepatocellular carcinoma drugs; Abstract; Oct. 23, 2013.

TW 201143776 A1; Compositions and methods of aloe polysaccharides ; Dec. 16, 2011; Abstract, p. 4-5 of instruction manual.

* cited by examiner

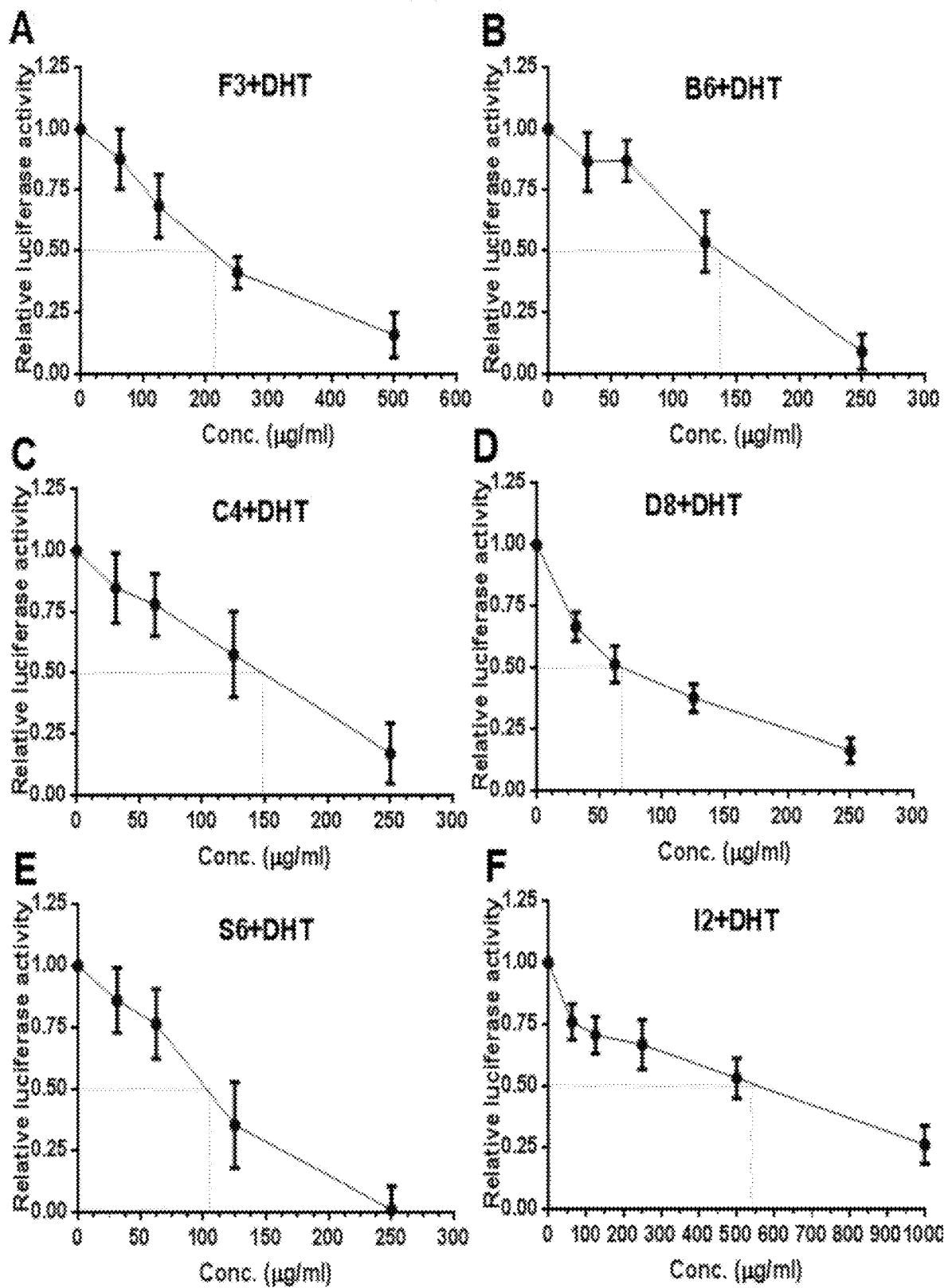
FIGURES 1A-I

FIGURES 1A-I (Cont'd)
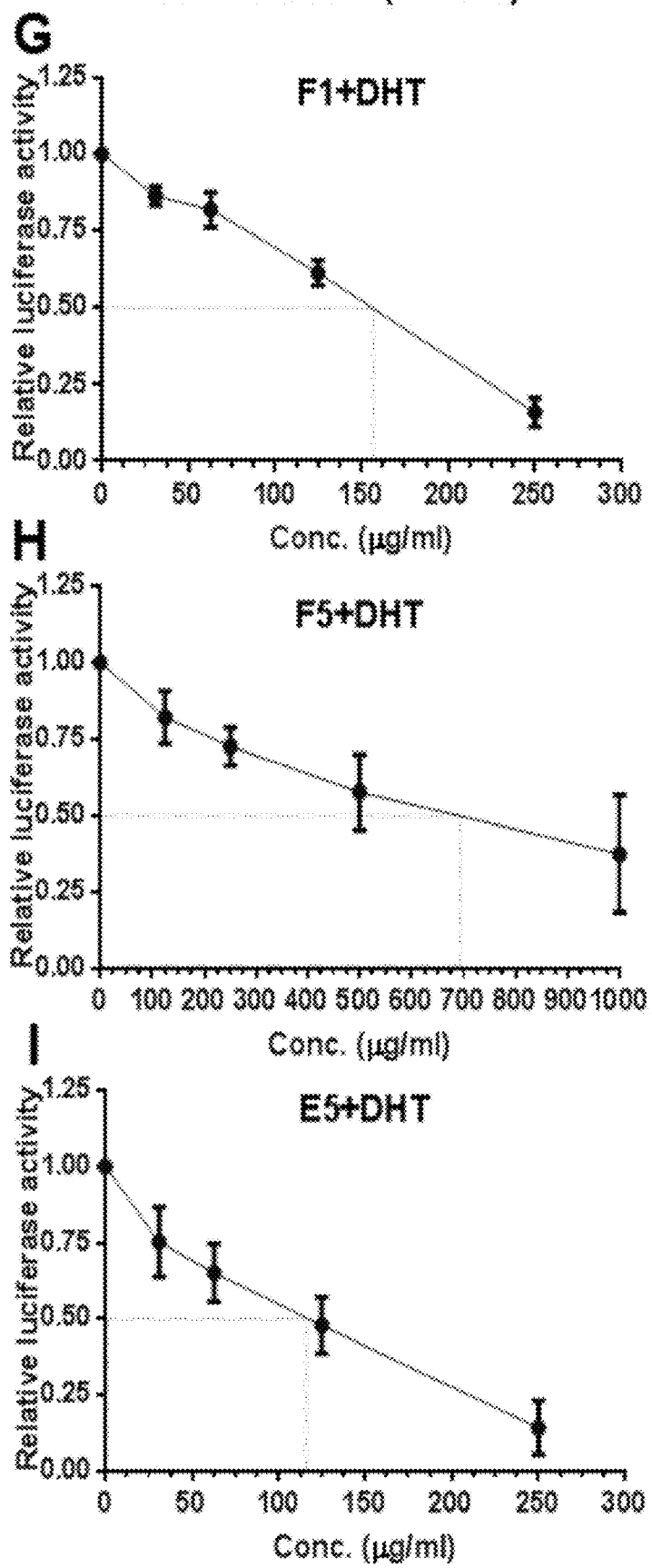

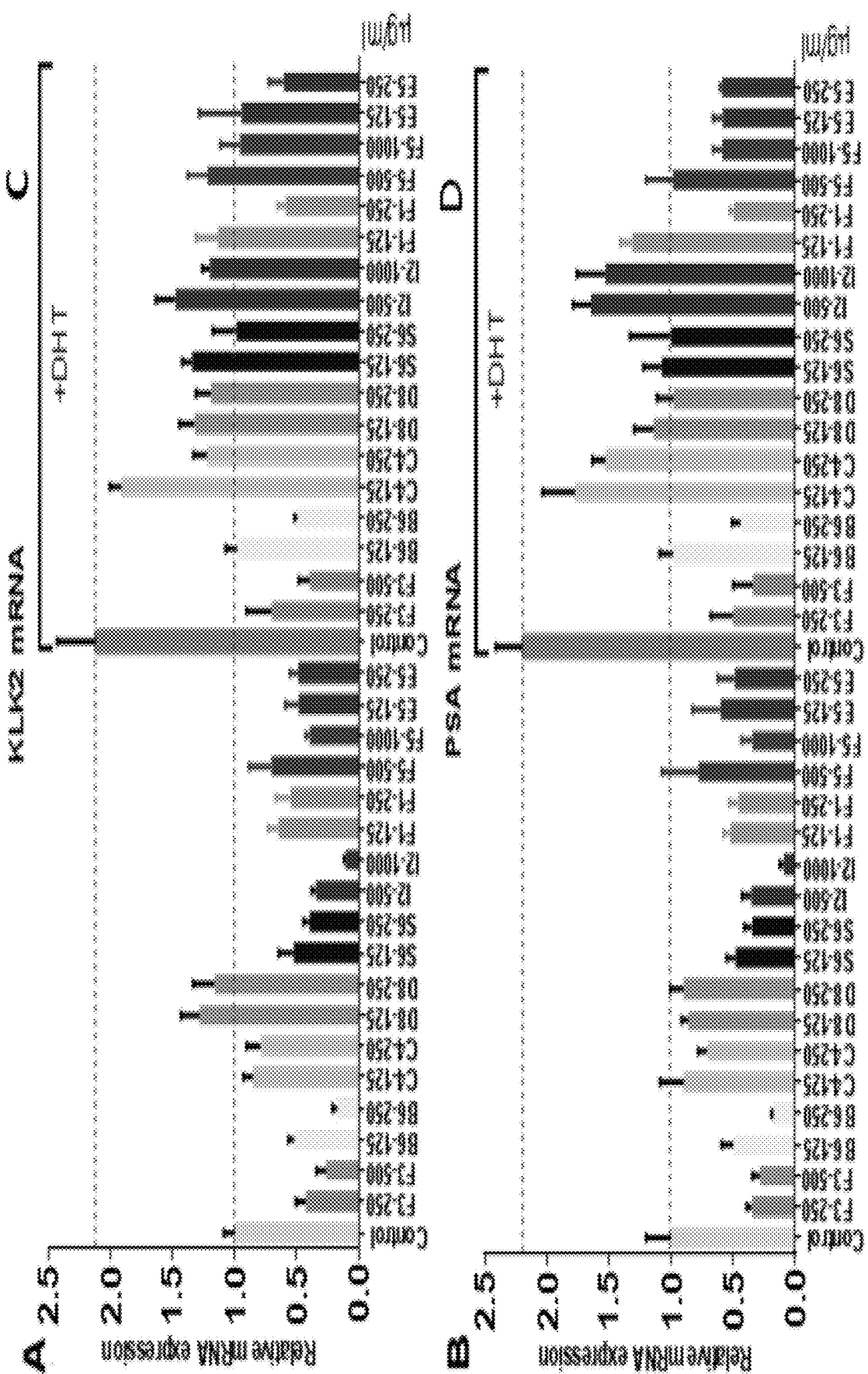
FIGURES 3A-F

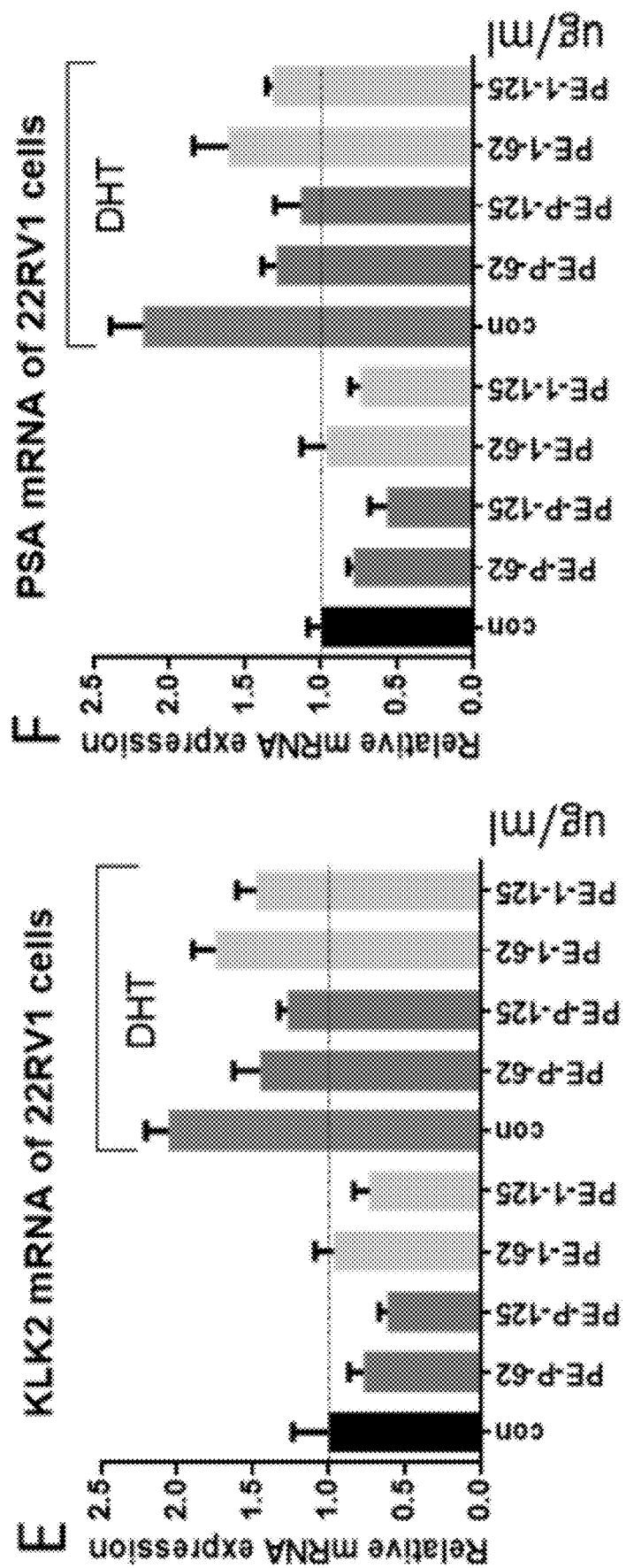
FIGURE 3A-F (Cont'd)

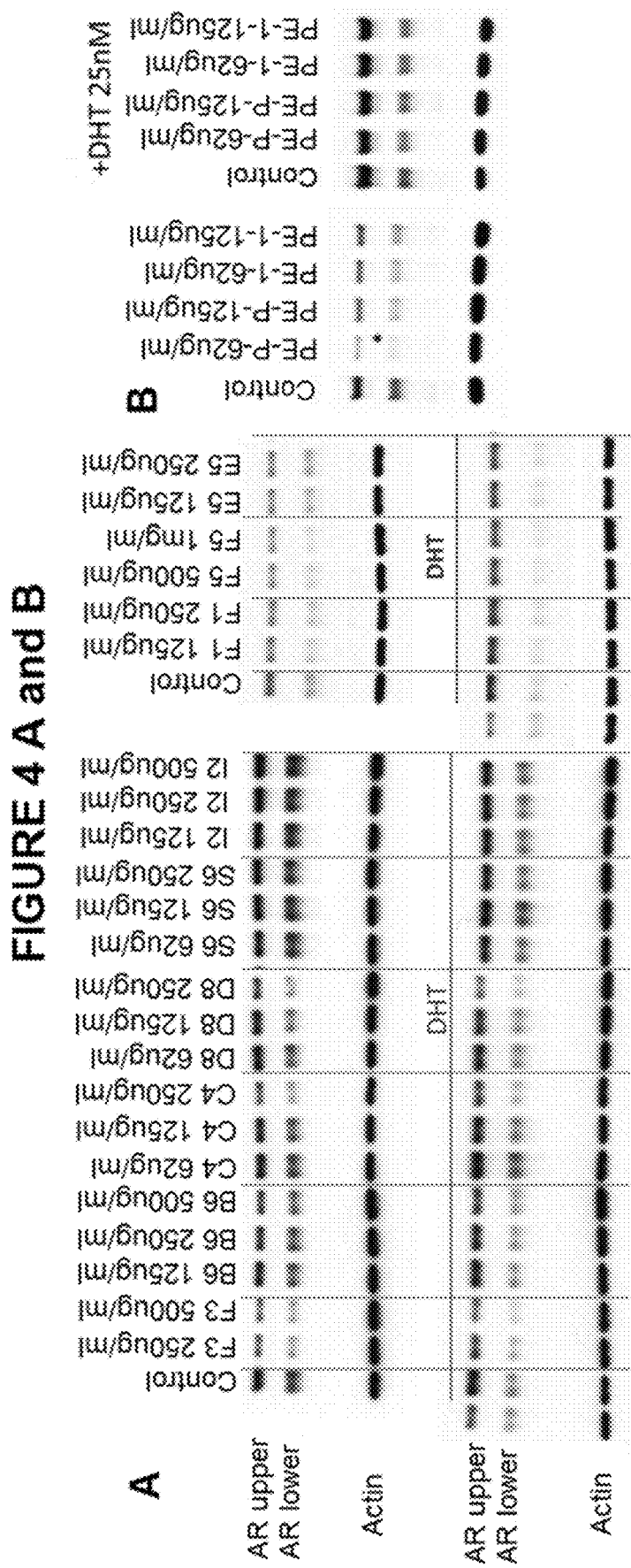
FIGURE 4 A and B

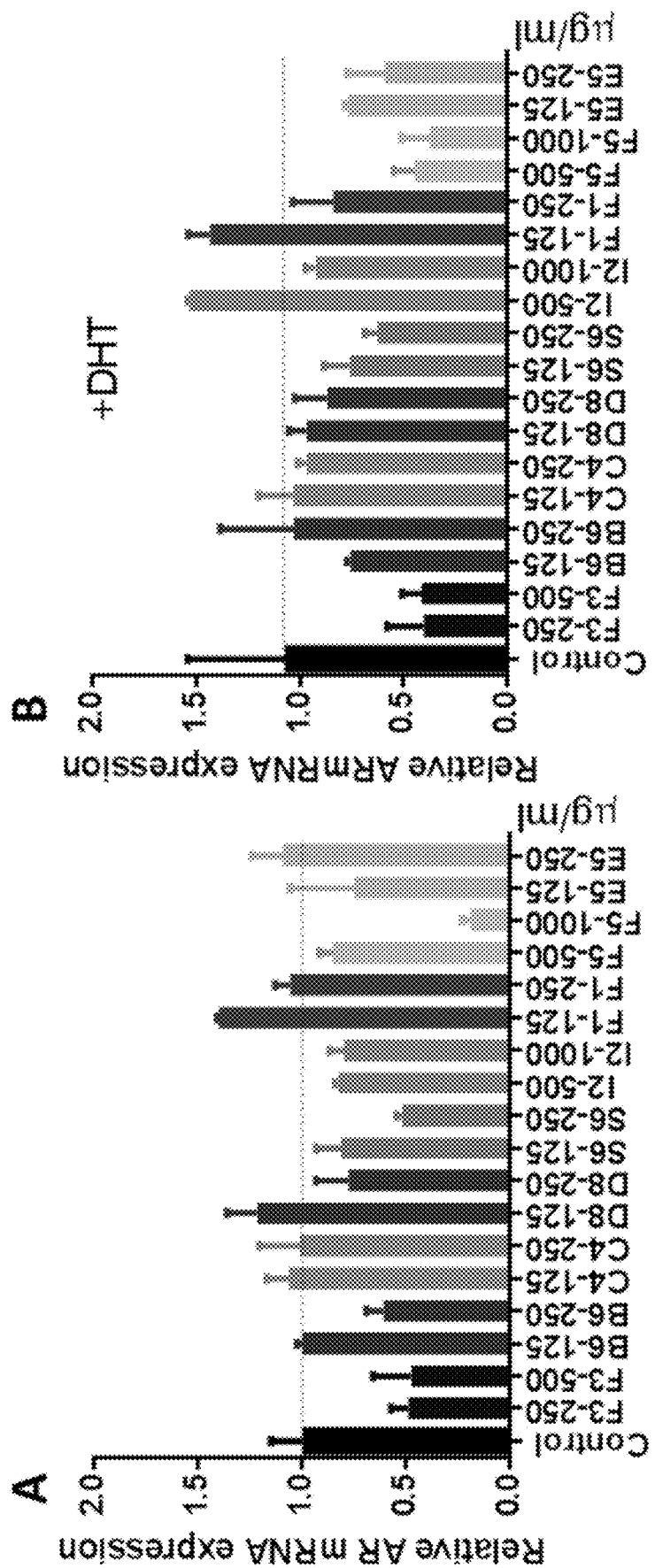
FIGURE 5A-C

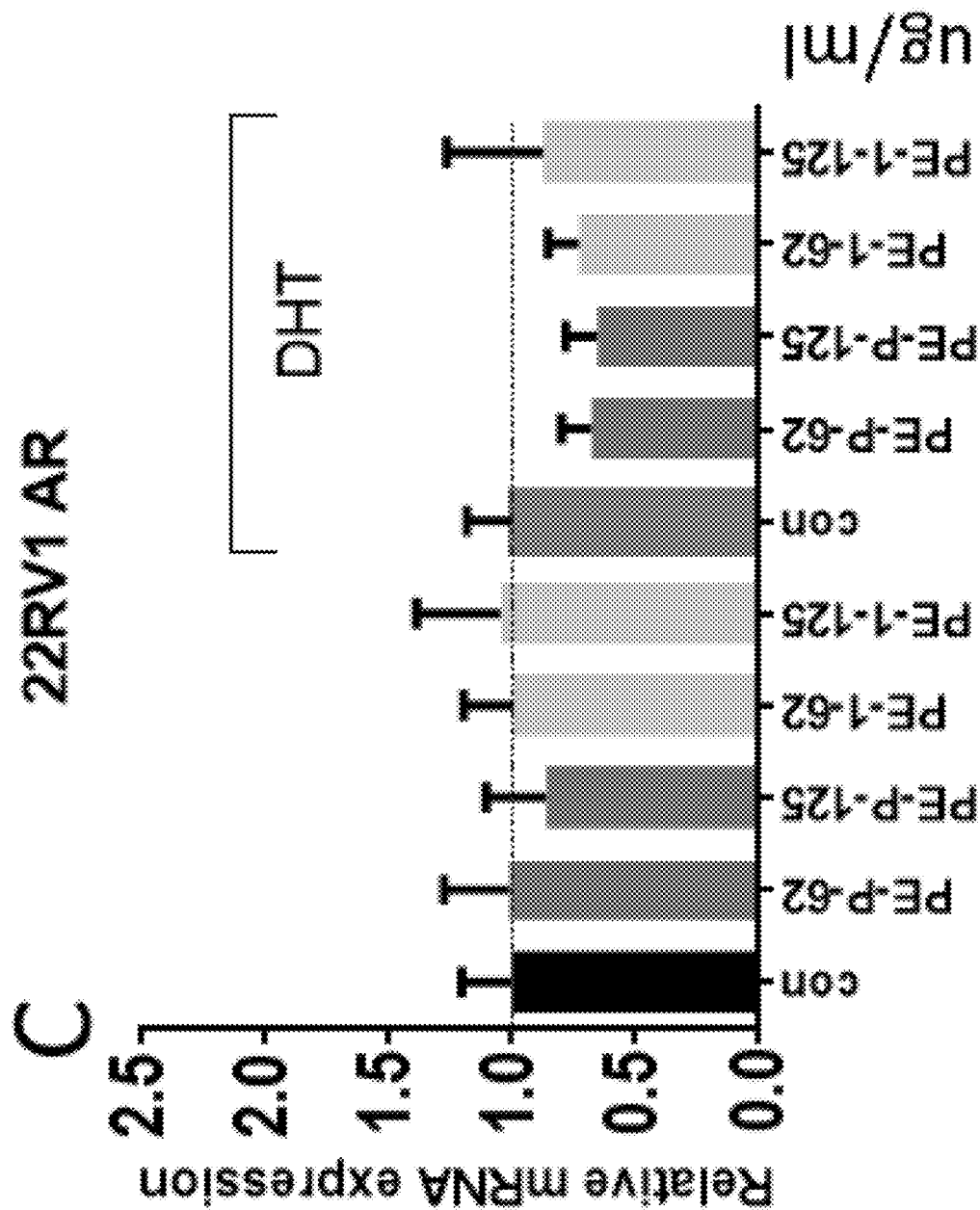

FIGURES 6A and B

A

Table 1.

|  | Down regulation on AR Protein | Down regulation on AR mRNA | Direct action on AR |
|---|---|---|---|
| F3 | + | + | - |
| B6 | + | - | ND |
| C4 | + | - | - |
| D8 | + | - | ND |
| S6 | - | - | + |
| I2 | - | - | + |
| F1 | - | - | + |
| F5 | + | + | + |
| E5 | - | - | + |
| PE1 | - | - | + |
| PG | + | + | ND |

B

| cell lines | 22RV1+DHT | Du145+DHT |
|---|---|---|
| Herbs | IC$_{50}$, µg/ml | IC$_{50}$, µg/ml |
| F3 | 242 | 397 |
| B6 | 93 | 123 |
| C4 | 70 | 112 |
| D8 | 125 | 25 |
| S6 | 35 | 70 |
| I2 | 315 | 415 |
| F1 | 128 | 142 |
| F5 | >1000 | >1000 |
| E5 | 90 | 48 |
| PE1 tea | 90 | 95 |

FIGURE 7A-L

FIGURE 11
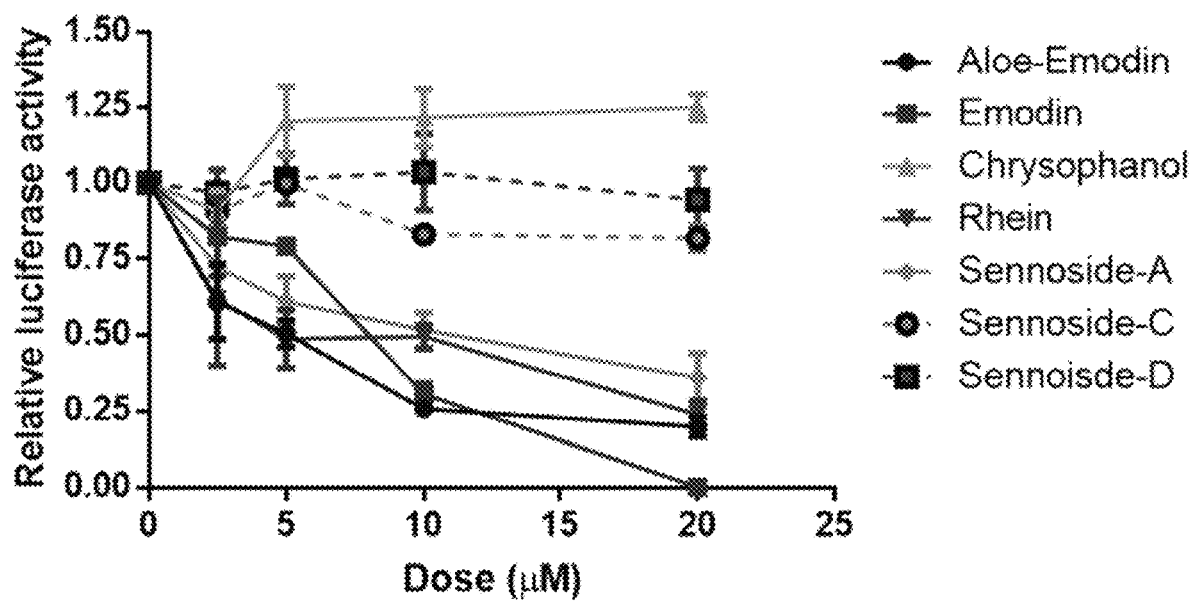
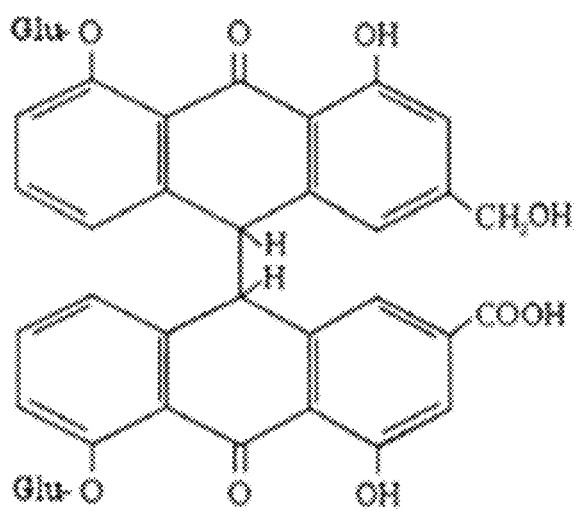
Sennoside A

FIGURE 11 (Cont'd)
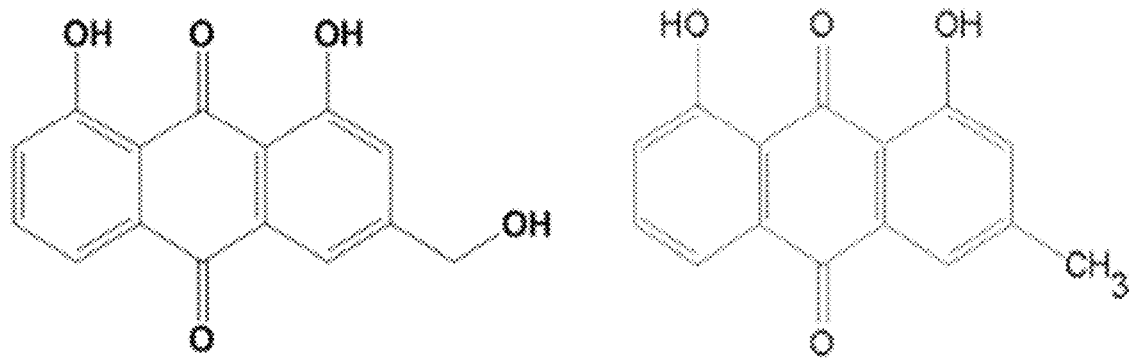
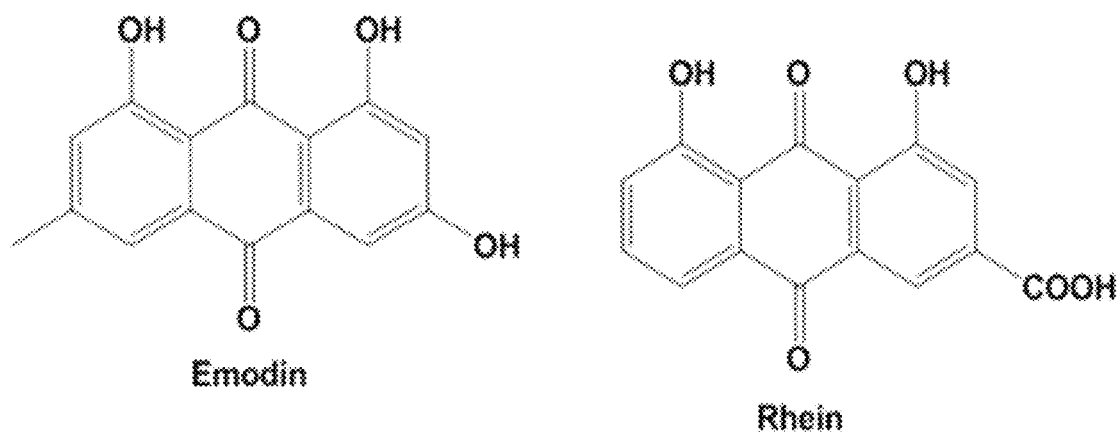
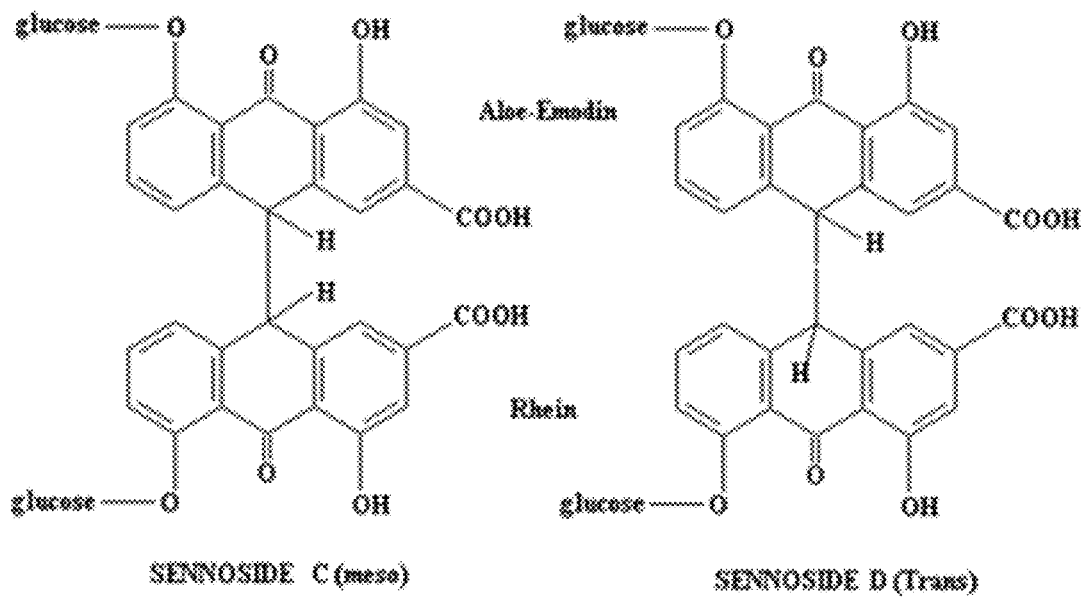

FIGURES 13A-F
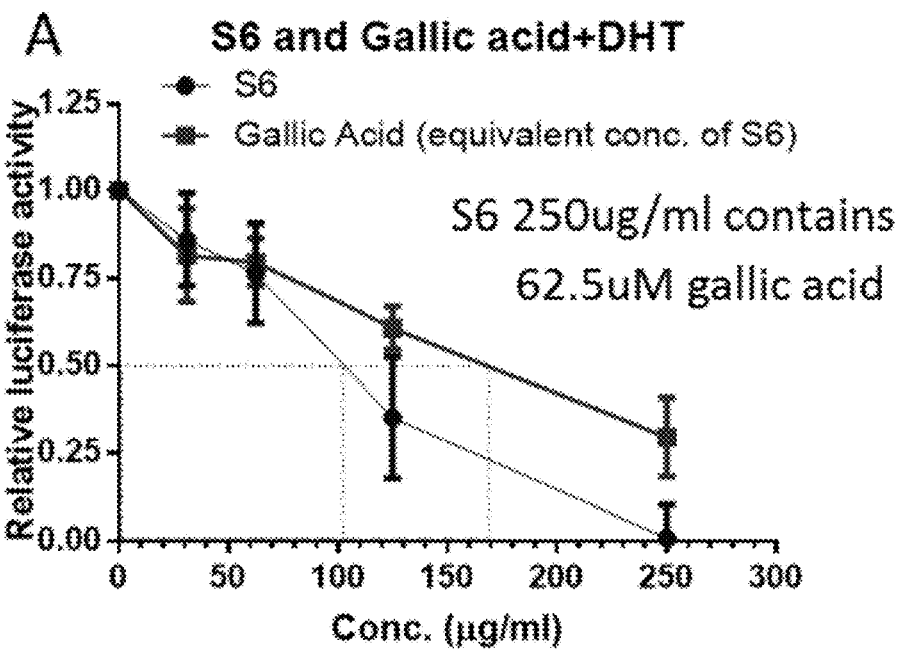
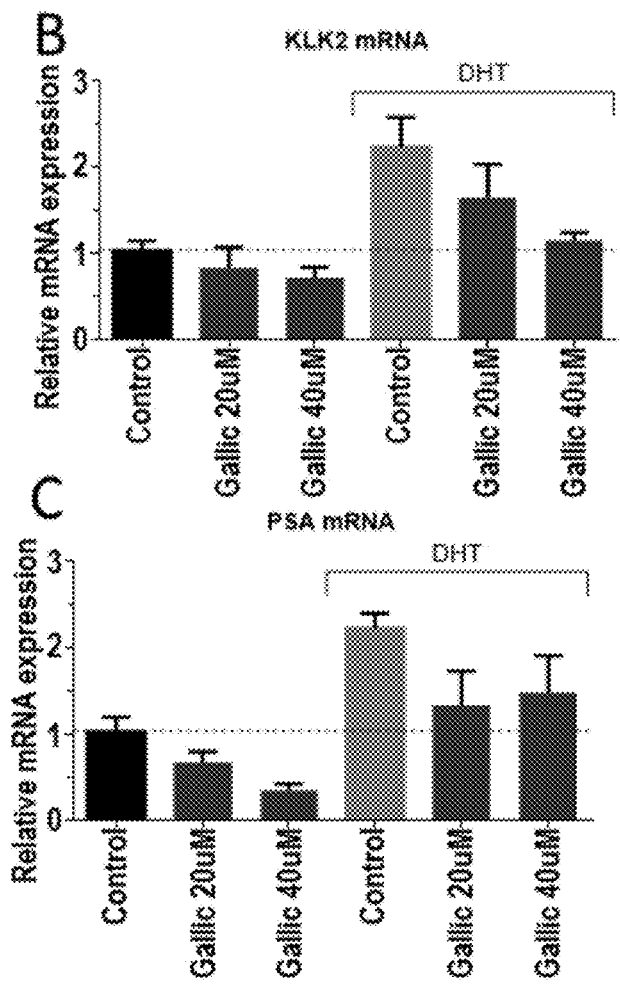

FIGURES 13A-F (Cont'd)
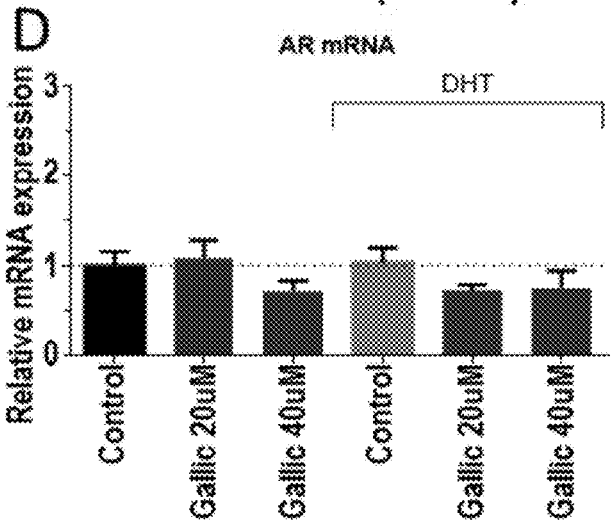
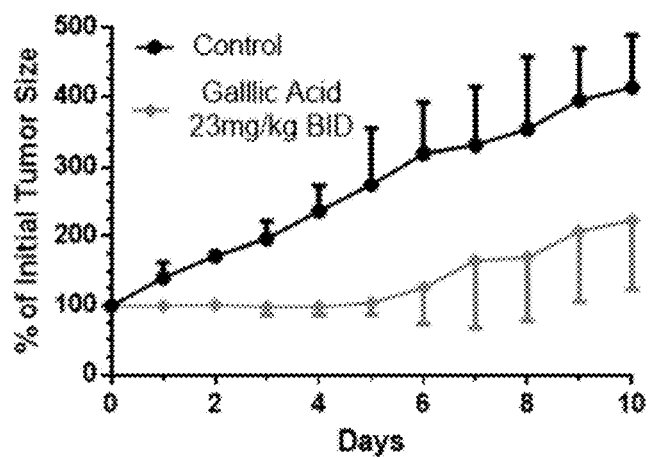
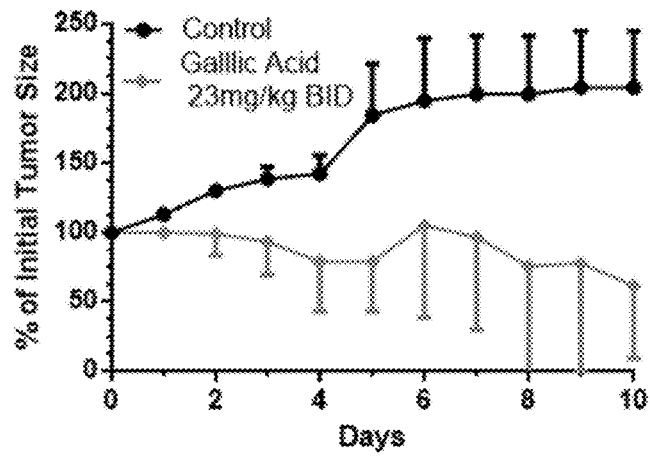

FIGURES 14A-C
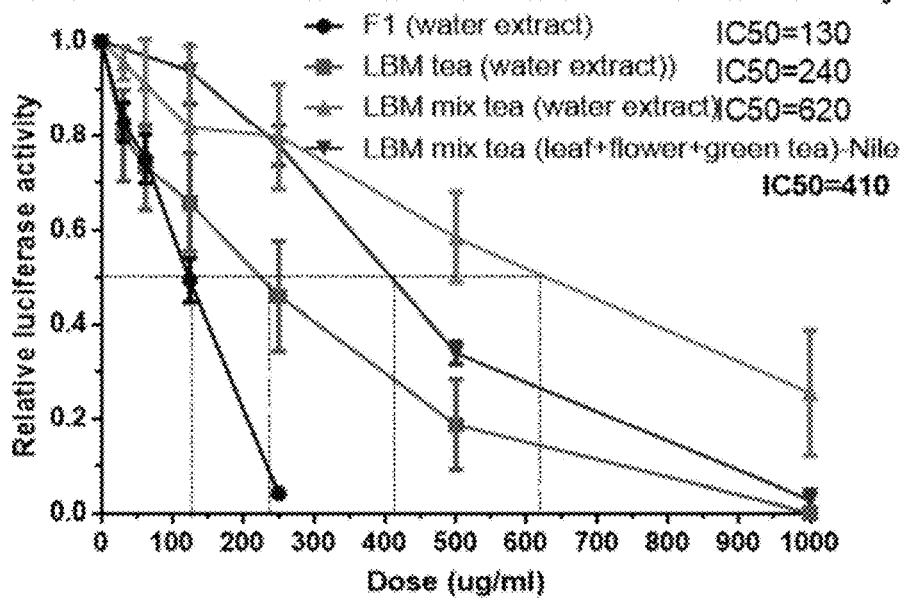
A. Effect of water extract on AR driven luciferase activity
- F1 (water extract) IC50=130
- LBM tea (water extract) IC50=240
- LBM mix tea (water extract) IC50=620
- LBM mix tea (leaf+flower+green tea)-Nile IC50=410
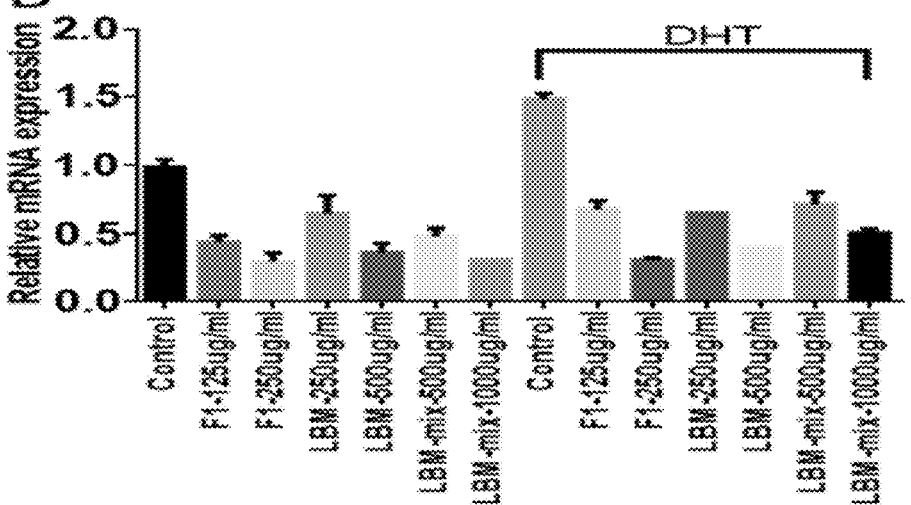
B. KLK2 mRNA
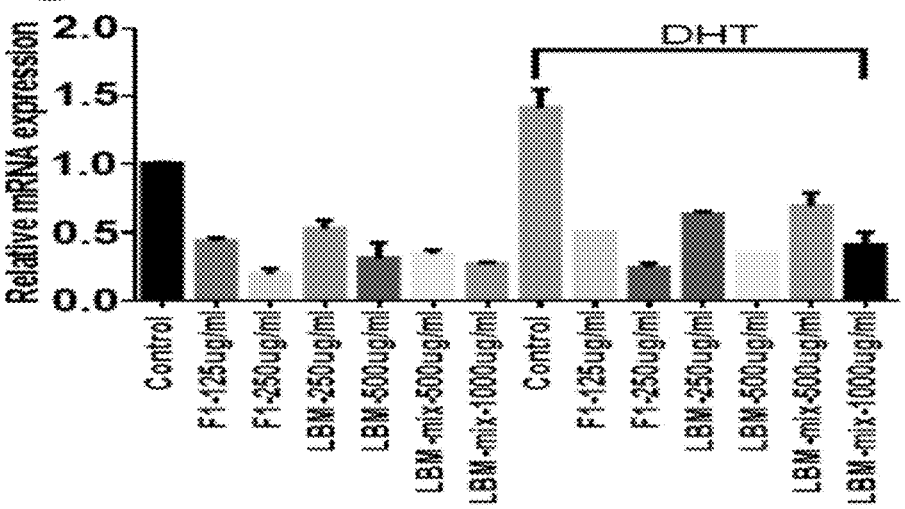
C. PSA mRNA

FIGURES 15A-C

A. C18 column

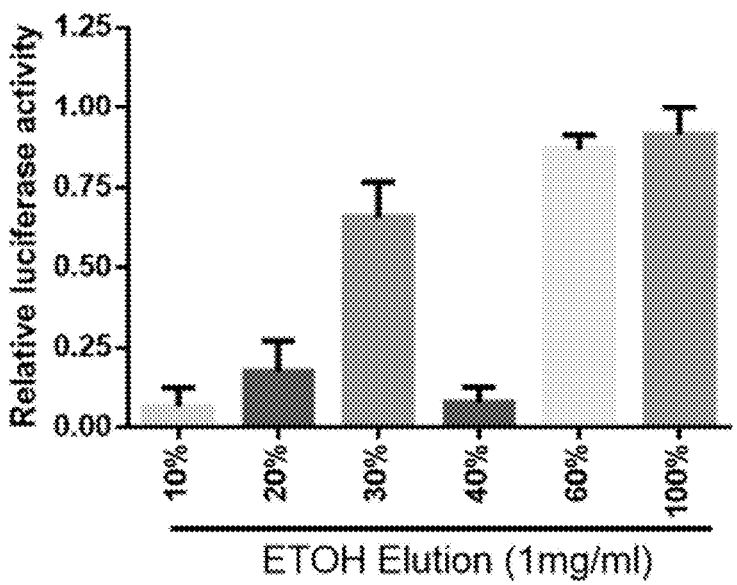

B.

| MW | Chemical | In ETOH elution in different fraction | IC50, Acitvity on AR (upto 80uM) |
|---|---|---|---|
| 290.2 | Catechin/Epicatechin | 20% | not active |
| 306.2 | Epigallocatechin | 10%, 20% | 15uM |
|  | or gallocatechin |  | 25uM |
| 180.16 | caffiec | 10% | not active |
| 354.3 | Chlorogenic acid | 10%, 20% | not active |
| 463.3 | Isoquercetin | 30%, 40% | not active |
| 463.3 | Hyperoside | 30%, 40% | not active |
| 447.2 | Astragalin | 40% | not active |
| 447.2 | Trifolin | 40% | not determined |
| 505.2 | Acetylated hyperoside | 40% | not commerical |
| 505.2 | Or Acetylated Isoquercetin | 40% | not commerical |
| 302.236 | quercetin | 40% | 40uM |
| 286.23 | Keampferol | 40% | 45uM |
| 458.3 | Epigallocatechin gallate EGCG | Not found |  |

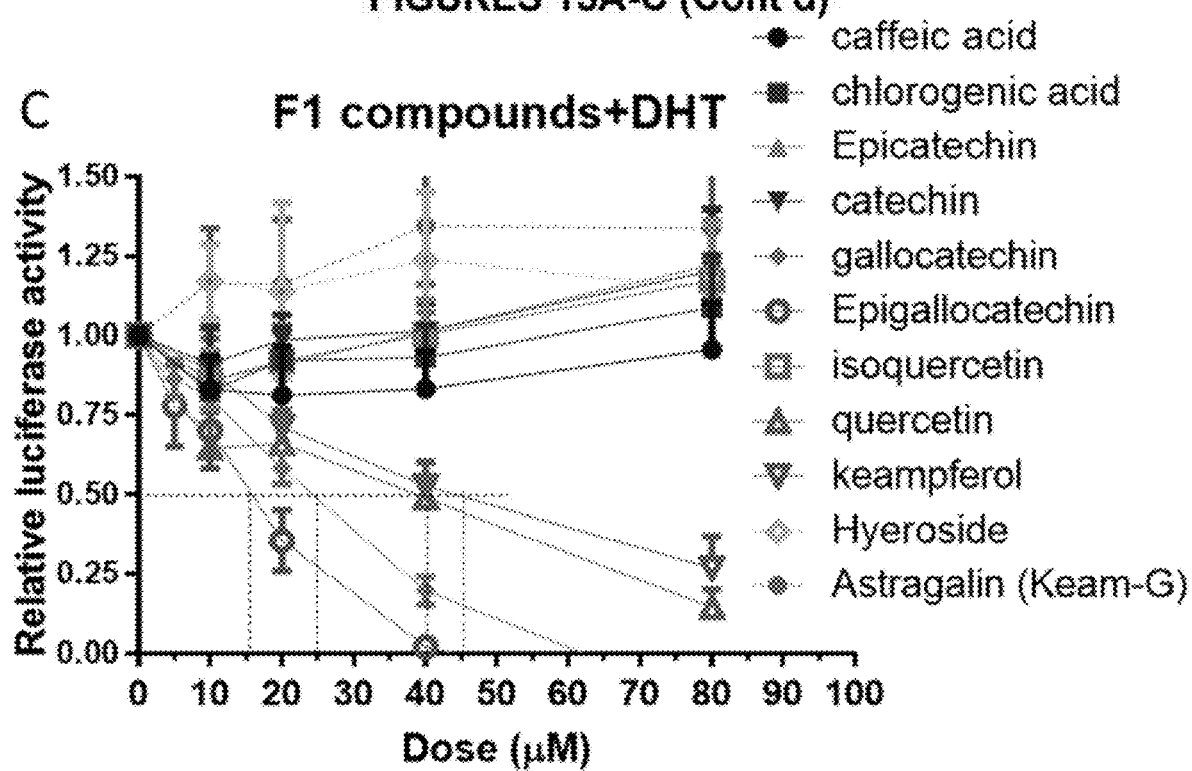
FIGURES 15A-C (Cont'd)

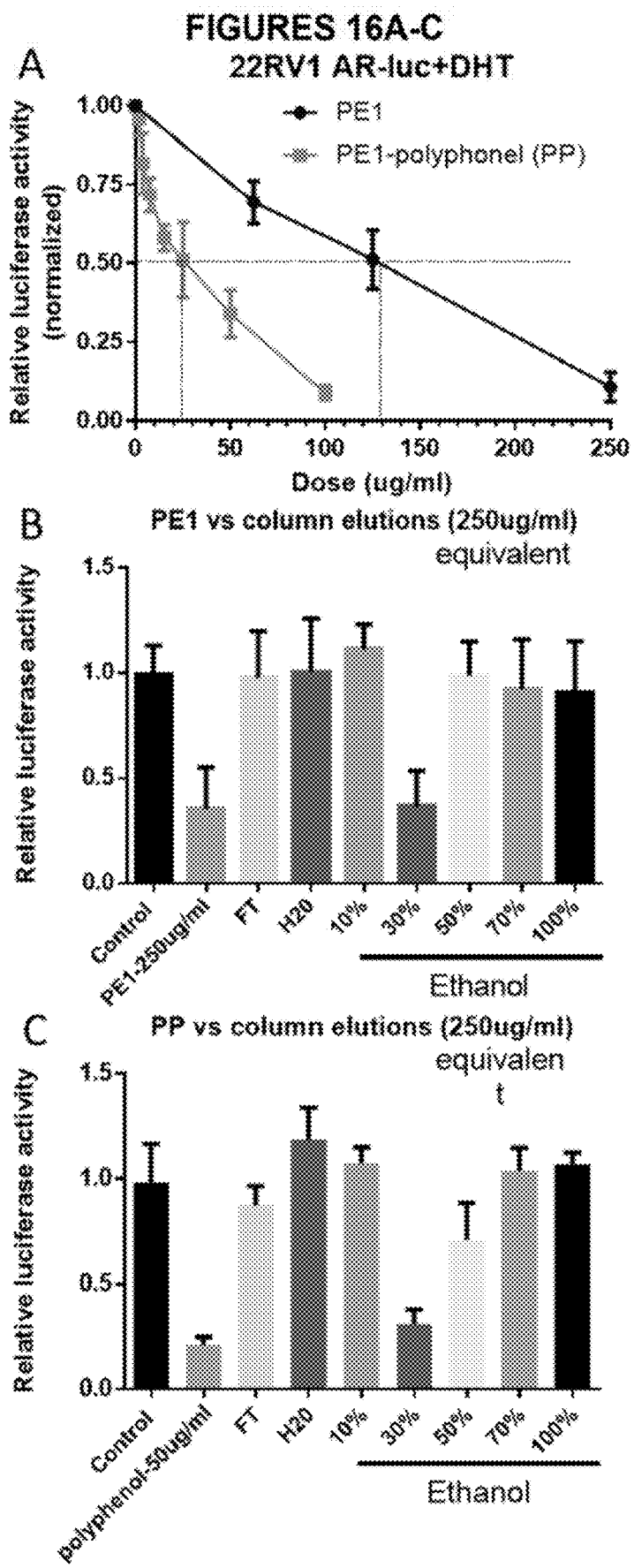

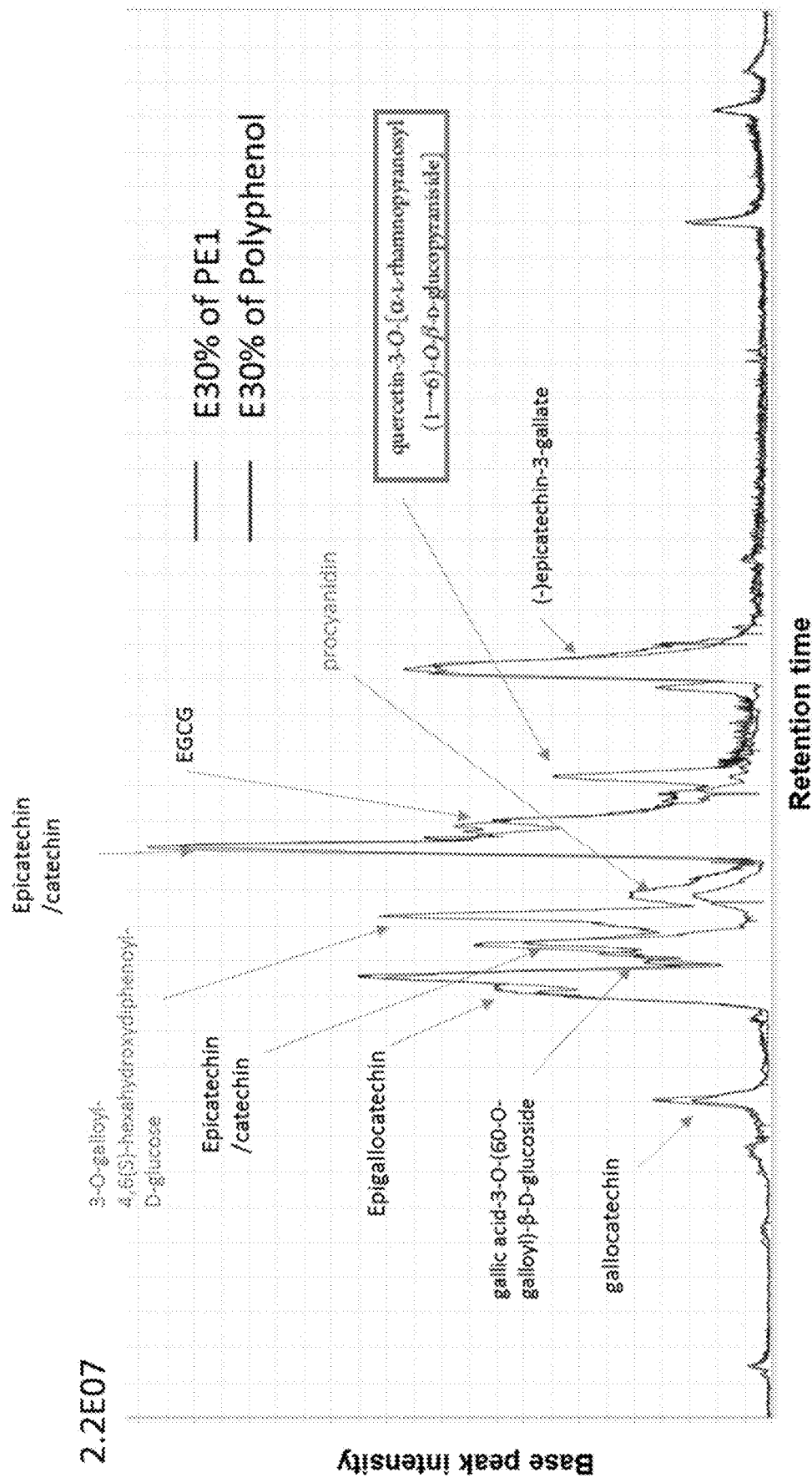

FIGURE 29 kaempferol-3-O-R-L-rhamnopyranosyl (1f6)-β-D-galactopyranoside 483.2
gallic acid-3-O-(60-O-galloyl)-β-D-glucoside
Or quercetin-3-O-β-D-glycopyranoside Fraction 42=EGCG Base peak Intensity Retention time PE1 (PE tea grade 1)

FIGURE 30

Cell Culture Cytotoxicity

*If max. concentration is bigger than IC50, (% of relative growth at the max. concentration)

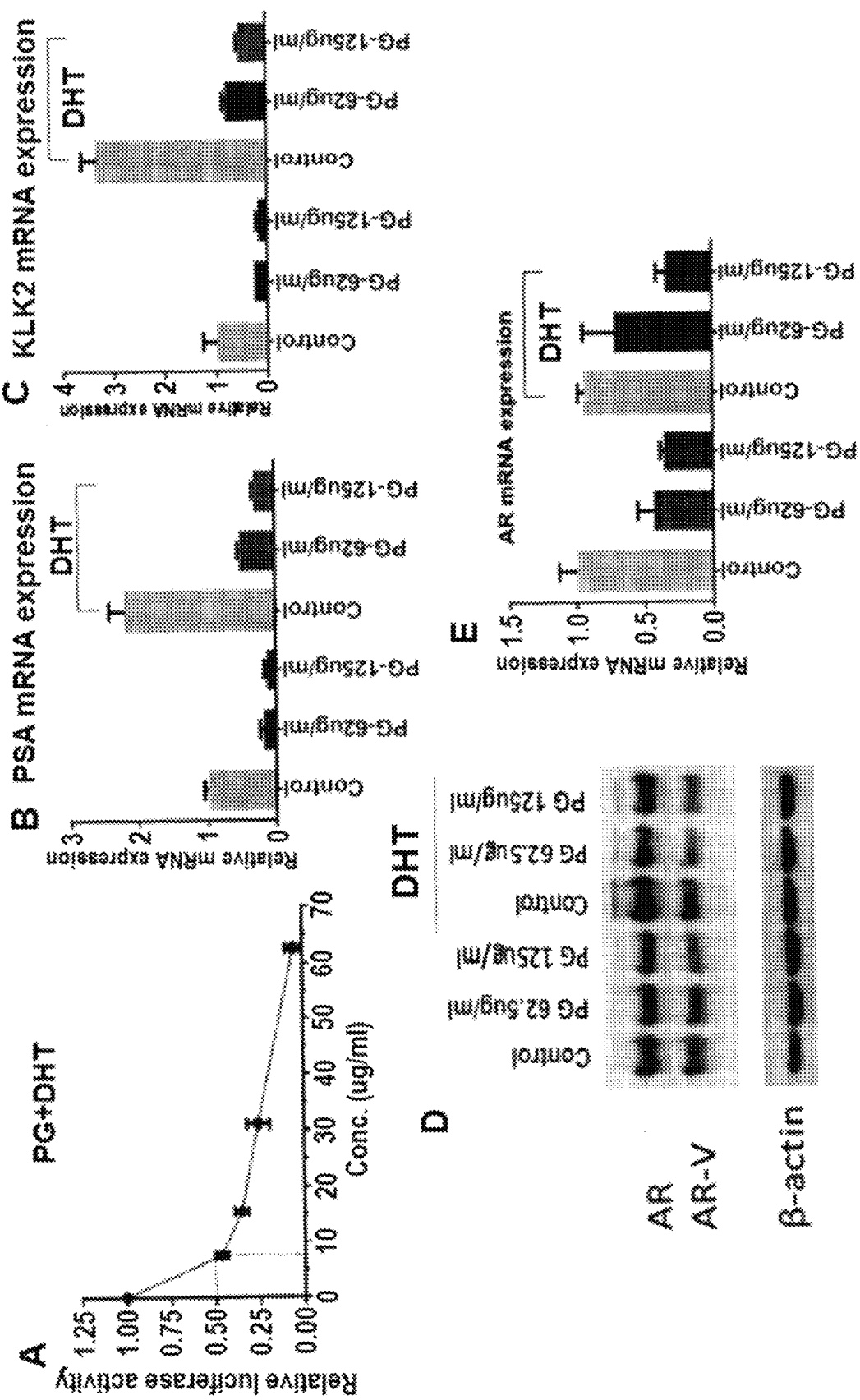
FIGURES 31A-E

SEQUENCE LISTING

<160> NUMBER OF SEQ ID NOS: 9

<210> SEQ ID NO 1
<211> LENGTH: 30
<212> TYPE: DNA
<213> ORGANISM: Homo sapiens

<400> SEQUENCE: 1
gtaattgcag aacagcaagt gctagctctc                30

<210> SEQ ID NO 2
<211> LENGTH: 21
<212> TYPE: DNA
<213> ORGANISM: Homo sapiens

<400> SEQUENCE: 2
cctggcttcc gcaacttaca c                         21

<210> SEQ ID NO 3
<211> LENGTH: 22
<212> TYPE: DNA
<213> ORGANISM: Homo sapiens

```
<400> SEQUENCE: 3
ggacttgtgc atgcggtact ca                                              22

<210> SEQ ID NO 4
<211> LENGTH: 23
<212> TYPE: DNA
<213> ORGANISM: Homo sapiens

<400> SEQUENCE: 4
ggtggctgtg tacagtcatg gat                                             23

<210> SEQ ID NO 5
<211> LENGTH: 23
<212> TYPE: DNA
<213> ORGANISM: Homo sapiens

<400> SEQUENCE: 5
tgtcttcagg ctcaaacagg ttg                                             23

<210> SEQ ID NO 6
<211> LENGTH: 24
<212> TYPE: DNA
<213> ORGANISM: Homo sapiens

<400> SEQUENCE: 6
accagaggag ttcttgaccc caaa                                            24

<210> SEQ ID NO 7
<211> LENGTH: 20
<212> TYPE: DNA
<213> ORGANISM: Homo sapiens

<400> SEQUENCE: 7
ccccagaatc acccgagcag                                                 20

<210> SEQ ID NO 8
<211> LENGTH: 21
<212> TYPE: DNA
<213> ORGANISM: Homo sapiens

<400> SEQUENCE: 8
gccacggctg cttccagctc c                                               21

<210> SEQ ID NO 9
<211> LENGTH: 24
<212> TYPE: DNA
<213> ORGANISM: Homo sapiens

<400> SEQUENCE: 9
ttgtgctggg tgccagggca gtga                                            24
```

INHIBITION OF ANDROGEN RECEPTOR BY EXTRACTS OF MEDICINAL HERBS AND COMPOSITIONS THEREOF

RELATED APPLICATION

This application is a § 371 National Phase application of PCT/IB2018/001296, which claims the benefit of priority of United States provisional application serial number U.S. 62/574,440 of identical title filed Oct. 19, 2017, the entire contents of which are incorporated by reference herein.

FIELD OF THE INVENTION

The presented invention relates to certain medicinal herbs and their extracts which have been found to inhibit the androgen receptor and are useful in the treatment of disease states and conditions which result from hyperactivity of the androgen receptor. Pharmaceutical compositions based upon these herbs and/or extracts obtained therefrom represent an additional aspect of the invention. Methods of treating a variety of disease states which are a result of hyperactivity of the androgen receptor as otherwise disclosed herein represent an additional aspect of the invention.

BACKGROUND OF THE INVENTION

The prostate is a gland in the male reproductive system. Most prostate cancers grow slowly; however, some grow more rapidly. The cancer cells may spread from the prostate to other parts of the body, particularly the bones and lymph nodes. Initially, prostate cancer may exhibit no symptoms. Symptoms arising at a later stage of development may include difficulty urinating, blood in the urine, or pain in the pelvis, back or when urinating. Other late symptoms may include fatigue due to low levels of red blood cells.

No single gene is believed to be responsible for prostate cancer; many different genes have been implicated. Mutations in 3RCA1 and BRCA2, important risk factors for ovarian cancer and breast cancer in women, have also been implicated in prostate cancer. Other linked genes include the Hereditary Prostate cancer gene 1 (HPC1), the androgen receptor, and the vitamin D receptor. TMPRSS2-ETS gene family fusion, specifically TMPRSS2-ERG or TMPRSS2-ETV1/4 promotes cancer cell growth.

The prostate glands require male hormones, known as androgens, to work properly. Androgens include testosterone, which is made in the testes; dehydroepiandrosterone, made in the adrenal glands; and dihydrotestosterone, which is converted from testosterone within the prostate itself. Androgens are also responsible for secondary sex characteristics such as facial hair and increased muscle mass. The androgen receptor (AR), also known as NR3C4 (nuclear receptor subfamily 3, group C, member 4), is a type of nuclear receptor that is activated by binding either of the androgenic hormones, testosterone, or dihydrotestosterone in the cytoplasm and then translocating into the nucleus. The main function of the androgen receptor is as a DNA-binding transcription factor that regulates gene expression; however, the androgen receptor has other functions as well. The androgen receptor helps prostate cancer cells to survive and its inhibition is a target for many anti cancer research studies; so far, no composition has been found that is effective in inhibiting the androgen receptor in humans.

Prostate cancer, alopecia, hepatocellular carcinoma, and acne vulgaris are a few examples of the myriad of diseases linked to androgen receptor signaling. These diseases have a significant impact on human health; for example, The American Cancer Society estimates that in 2009, prostate cancer will cause 27,360 deaths and 192,280 new cases will be diagnosed. In fact, one man in six will get prostate cancer in his lifetime and one in thirty-five will die from this disease. Androgen receptor inhibitors are the primary treatment option for androgen-related diseases. Current inhibitors prevent ligand binding to the androgen receptor, but these treatments can result in acquired resistance and serious side effects. Due to the limitations of current treatment options, alternative antiandrogen therapies are urgently needed.

BRIEF DESCRIPTION OF THE INVENTION

The present invention recognizes that certain herbs, which have a long history of use by humans, may be able to inhibit the androgen receptor. Those herbs can be used singly or in combination with others, or as a lead for isolation of active chemicals for inhibition of the androgen receptor. Those herbs may be useful for cancer prevention particularly prostate hyperplasia or prostate cancer and other diseases caused by hyperactivity of the androgen receptor.

To address this potential, the inventors studied the effects of herbal water extracts from over 250 formulations, across 25 signaling pathways, using primary luciferase reporter assay and other enzymatic reactions. Eleven (11) herbs showed androgen receptor inhibition.

The present invention therefore relates to extracts obtained from the group of 11 (eleven) herbs consisting of *Aloe barbadensis* (Aloe vbera) (蘆薈:F3), *Rheum palmatum* L. (大黃:B6), *Stephania tetrandra*(汉防己:C4), *Phellodendron chinense* Schneid. (黃柏:D8), *Euphorbia humifusa* (地錦草:S6), *Eclipta prostrata* (墨旱蓮:I2), *Apocynum venetum* L. (羅布麻:F1), *Portulaca oleracea* L. (马齿苋:F5), *Sanguisorba officinalis* L. (地榆:E5), *Camellia sinensis* var. *assamica* (Mast.) Kitamura/Chang (puer tea, 普洱:PE), *Punica granatum*. (石榴:PG), and mixtures thereof, including mixtures of two, three, four, five, six, seven, eight, nine, ten and eleven of the aforementioned herbs and/or their extracts). Such herbs are inhibitors of the androgen receptor and accordingly are effective in pharmaceutical compositions or nutritive supplements to treat, inhibit, prevent, reduce the incidence of, ameliorate and/or resolve any of a number of disease states or conditions resulting from androgen receptor hyperactivity. These diseases and/or conditions include for example, prostate hyperplasia, prostate cancer, including castration resistant prostate cancer, drug resistant prostate cancer, especially including drug resistant cancers associated with AR-Vs (androgen receptor splice variants), bicalutamide and/or enzalutamide resistant prostate cancer, hepatocellular cancer, hair loss and/or the growth of hair, especially in the scalp and in other regions of the body where hair growth is desirable, pattern hair loss (androgenetic alopecia) caused by high levels of DHT, acne, seborrhea, hirsutism (excessive body hair), hidradenitis suppurativa, paraphilias, precocious puberty in boys and polycystic ovary syndrome in women, among others.

One or more the above herbs and/or extracts, preferably a solvent extract such as an aqueous (water or a mixture of water and at least one $C_1$-$C_3$ alcohol) or $C_1$-$C_3$ alcohol (preferably methanolic or ethanolic more preferably ethanolic) extract pursuant to the present invention, can be used alone or in combination with a pharmaceutically acceptable carrier, additive or excipient to treat, inhibit, prevent, reduce the incidence of, ameliorate and/or resolve a number of disease states or conditions including, for example, prostate hyperplasia, prostate cancer and other diseases caused by hyperactivity of the androgen receptor. In certain embodiments, the composition can cause a reduction in hair loss and/or the growth of hair, especially in the scalp and in other regions of the body where hair growth is desirable. In certain embodiments, the composition can be used to treat castration resistant prostate cancer, drug resistant prostate cancer including drug resistant cancers associated with AR-Vs (androgen receptor splice variants) and/or over expression of androgen receptors. In an embodiments, the composition can be used to treat bicalutamide and/or enzalutamide resistant prostate cancer and hepatocellular cancer. In additional embodiments, the composition can be used to treat prostatic hyperplasia, pattern hair loss (androgenetic alopecia) caused by high level of DHT, acne, seborrhea, hirsutism (excessive body hair), hidradenitis suppurativa, paraphilias, precocious puberty in boys and polycystic ovary syndrome in women.

The present invention also relates to the discovery that a compound according to the group consisting of aloe-emodin, emodin, chrysophanol, rhein, sennoside-A, sennoside-C, sennoside-D, gallic acid, epigallocatechin, gallocatechin, quercetin, keampferol, epigallocatechin gallate, polyphenol fraction of *Camellia assamica* (PE1) and mixtures thereof, preferably, aloe-emodin, gallic acid, epigallocatechin, gallocatechin, epigallocatechin gallate, quercetin, keampferol, and polyphenol fraction of *Camellia assamica* (PE1) and mixtures thereof may be used alone or in combination with a pharmaceutically acceptable carrier, additive or excipient to treat, inhibit, prevent, reduce the incidence of, ameliorate and/or resolve a number of disease states or conditions including, for example, prostate hyperplasia, prostate cancer, and other diseases caused by hyperactivity/overactivity of the androgen receptor. In certain embodiments, the compound or mixtures of compounds may be used in the reduction in hair loss and/or the growth of hair, especially in the scalp and in other regions of the body where hair growth is desirable. In certain embodiments, the compound or mixture of compounds can be used to treat, inhibit, reduce the incidence or likelihood of, ameliorate and/or resolve castration resistant prostate cancer, drug resistant prostate cancer including drug resistant cancers associated with AR-Vs (androgen receptor splice variants) and/or over expression of androgen receptors. In an embodiment, the compounds or mixtures of compounds can be used to treat enzalutamide resistant prostate cancer and/or hepatocellular cancer. In additional embodiments, the compound or mixture of compounds can be used to treat prostatic hyperplasia, pattern hair loss (androgenetic alopecia) caused by high level of DHT, acne, seborrhea, hirsutism (excessive body hair), hidradenitis suppurativa, paraphilias, precocious puberty in boys and polycystic ovary syndrome in women. Of course, herbs which contain one or more of these compounds may be used in place of these compounds for the biological effects these compounds exhibit.

The above herbs and/or their extracts may be used alone or in further combination with at least one additional compound selected from the group consisting of aloe-emodin, gallic acid, epigallocatechin (EGC), gallocatechin (GC), epigallocatechin gallate (EGCG), quercetin and keampferol. Each of these agents or herbs which contain these compounds may be used alone or in combination with each other for the treatment of one or more of the disease states and/or conditions disclosed herein.

Since these herbs and/or compounds listed above can inhibit the growth of 22RV1, which are resistant to bicalutamide and enzalutamide, these herbs and/or compounds may be developed to target bicalutamide and/or enzalutamide resistant prostate cancer.

BRIEF DESCRIPTION OF THE DRAWINGS

FIGS. 1A-I are graphs showing the effects of selected herbal water extracts on androgen receptor mediated transcription activity of 22RV1 AR-luciferase reporter cells in condition with dihydrotestosterone (DHT). The selected herbal extracts were nine (9): *Aloe barbadensis* (蘆薈:F3), *Rheum palmatum* L. (大黃:B6), *Stephania tetrandra*(汉防己:C4), *Phellodendron chinense* Schneid. (黃柏:D8), *Euphorbia humifusa* (地錦草:S6), *Eclipta prostrata* (墨旱莲:I2), *A. venetum* L. (羅布麻:F1), *Portulaca oleracea* L. (马齿苋:F5), *Sanguisorba officinalis* L. (地榆:E5).

FIGS. 3A-D are graphs showing the effect of herbal water extracts on the mRNA expression of androgen receptor target genes: kallikrein/KLK (A, C) and prostate specific antigen/PSA (B, D) of 22RV1 in condition with and without DHT. qRT-PCR was used to determine the relative mRNA expression where beta-actin was used as internal control. *Aloe vera* (蘆薈:F3), *Rheum palmatum* L. (大黃:B6), *Stephania tetrandra*(汉防己:C4), *Phellodendron chinense* Schneid. (黃柏:D8), *Euphorbia humifusa* (地錦草:S6), *Eclipta prostrata* (墨旱莲:I2), *A. venetum* L. (羅布麻:F1), *Portulaca oleracea* L. (马齿苋:F5), *Sanguisorba officinalis* L. (地榆:E5), *Camellia assamica* (Mast) Chang (puer tea, 普洱茶:PE). In FIGS. 3E and 3F, water extract prepared using instant dissolving powder of puer tea (PE-P) and water extract prepared using raw tea material of puer tea were compared for their effect on KLK and PSA mRNA expression of 22RV1 cells.

FIG. 4A shows the effect of herbal water extracts on androgen receptor protein expression of 22RV1 in conditions with and without DHT. Rabbit monoclonal antibody was used to detect androgen receptor protein expression following 24 h treatment. β-actin was used as loading control. *Aloe vera* (蘆薈:F3), *Rheum palmatum* L. (大黃:B6), *Stephania tetrandra*(汉防己:C4), *Phellodendron chinense* Schneid. (黃柏:D8), *Euphorbia humifusa* (地錦草:S6), *Eclipta prostrata* (墨旱莲:I2) *A. venetum* L. (羅布麻:F1), *Portulaca oleracea* L. (马齿苋:F5), *Sanguisorba officinalis* L. (地榆:E5), *Camellia assamica* (Mast) Chang (puer tea, 普洱茶:PE). In FIG. 4B, water extract prepared using instant dissolving powder of puer tea (PE-P) and water extract prepared using raw tea material of puer tea were compared for their effect on AR protein expression of 22RV1 cells.

FIGS. 5A and B show the effect of herbal water extracts on androgen receptor mRNA expression of 22RV1 in conditions without DHT (A,C) and with DHT (B,C). qRT-PCR was used to quantify the AR mRNA expression, β-actin was used for normalization. *Aloe vera* (蘆薈:F3), *Rheum palmatum* L. (大黃:B6), *Stephania tetrandra*(汉防己:C4), *Phellodendron chinense* Schneid. (黃柏:D8), *Euphorbia humifusa* (地錦草:S6), *Eclipta prostrata* (墨旱莲:I2), *A. venetum* L. (羅布麻:F1), *Portulaca oleracea* L. (马齿苋:F5), *Sanguisorba officinalis* L. (地榆:E5) *Camellia assamica* (Mast) Chang (puer tea, 普洱茶:PE). In FIG. 5C, water extract prepared using instant dissolving powder of puer tea (PE-P)

and water extract prepared using raw tea material of puer tea were compared for their effect on AR mRNA expression of 22RV1 cells.

Figure 6:
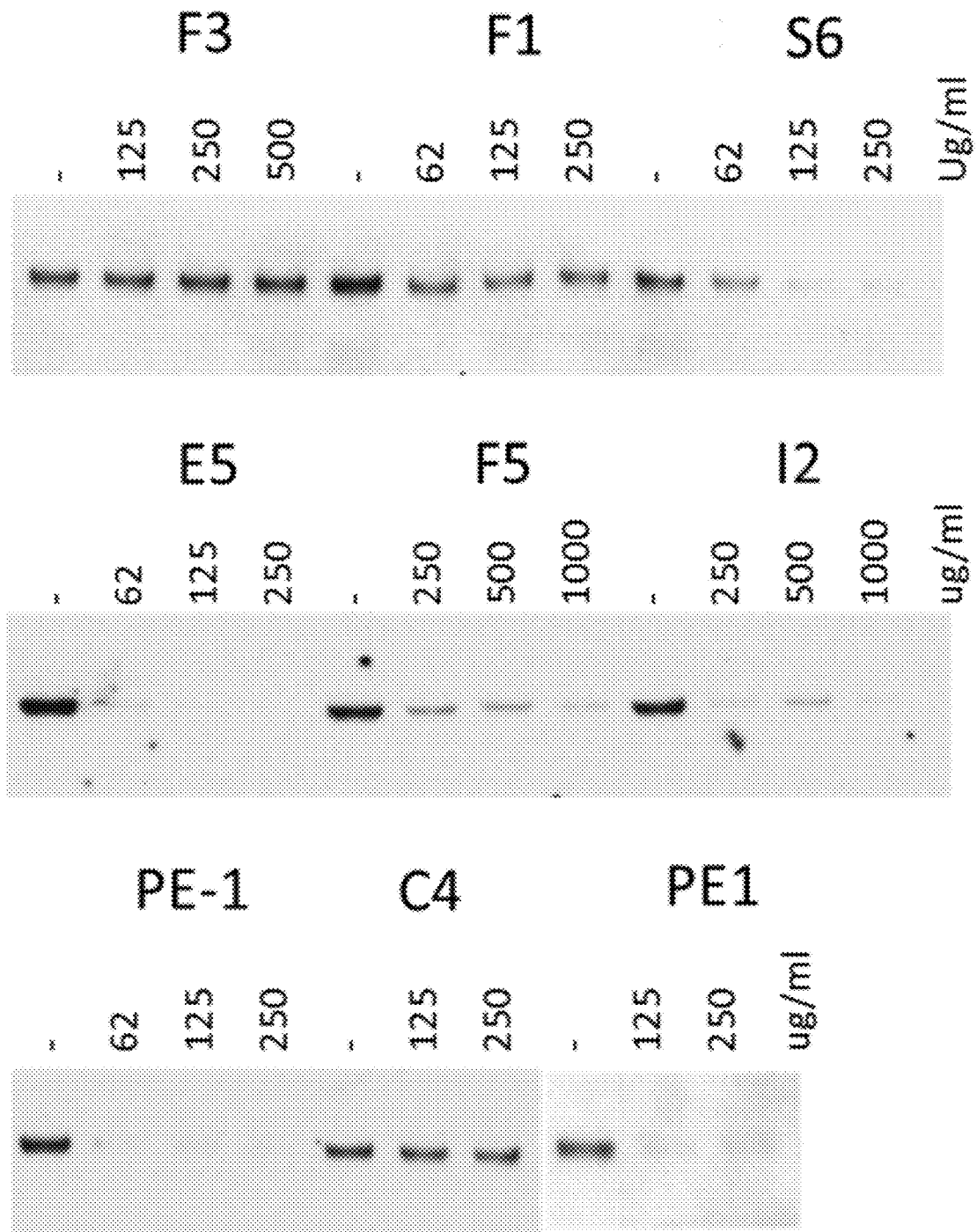

FIG. 6 shows the effect of herbs water extracts on the interaction between AR protein and DNA (with androgen binding site). Androgen receptor-DNA interaction pull down assay was performed by mixing biotin label DNA 5-gtaat-tgcAGAACAgcaAGTGCTagctctc-3' (SEQ ID NO: 1) (with androgen binding site) and nuclear lysis with androgen receptor protein (extracted from 22RV1 cells pre-stimulated with DHT 25 nM for overnight). Streptavidin-Dynabead was used to trap down the DNA-AR complex under magnetic condition. Western blotting was used to detect the amount of pull down AR protein. Inhibition between DNA and androgen receptor binding will reduce the amount of AR protein pull down. Aloe vera (蘆薈:F3), Stephania tetrandra(汉防己:C4), Euphorbia humifusa (地錦草:S6), Eclipta prostrata (墨旱莲:I2), A. venetum L. (羅布麻:F1), Portulaca oleracea L. (马齿苋:F5), Sanguisorba officinalis L. (地榆:E5), Camellia assamica (Mast) Chang (puer tea, 普洱茶:PE).

FIG. 6A, Table 1 shows the possible target of the following herbs on AR signaling pathway. Aloe vera (蘆薈:F3), Rheum palmatum L. (大黄:B6), Stephania tetrandra(汉防己:C4), Phellodendron chinense Schneid. (黄柏:D8), Euphorbia humifusa (地錦草:S6), Eclipta prostrata (墨旱莲:I2), A. venetum L. (羅布麻:E1) Portulaca oleracea L. (马齿苋:F5), Sanguisorba officinalis L. (地榆:E5). FIG. 6B, Table 2 shows the cytotoxicity of herbal water extracts for 22RV1 cells and Du145 cells with DHT. Aloe vera (蘆薈:F3), Rheum palmatum L. (大黄:B6), Stephania tetrandra(汉防己:C4), Phellodendron chinense Schneid. (黄柏:D8), Euphorbia humifusa (地錦草:S6), Eclipta prostrata (墨旱莲:I2), A. venetum L. (羅布麻:F1), Portulaca oleracea L. (马齿苋:F5), Sanguisorba officinalis L. (地榆:E5), Camellia assamica (Mast) Chang (puer tea, 普洱茶:PE), Punica granatum water extract ((石榴:PG, pomegranate).

FIGS. 7A-L are graphs showing the effects of herbal water extract on the growth of DU145 and 22RV1 xenograft in vivo. Curves shown significant inhibition on the growth of xenograft were label with *(P<0.05). Aloe barbadensis (蘆薈:F3), Euphorbia humifusa (地錦 草:S6), Eclipta prostrata (墨旱莲:I2), A. venetum L. (羅布麻:F1), Sanguisorba officinalis L. (地:榆E5).

FIGS. 8A-H shows the effect of S6, F5, PE1 water extract and Enzalutamide on the growth of LNCaP xenograft (A-C) and Du145 (D-F) in nude mice. Significant inhibition on the growth of xenograft were label with *(P<0.05) t-test at day 14. (G, H) Effects of different treatment on the KLK2 and PSA mRNA of LNCaP tumor where significant inhibition was labeled with *(P<0.05).

Figure 9:
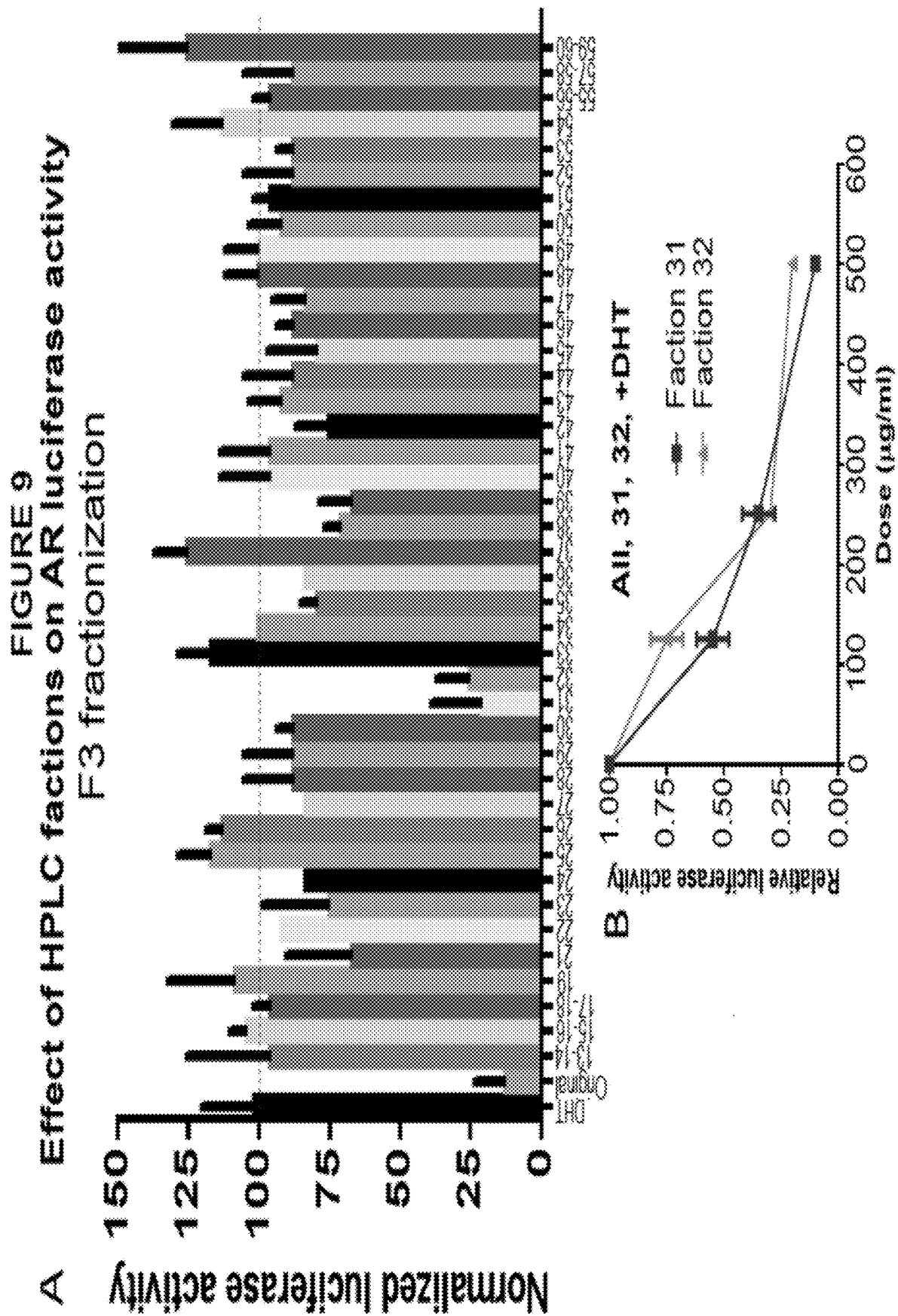

FIG. 9 shows the inhibitory activity of the fractions of F3 obtained from preparative HPLC. A. Inhibitory activity of the fractions of F3 obtained from preparative HPLC using luciferase reporter assay in which 500 ug/ml (equivalent dose to F3 crude water extract) was used for all fractions. B. Different dose of fraction 31 and 32 were tested for their AR inhibition activity using luciferase reporter assay.

Figure 10:
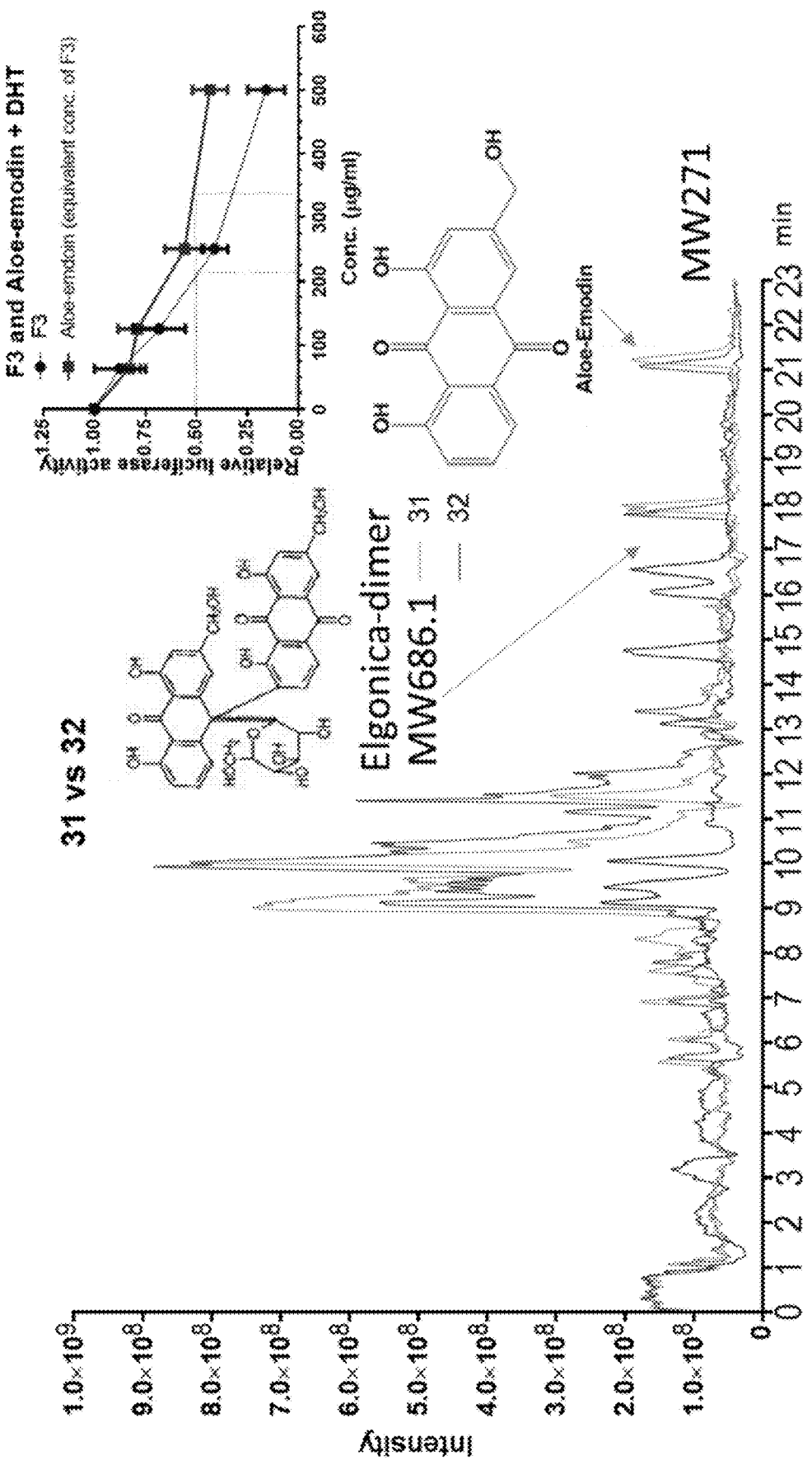

FIG. 10 shows the LC-MS for fraction 31 and 32 from fractionation of F3 using preparative HPLC. Insert figure showed that the equivalent amount of aloe-emodin was compared to crude water extract of F3 using luciferase report assay.

FIG. 1 shows the effect of aloe-emodin derivatives on the activity of AR using luciferase reporter assay.

Figure 12:
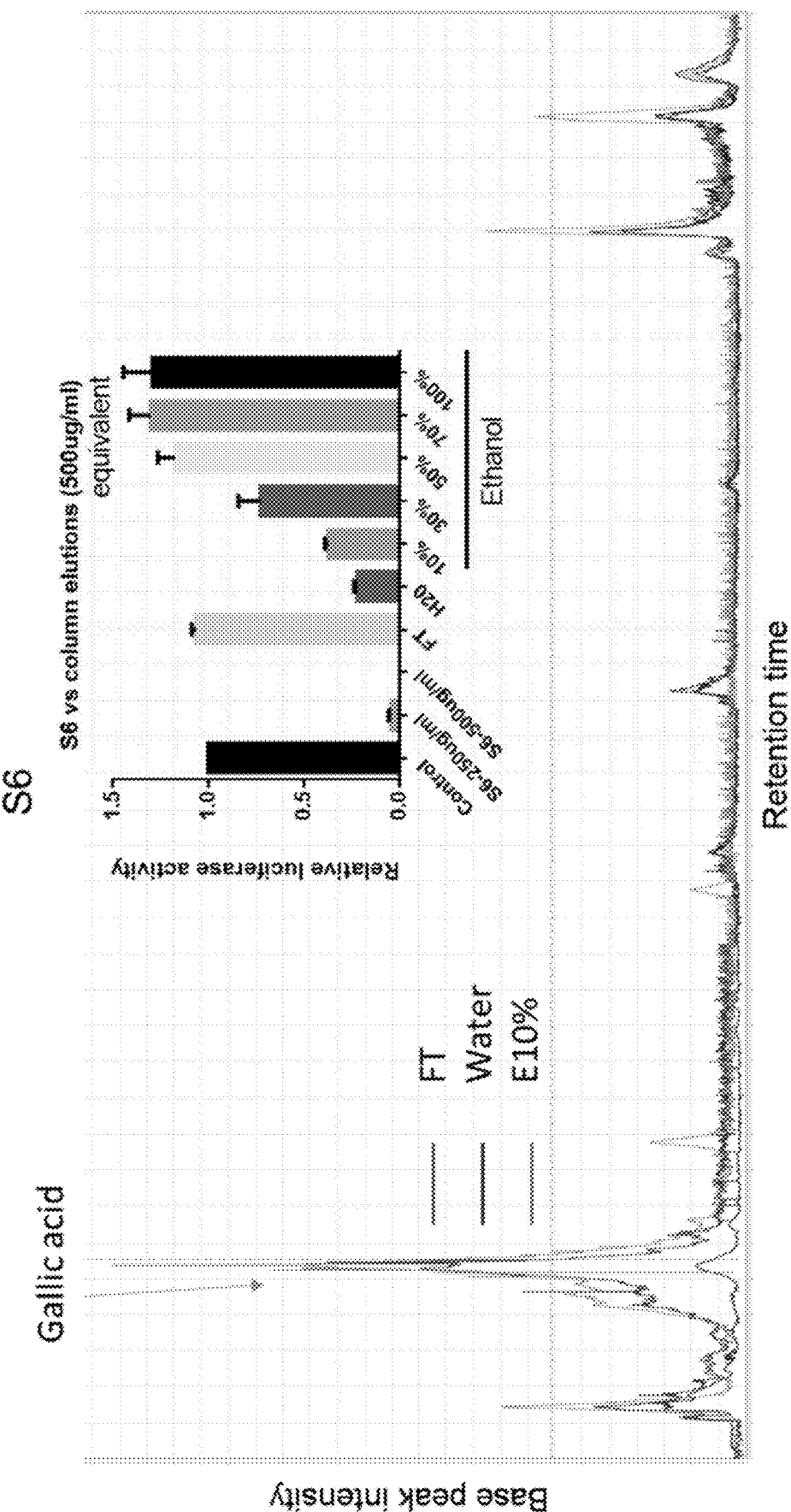

FIG. 12 shows the LC-MS for water elution and 100 ethanol elution (E10) of S6 water extract from solid phase extraction C18 column. Inserted figure showed that water elution and 10% ethanol elution (E10%) had relative stronger inhibitory effect on AR than other elution using luciferase report assay.

FIGS. 13A-F show the effect of gallic acid on AR activity. (A) the equivalent amount of gallic acid was compared to crude water extract of S6 using luciferase report assay. (B, C, D) Effect of gallic acid on KLK2, PSA and AR mRNA expression of 22RV1 cells with or without DHT. (E, F) Anti-tumor effect of gallic acid on 22RV1 tumor and Du145 tumor of nude mice.

FIGS. 14A-C. (A) shows the effect of F1 (Apocynum venetum) and Luo-bu-ma (LBM) tea from China on AR activity using luciferase reporter assay. (B, C) show the effect of F1 (Apocynum venetum) and Luo-bu-ma (LBM) tea from China on KLK2 and PSA mRNA expression using qPCR assay.

FIGS. 15A-C show the anti-AR activity of fractions of F1 using solid phase extraction column and list of active chemicals. (A) Anti-AR activity of fractions of F1 water extract using sold phase extraction C18 column. Water extract of F1 passed through C18 column and then elution with different concentration of ethanol. Fractions of F1 (1 mg/ml equivalent to F1 v crude water extract) were tested for their anti-AR activity using luciferase reporter assay. (B) Anti-AR activity of detectable chemicals in different fraction of F1 (C) Dose response of different purified compounds of F1 on AR activity using luciferase reporter assay.

FIGS. 16A-C. (A) shows Polyphenols (PP) (extract from PE) obtained from obtained from Gaoligongshan co.ltd showed anti-androgen receptor using 22RV1 luciferase reporter cell assay. (B, C) show the anti-AR activity of different fractions of PE1 or PP (polyphenol fraction).

FIG. 17 shows the LC-MS profiles for 30% ethanol elution of F1 and PP (polyphenol).

Figure 18:
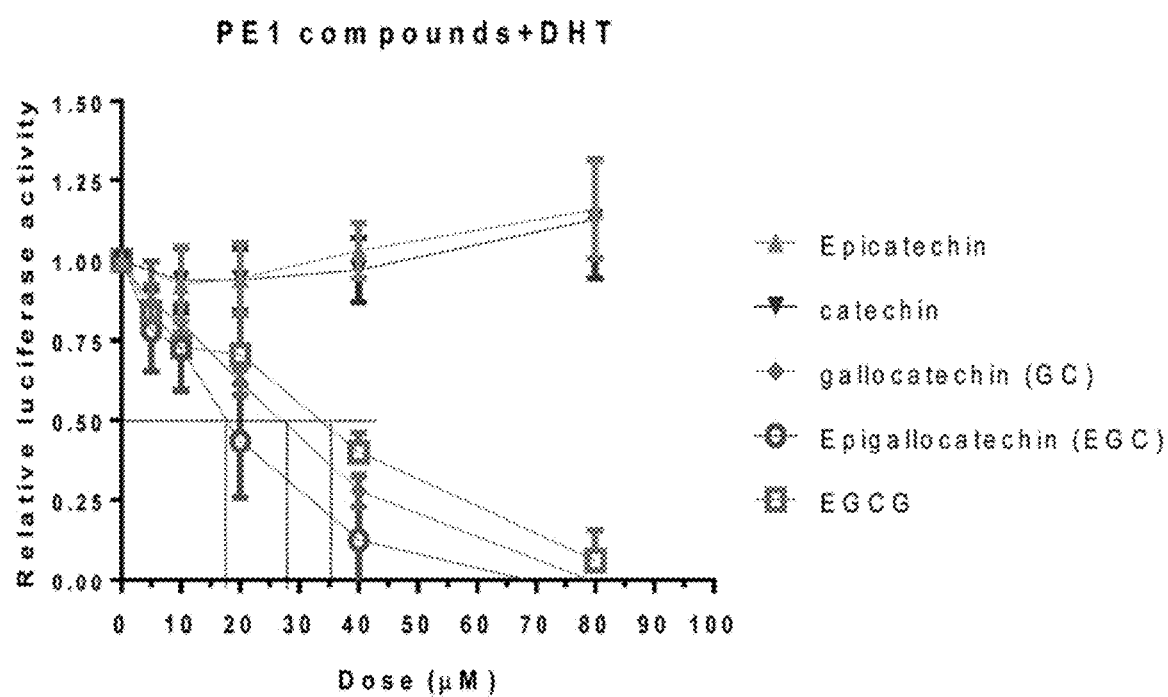

FIG. 18 shows the effect of epicatechin, catechin, gallocatechin (GC), Epigallocatechin (EGC) and epigallocatechin gallate (EGCG) on AR activity which is determined using luciferase report assay.

Figure 19:
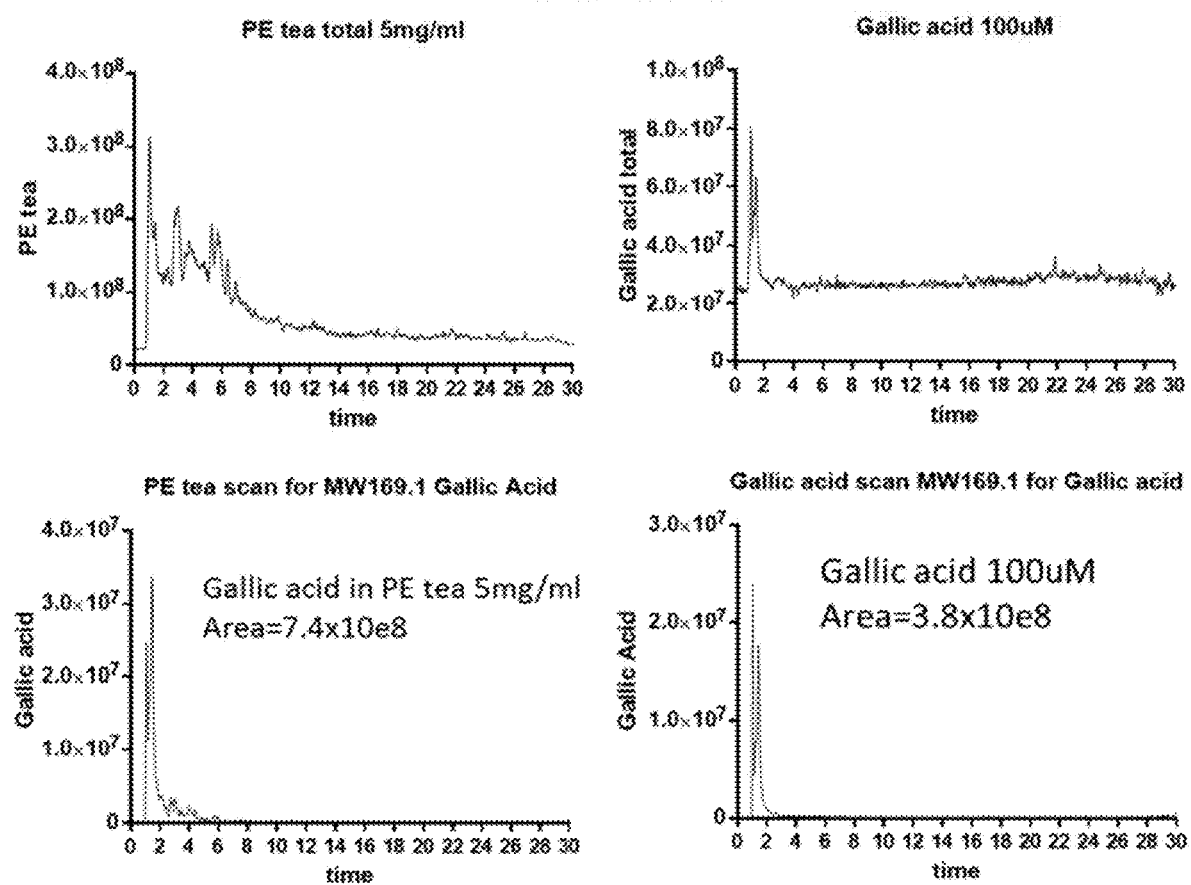

FIG. 19 shows the LC-MS profile for determination of gallic acid in PE using low molecular weight scan setting.

Figure 20:
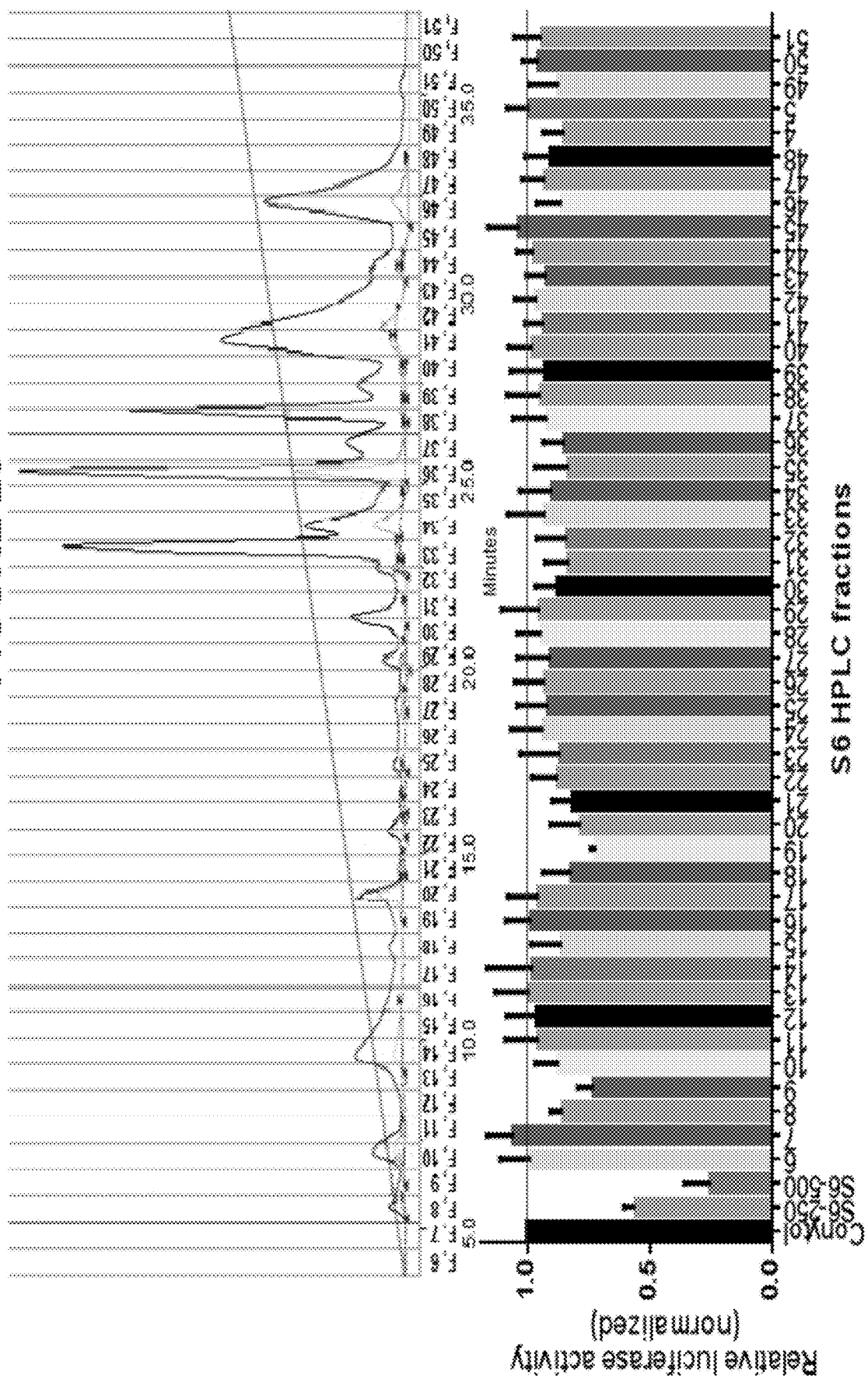

FIG. 20 shows that fraction 9 exhibited the strongest anti-androgen receptor activity from preparative HPLC fractions.

Figure 21:
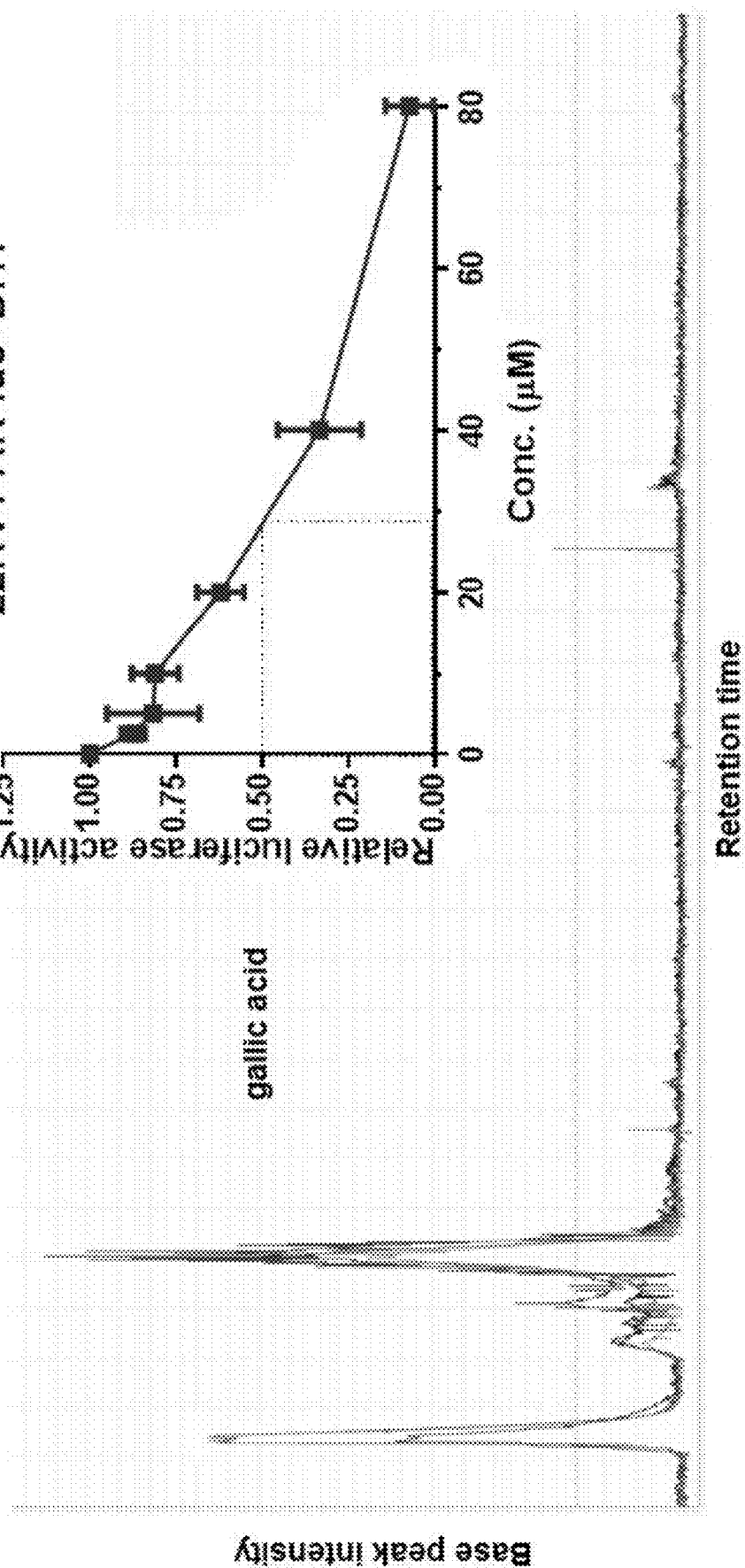

FIG. 21 shows that fraction 9 from preparative HPLC fraction contains gallic acid. Inset shows gallic acid activity displacing DHT at androgen receptors in 22RV1 cells.

Figure 22:
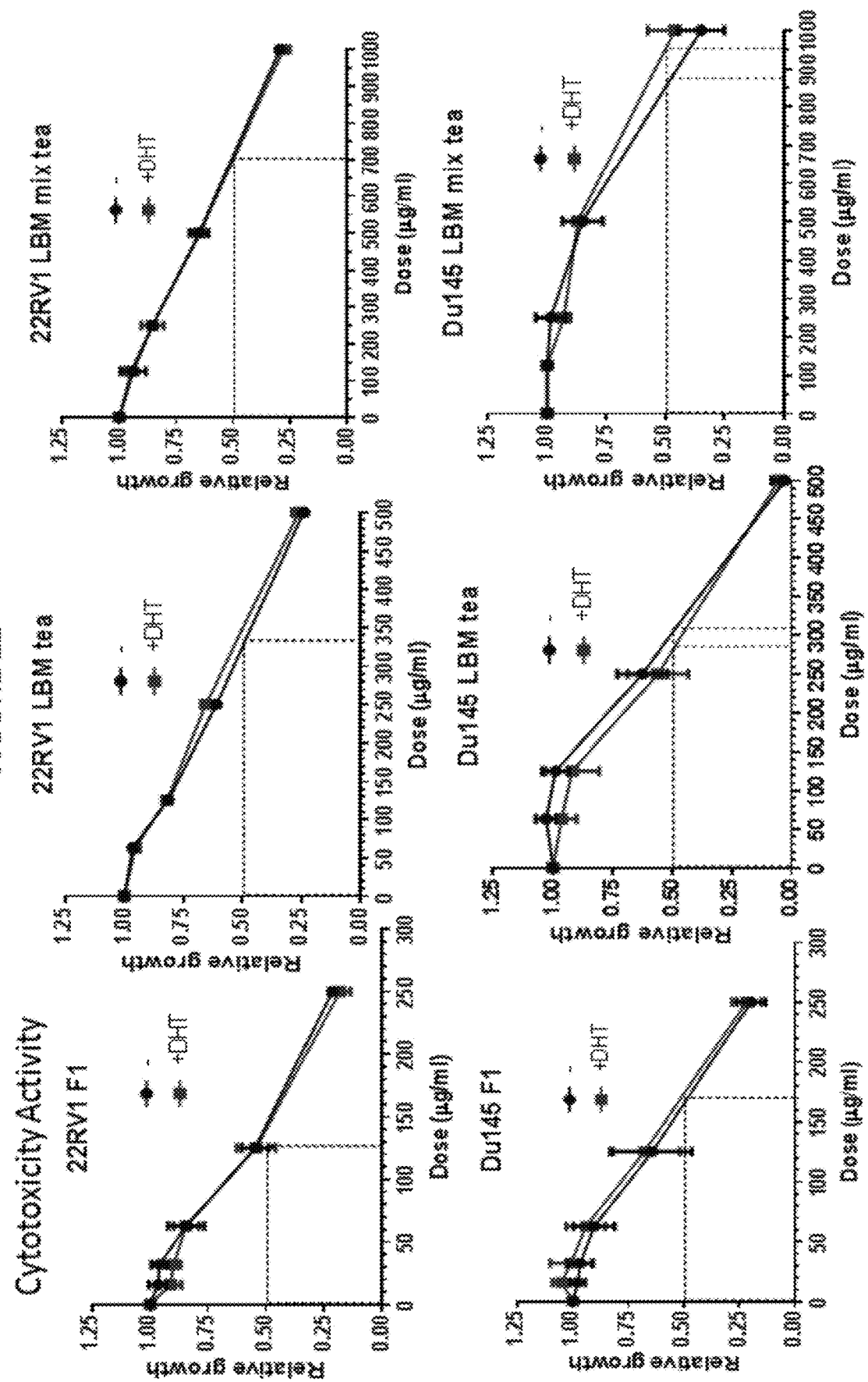

FIG. 22 shows the cytotoxicity of certain herbal extracts of F1, LBM tea and LBM mixed tea samples for 22RV1 cells and Du145 cells with or without DHT.

Figure 23:
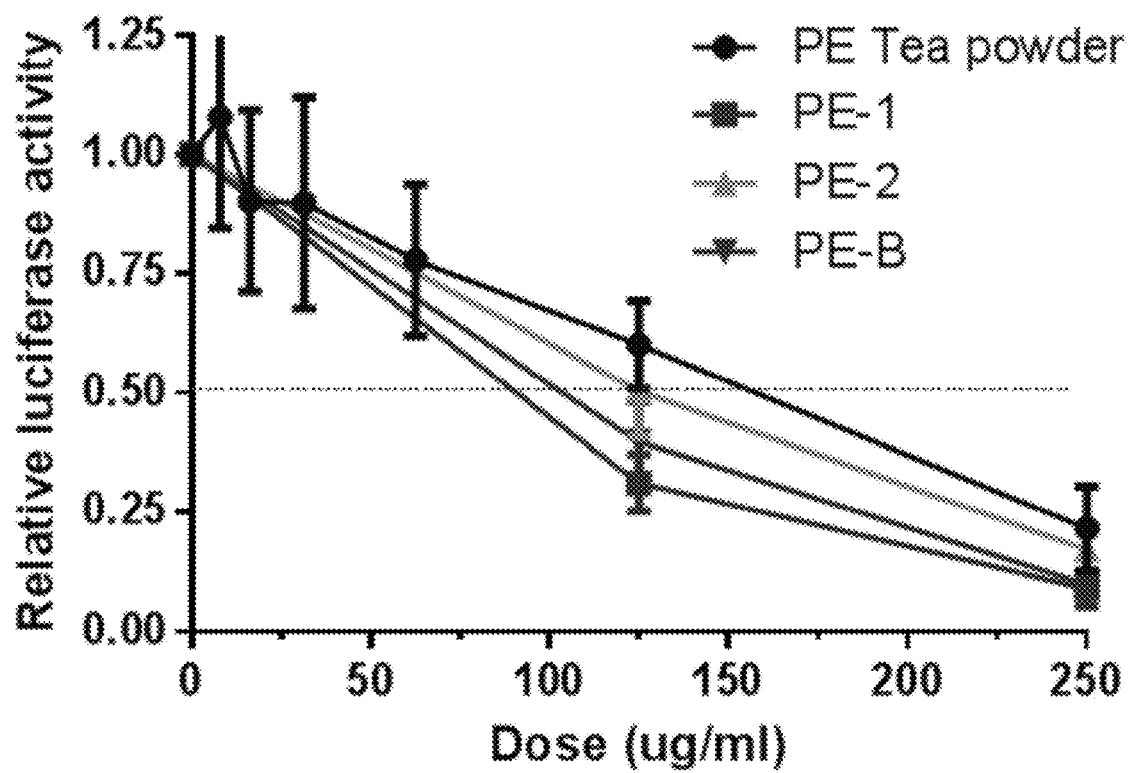

FIG. 23 shows the anti-androgen activity of different teas in 22RV1 luciferase report cell assay. PE-P was from Yunnan taslydee pure biological tea group co.ltd. and PE-1, PE-2, PE-B was obtained from Gaoligongshan co.ltd. Each of the samples showed anti-androgen receptor activity, although there was a slight difference in potency exhibited.

Figure 24:
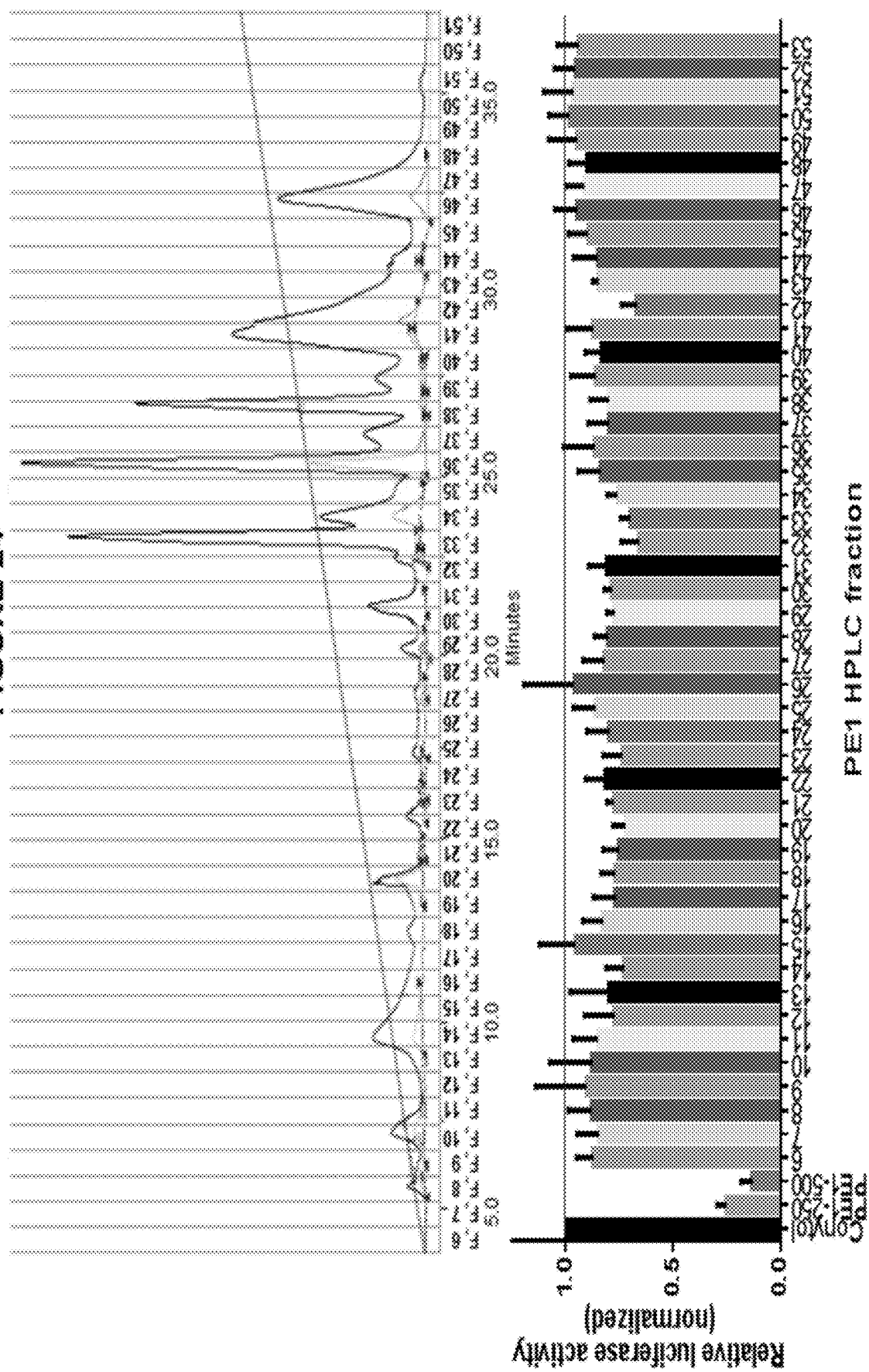

FIG. 24 shows the relative luciferase activity of components of PE1 extract isolated using HPLC.

Figure 25:
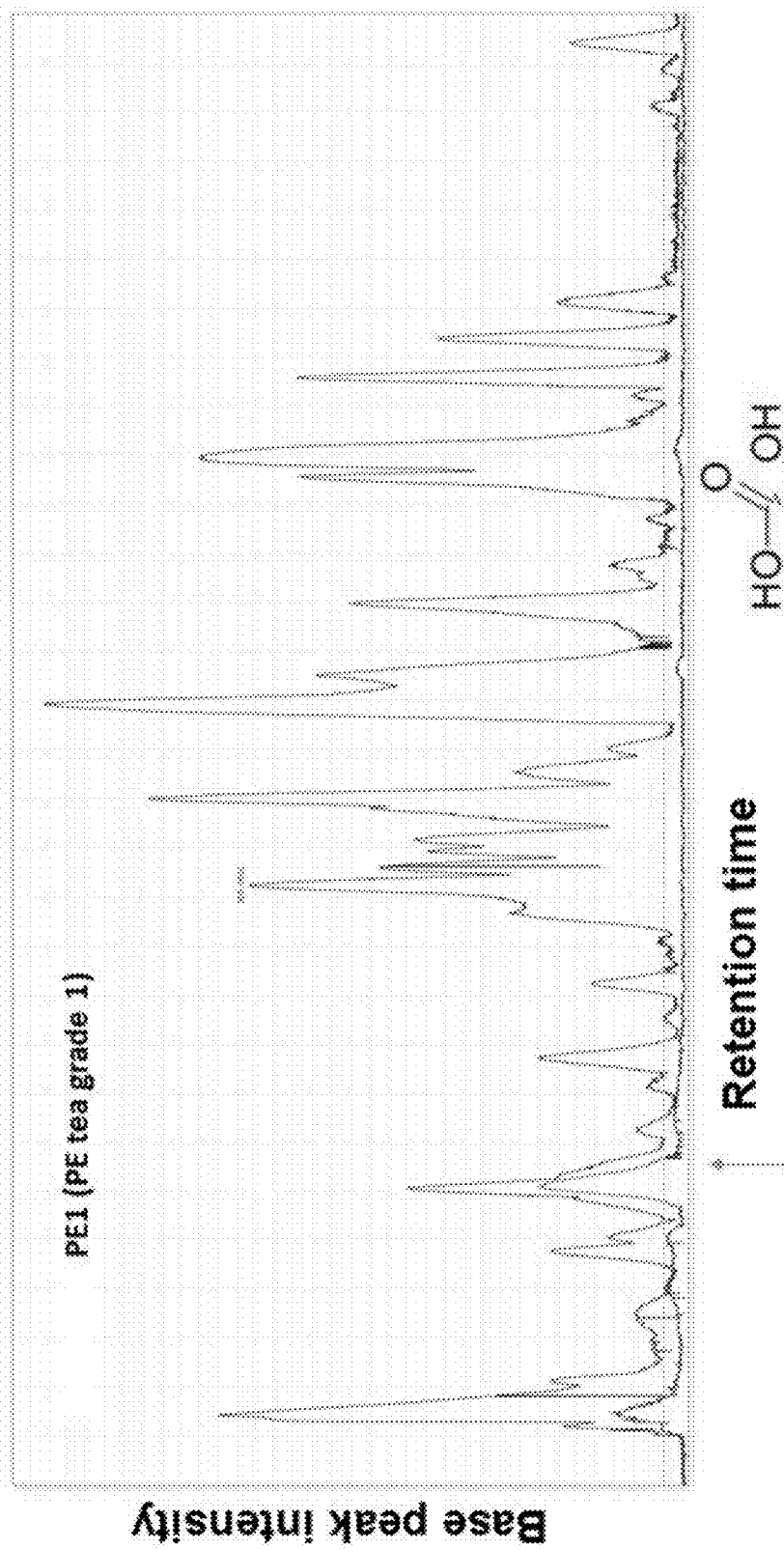

FIG. 25 shows the LC-MS from the preparative HPLC for PE Tea grade 1 and that fraction 13 corresponded to 5-galloylquinic acid being the active component in that fraction.

Figure 26:
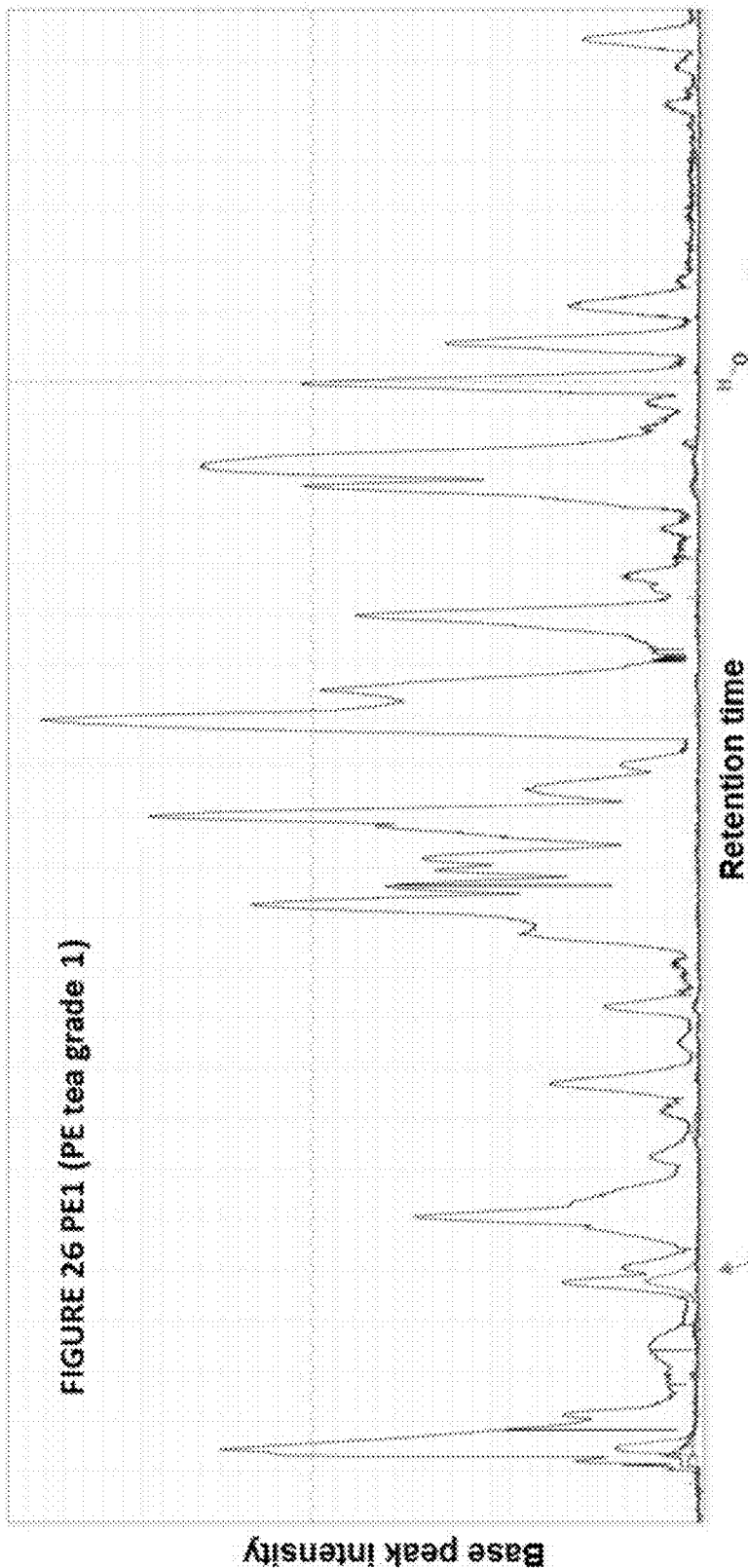

FIG. 26 shows the LC-MS from the preparative HPLC for PE Tea grade 1 and that fraction 21 corresponded to galloyl-beta-glucose being the active component in that fraction.

Figure 27:
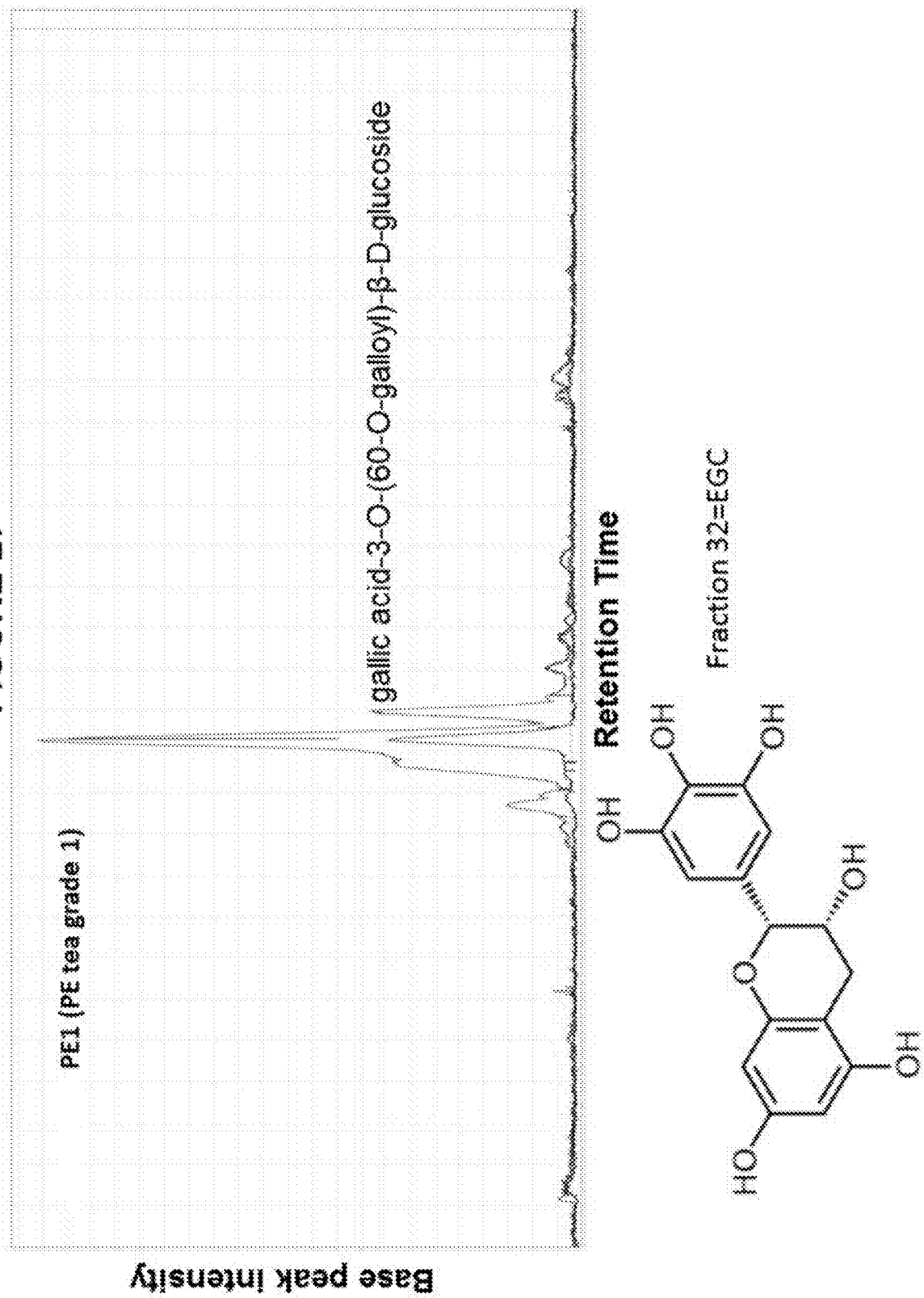

FIG. 27 shows the LC-MS from the preparative HPLC for PE Tea grade 1 and that fraction 32 corresponded to epicatechin gallate (ECG) being the active component in that fraction.

Figure 28:
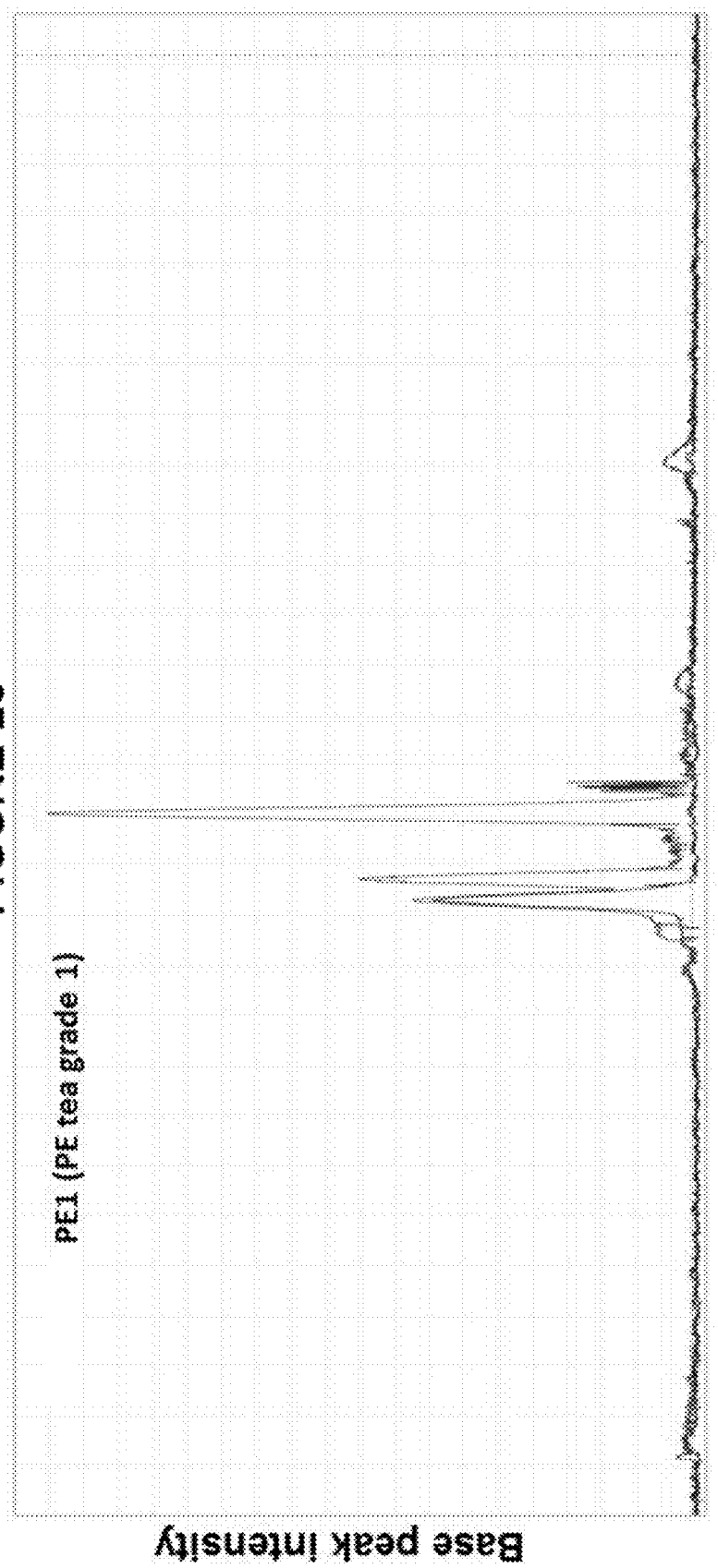

FIG. 28 shows the LC-MS from the preparative HPLC for PE Tea grade 1 and that fraction 33 also corresponded to epicatechin gallate (ECG) being the active component in that fraction.

FIG. 29 shows the LC-MS from the preparative HPLC for PE Tea grade 1 and that fraction 42 also corresponded to epigallocatechin gallate (EGCG) being the active component in that fraction.

FIG. 30 shows the cytotoxicity of various herbs (left axis) according to the present invention in a number of cell lines (top axis).

FIGS. 31A-E shows the effect of *Punica granatum* water extract (PG, or commonly called pomegranate) on androgen receptor activity of 22RV1 cells. (A) PG water extract showed inhibitory effect on AR mediated transcription of 22RV1 cells in luciferase report assay. (B and C) PG water extract inhibited PSA and KLK2 mRNA expression of 22RV1 in present or absent of DH T conditions in qRT-PCR assays. (D) PG water extract inhibited AR and AR-V protein of 22RV1 cells in western blot assay. (E) PG water extract down regulated AR mRNA of 22RV1 in qRT-PCR assay.

DETAILED DESCRIPTION OF THE INVENTION

The following definitions are used to describe the present invention. In instances where a term is not specifically defined, the definition to be used is that which one of ordinary skill in the art would use to define that term within the context of that term's use.

The term "patient" or "subject" is used to describe an animal, including a domesticated animal such as a dog, cat, cow, horse, sheep, goat or other similarly domesticated animal, especially a human patient in need, who receives medical attention, care, or treatment of the present invention.

The term "effective" is used to describe an amount of a component, extract, material or solvent which is used to produce an intended effect in amount consistent with the effect desired and may vary with the effect desired or which occurs.

The term "extract" is used to describe an aqueous or $C_1$-$C_3$ alcoholic (preferably, methanolic or ethanolic) extract of one or more of the following herbs selected from the group consisting of *Aloe barbadensis* (蘆薈:F3), *Rheum palmatum* L. (大黃:B6), *Stephania tetrandra* (汉防己:C4), *Phellodendron chinense* Schneid. (黃柏:D8), *Euphorbia humifusa* (地錦草:S6), *Eclipta prostrata* (墨旱蓮:I2), *A. venetum* L. (羅布麻:F1), *Portulaca oleracea* L. (马齿苋:F5), and *Sanguisorba officinalis* L. (地榆:E5), *Camellia sinensis* var. *assamica* (Mast.) Kitamura (普洱:PE), *Punica granatum*. (石榴:PG), and mixtures thereof (including mixtures of extracts from 2, 3, 4, 5, 6, 7, 8 or 9 herbs).

Extracts of the present invention are prepared by exposing one or more of the herbs which are described above to an effective amount of a solvent, preferably an aqueous or $C_1$-$C_3$ alcoholic (preferably, ethanolic) solvent, preferably heated (including boiling) for a period of time effective to extract medicinal components of the herbs into the solvent (for a period from a few minutes, to several hours to several days or more). Extracts of solvents may be prepared using standard methods readily available in the art and may include the preferred methods of preparation as otherwise described herein.

The term "aqueous" is used to describe a solvent which comprises water in any amount. Preferably, extracts are provided using water or water/alcohol, preferably, water/ethanol. Aqueous solvents used to provide extracts preferably comprise at least about 50% by volume water within this mixture and often water and another alcohol such as ethanol, isopropanol or methanol, among others. In preferred aspects, the solvent is heated (preferably boiled). The use of water or a water/ethanol mixture is preferred. It is noted that other solvents may also be used to provide extracts according to the present invention ("extraction solvent"), but the use of an aqueous alcohol, especially aqueous ethanol (wherein water preferably comprises at least about 5% up to about 95+%) is preferred. Water, ethanol, isopropanol, methanol, propanol and butanol and mixtures thereof, are generally used as solvents to provide extracts according to the invention.

The term "methanolic", "methanolic solvent", "ethanolic" or "ethanolic solvent" is used to describe a solvent which comprises methanol or ethanol in amounts greater than 50% by volume. As noted, the term "methanol" or "ethanolic" may overlap with the term "aqueous" as otherwise defined herein.

The term "solid extract" is used to describe an extract of one or more of the herbs as otherwise disclosed herein which has been dried, dehydrated, lyophilized or otherwise solidified to avoid the composition containing appreciable quantities of solvent.

The term "androgen receptor" is used to describe or denominate a protein complex typically occurring in cells, that binds to male hormones, known as androgens including testosterone, dehydroepiandrosterone, and dihydrotestosterone. More specifically, androgen receptor (AR), also known as NR3C4 (nuclear receptor subfamily 3, group C, member 4), is a type of nuclear receptor that is activated by binding either of the androgenic hormones, testosterone, or dihydrotestosterone in the cytoplasm and then translocating into the nucleus.

Hyperactivity of the androgen receptor (AR) is a key factor of carcinogenesis in prostate tissue and many other diseases including hepatocellular carcinoma, and acne vulgaris.

The term "prostate cancer" is used to describe a disease in which cancer develops in the prostate, a gland in the male reproductive system. It occurs when cells of the prostate mutate and begin to multiply uncontrollably. These cells may metastasize (metastatic prostate cancer) from the prostate to virtually any other part of the body, particularly the bones and lymph nodes, but the kidney, bladder and even the brain, among other tissues. Prostate cancer may cause pain, difficulty in urinating, problems during sexual intercourse, erectile dysfunction. Other symptoms can potentially develop during later stages of the disease.

Rates of detection of prostate cancers vary widely across the world, with South and East Asia detecting less frequently than in Europe, and especially the United States. Prostate cancer develops most frequently in men over the age of fifty and is one of the most prevalent types of cancer in men. However, many men who develop prostate cancer never have symptoms, undergo no therapy, and eventually die of other causes. This is because cancer of the prostate is, in most cases, slow-growing, and because most of those affected are over the age of 60. Hence, they often die of causes unrelated to the prostate cancer. Many factors, including genetics and diet, have been implicated in the development of prostate cancer. The presence of prostate cancer may be indicated by symptoms, physical examination, prostate specific antigen (PSA), or biopsy. There is concern about the accuracy of the PSA test and its usefulness in screening. Suspected prostate cancer is typically confirmed by taking a biopsy of the prostate and examining it under a microscope. Further tests, such as CT scans and bone scans, may be performed to determine whether prostate cancer has spread.

Treatment options for prostate cancer with intent to cure are primarily surgery and radiation therapy. Other treatments such as hormonal therapy, chemotherapy, proton therapy, cryosurgery, high intensity focused ultrasound (HIFU) also exist depending on the clinical scenario and desired outcome.

The age and underlying health of the man, the extent of metastasis, appearance under the microscope, and response of the cancer to initial treatment are important in determining the outcome of the disease. The decision whether or not to treat localized prostate cancer (a tumor that is contained within the prostate) with curative intent is a patient trade-off between the expected beneficial and harmful effects in terms of patient survival and quality of life.

An important part of evaluating prostate cancer is determining the stage, or how far the cancer has spread. Knowing the stage helps define prognosis and is useful when selecting therapies. The most common system is the four-stage TNM system (abbreviated from Tumor/Nodes/Metastases). Its components include the size of the tumor, the number of involved lymph nodes, and the presence of any other metastases.

The most important distinction made by any staging system is whether or not the cancer is still confined to the prostate or is metastatic. In the TNM system, clinical T1 and T2 cancers are found only in the prostate, while T3 and T4 cancers have spread elsewhere and metastasized into other tissue. Several tests can be used to look for evidence of spread. These include computed tomography to evaluate spread within the pelvis, bone scans to look for spread to the bones, and endorectal coil magnetic resonance imaging to closely evaluate the prostatic capsule and the seminal vesicles. Bone scans often reveal osteoblastic appearance due to increased bone density in the areas of bone metastasis—opposite to what is found in many other cancers that metastasize. Computed tomography (CT) and magnetic resonance imaging (MRI) currently do not add any significant information in the assessment of possible lymph node metastases in patients with prostate cancer according to a meta-analysis.

Prostate cancer is relatively easy to treat if found early. After a prostate biopsy, a pathologist looks at the samples under a microscope. If cancer is present, the pathologist reports the grade of the tumor. The grade tells how much the tumor tissue differs from normal prostate tissue and suggests how fast the tumor is likely to grow. The Gleason system is used to grade prostate tumors from 2 to 10, where a Gleason score of 10 indicates the most abnormalities. The pathologist assigns a number from 1 to 5 for the most common pattern observed under the microscope, then does the same for the second most common pattern. The sum of these two numbers is the Gleason score. The Whitmore-Jewett stage is another method sometimes used. Proper grading of the tumor is critical, since the grade of the tumor is one of the major factors used to determine the treatment recommendation.

Early prostate cancer usually causes no symptoms. Often it is diagnosed during the workup for an elevated PSA noticed during a routine checkup. Sometimes, however, prostate cancer does cause symptoms, often similar to those of diseases such as benign prostatic hypertrophy. These include frequent urination, increased urination at night, difficulty starting and maintaining a steady stream of urine, blood in the urine, and painful urination. Prostate cancer is associated with urinary dysfunction as the prostate gland surrounds the prostatic urethra. Changes within the gland therefore directly affect urinary function. Because the vas deferens deposits seminal fluid into the prostatic urethra, and secretions from the prostate gland itself are included in semen content, prostate cancer may also cause problems with sexual function and performance, such as difficulty achieving erection or painful ejaculation.

Advanced prostate cancer can spread to other parts of the body and this may cause additional symptoms. The most common symptom is bone pain, often in the vertebrae (bones of the spine), pelvis or ribs. Spread of cancer into other bones such as the femur is usually to the proximal part of the bone. Prostate cancer in the spine can also compress the spinal cord, causing leg weakness and urinary and fecal incontinence.

The specific causes of prostate cancer remain unknown. A man's risk of developing prostate cancer is related to his age, genetics, race, diet, lifestyle, medications, and other factors. The primary risk factor is age. Prostate cancer is uncommon in men less than 45, but becomes more common with advancing age. The average age at the time of diagnosis is 70. However, many men never know they have prostate cancer.

A man's genetic background contributes to his risk of developing prostate cancer. This is suggested by an increased incidence of prostate cancer found in certain racial groups, in identical twins of men with prostate cancer, and in men with certain genes. Men who have a brother or father with prostate cancer have twice the usual risk of developing prostate cancer. Studies of twins in Scandinavia suggest that forty percent of prostate cancer risk can be explained by inherited factors. However, no single gene is responsible for prostate cancer; many different genes have been implicated. Two genes (BRCA1 and BRCA2) that are important risk factors for ovarian cancer and breast cancer in women have also been implicated in prostate cancer.

Dietary amounts of certain foods, vitamins, and minerals can contribute to prostate cancer risk. Dietary factors that may increase prostate cancer risk include low intake of vitamin E, the mineral selenium, green tea and vitamin D. A large study has implicated dairy, specifically low-fat milk and other dairy products to which vitamin A palmitate has been added. This form of synthetic vitamin A has been linked to prostate cancer because it reacts with zinc and protein to form an unabsorbable complex. Prostate cancer has also been linked to the inclusion of bovine somatotropin hormone in certain dairy products.

There are also some links between prostate cancer and medications, medical procedures, and medical conditions. Daily use of anti-inflammatory medicines such as aspirin, ibuprofen, or naproxen may decrease prostate cancer risk. Use of the cholesterol-lowering drugs known as the statins may also decrease prostate cancer risk. Infection or inflammation of the prostate (prostatitis) may increase the chance for prostate cancer, and infection with the sexually transmitted infections *chlamydia*, gonorrhea, or syphilis seems to increase risk. Obesity and elevated blood levels of testosterone may increase the risk for prostate cancer.

Prostate cancer is classified as an adenocarcinoma, or glandular cancer, that begins when normal semen-secreting prostate gland cells mutate into cancer cells. The region of prostate gland where the adenocarcinoma is most common is the peripheral zone. Initially, small clumps of cancer cells remain confined to otherwise normal prostate glands, a condition known as carcinoma in situ or prostatic intraepithelial neoplasia (PIN). Although there is no proof that PIN is a cancer precursor, it is closely associated with cancer. Over time these cancer cells begin to multiply and spread to the surrounding prostate tissue (the stroma) forming a tumor. Eventually, the tumor may grow large enough to invade nearby organs such as the seminal vesicles or the rectum, or the tumor cells may develop the ability to travel in the bloodstream and lymphatic system. Prostate cancer is considered a malignant tumor because it is a mass of cells which can invade other parts of the body. This invasion of other organs is called metastasis. Prostate cancer most commonly metastasizes to the bones, lymph nodes, rectum, and bladder.

In prostate cancer, the regular glands of the normal prostate are replaced by irregular glands and clumps of cells. When a man has symptoms of prostate cancer, or a screening test indicates an increased risk for cancer, more invasive evaluation is offered. The only test which can fully confirm the diagnosis of prostate cancer is a biopsy, the removal of small pieces of the prostate for microscopic examination. However, prior to a biopsy, several other tools may be used to gather more information about the prostate and the urinary tract. Cystoscopy shows the urinary tract from inside the bladder, using a thin, flexible camera tube inserted down the urethra. Transrectal ultrasonography creates a picture of the prostate using sound waves from a probe in the rectum.

After biopsy, the tissue samples are then examined under a microscope to determine whether cancer cells are present, and to evaluate the microscopic features (or Gleason score) of any cancer found. In addition, tissue samples may be stained for the presence of PSA and other tumor markers in order to determine the origin of malignant cells that have metastasized. A number of other potential approaches for diagnosis of prostate cancer are ongoing such as early prostate cancer antigen-2 (EPCA-2), and prostasome analysis.

In addition to therapy using the compounds according to the present invention, therapy (including prophylactic therapy) for prostate cancer supports roles in reducing prostate cancer for dietary selenium, vitamin E, lycopene, soy foods, vitamin D, green tea, omega-3 fatty acids and phytoestrogens. The selective estrogen receptor modulator drug toremifene has shown promise in early trials. Two medications which block the conversion of testosterone to dihydrotestosterone (and reduce the tendency toward cell growth), finasteride and dutasteride, are shown to be useful. The phytochemicals indole-3-carbinol and diindolylmethane, found in cruciferous vegetables (califlower and broccholi), have favorable antiandrogenic and immune modulating properties. Prostate cancer risk is decreased in a vegetarian diet.

Treatment for prostate cancer may involve active surveillance, surgery (prostatecomy or orchiectomy), radiation therapy including brachytherapy (prostate brachytherapy) and external beam radiation as well as hormonal therapy. There are several forms of hormonal therapy which include the following, each of which may be combined with or used in combination with compounds and/or compositions according to the present invention.

Antiandrogens such as flutamide, bicalutamide, nilutamide, and cyproterone acetate which directly block the actions of testosterone and DHT within prostate cancer cells.

Medications such as ketoconazole and aminoglutethimide which block the production of adrenal androgens such as DHEA. These medications are generally used only in combination with other methods that can block the 95% of androgens made by the testicles. These combined methods are called total androgen blockade (TAB), which can also be achieved using antiandrogens.

GnRH modulators, including agonists and antagonists. GnRH antagonists suppress the production of LH directly, while GnRH agonists suppress LH through the process of downregulation after an initial stimulation effect. Abarelix is an example of a GnRH antagonist, while the GnRH agonists include leuprolide, goserelin, triptorelin, and buserelin.

The use of abiraterone acetate can be used to reduce PSA levels and tumor sizes in aggressive end-stage prostate cancer for as high as 70% of patients. Sorafenib may also be used to treat metastatic prostate cancer.

Each treatment described above has disadvantages which limit its use in certain circumstances. GnRH agonists eventually cause the same side effects as orchiectomy but may cause worse symptoms at the beginning of treatment. When GnRH agonists are first used, testosterone surges can lead to increased bone pain from metastatic cancer, so antiandrogens or abarelix are often added to blunt these side effects. Estrogens are not commonly used because they increase the risk for cardiovascular disease and blood clots. The antiandrogens do not generally cause impotence and usually cause less loss of bone and muscle mass. Ketoconazole can cause liver damage with prolonged use, and aminoglutethimide can cause skin rashes.

Palliative care for advanced stage prostate cancer focuses on extending life and relieving the symptoms of metastatic disease. As noted above, abiraterone acetate shows some promise in treating advance stage prostate cancer as does sorafenib. Chemotherapy may be offered to slow disease progression and postpone symptoms. The most commonly used regimen combines the chemotherapeutic drug docetaxel with a corticosteroid such as prednisone. Bisphosphonates such as zoledronic acid have been shown to delay skeletal complications such as fractures or the need for radiation therapy in patients with hormone-refractory metastatic prostate cancer. Alpharadin may be used to target bone metastasis. The phase II testing shows prolonged patient survival times, reduced pain and improved quality of life.

Bone pain due to metastatic disease is treated with opioid pain relievers such as morphine and oxycodone. External beam radiation therapy directed at bone metastases may provide pain relief. Injections of certain radioisotopes, such as strontium-89, phosphorus-32, or samarium-153, also target bone metastases and may help relieve pain.

As an alternative to active surveillance or definitive treatments, alternative therapies may also be used for the management of prostate cancer. PSA has been shown to be lowered in men with apparent localized prostate cancer using a vegan diet (fish allowed), regular exercise, and stress reduction. Many other single agents have been shown to reduce PSA, slow PSA doubling times, or have similar effects on secondary markers in men with localized cancer in short term trials, such as pomegranate juice or genistein, an isoflavone found in various legumes.

Manifestations or secondary conditions or effects of metastatic and advanced prostate cancer may include anemia, bone marrow suppression, weight loss, pathologic fractures, spinal cord compression, pain, hematuria, ureteral and/or bladder outlet obstruction, urinary retention, chronic renal failure, urinary incontinence, and symptoms related to bony or soft-tissue metastases, among others.

Additional prostate drugs which can be used in combination with the compounds and/or compositions according to the present invention include, for example, the enlarged prostate drugs/agents, as well as eulexin, flutamide, goserelin, leuprolide, lupron, nilandron, nilutamide, zoladex and mixtures thereof. Enlarged prostate drugs/agents as above, include for example, ambenyl, ambophen, amgenal, atrosept, bromanyl, bromodiphenhydramine-codeine, bromotuss-codeine, cardura, chlorpheniramnine-hydrocodone, ciclopirox, clotrirnazole-betamethasone, dolsed, dutasteride, finasteride, flomax, gecil, hexalol, lamisil, lanased, loprox, lotrisone, methenamine, methen-bella-meth B1-phen sal, meth-hyos-atrp-M blue-BA-phsal, IHP-A, mybanil, prosed/DS, Ro-Sed, S-T Forte, tansulosin, terbinafine, trac, tussionex, ty-methate, uramine, uratin, uretron, uridon, uro-ves, urstat, usept and mixtures thereof.

The present invention relates to herbal compositions and/or herb extract compositions, especially including solid extracts or extracts which are based preferably at least in part on aqueous, or $C_1$-$C_3$ alcoholic (preferably ethanolic) solvents of herbs selected from the group consisting of *Aloe barbadensis* (蘆薈:F3), *Rheum palmatum* L. (大黃:B6, *Stephania tetrandra* (汉防己:C4), *Phellodendron chinense* Schneid. (黃柏:D8), *Euphorbia humifusa* (地錦草:S6), *Eclipta prostrata* (墨旱蓮:I2), *A. venetum* L. (羅布麻:F1), *Portulaca oleracea* L. (馬齒莧:F5), and *Sanguisorba officinalis* L. (地榆:E5), *Camellia sinensis* var. *assamica* (Mast.) Kitamura (普洱:PE), *Punica granatum*. (石榴:PG) and mixtures thereof. Further aspects of the invention relate to compositions which comprise an effective amount of an herb extract in liquid, semi-solid or solid form, optionally in combination with a pharmaceutically acceptable carrier, additive or excipient. These compositions may be used to prevent, treat, ameliorate, or reduce the incidence of various disease states or conditions which arise from androgen receptor (AR) hyperactivity, comprising administering an effective amount of an extract as otherwise described herein to a patient in need thereof. Disease states or conditions which may be treated include, for example, prostate hyperplasia, prostate cancer, including castration resistant prostate cancer, drug resistant prostate cancer, especially including drug resistant cancers associated with AR-Vs (androgen receptor splice variants), bicalutamide and/or enzalutamide resistant prostate cancer, hepatocellular cancer, hair loss and/or the growth of hair, especially in the scalp and in other regions of the body where hair growth is desirable, pattern hair loss (androgenetic alopecia) caused by high level of DHT, acne, seborrhea, hirsutism (excessive body hair), hidradenitis suppurativa, paraphilias, precocious puberty in boys and polycystic ovary syndrome in women, among others.

Pharmaceutical compositions according to the present invention comprise an effective amount of one or more compounds according to the present invention optionally in combination with a pharmaceutically acceptable additive, carrier or excipient.

In another aspect, the present invention is directed to the use of one or more herbal extracts according to the present invention in a pharmaceutically acceptable carrier, additive or excipient at a suitable dose ranging from about 0.05 to about 100 mg/kg of body weight per day, preferably within the range of about 0.1 to 50 mg/kg/day, most preferably in the range of 1 to 20 mg/kg/day. The desired dose may conveniently be presented in a single dose or as divided doses administered at appropriate intervals, for example as two, three, four or more sub-doses per day.

Ideally, the active ingredient should be administered to achieve effective peak plasma concentrations of the active compound preferably within the range of from about 0.05 to about 5 uM. This may be achieved, for example, by oral or other route of administration administration as otherwise described herein. Oral dosages, where applicable, will depend on the bioavailability of the compounds from the GI tract, as well as the pharmacokinetics of the compounds to be administered. While it is possible that, for use in therapy, a compound of the invention may be administered as the raw chemical, it is preferable to present the active ingredient as a pharmaceutical formulation, presented in combination with a pharmaceutically acceptable carrier, excipient or additive.

Pharmaceutical formulations include those suitable for oral, rectal, nasal, topical (including buccal and sub-lingual), or parenteral (including intramuscular, sub-cutaneous and intravenous) administration. Compositions according to the present invention may also be presented as a bolus, electuary or paste. Tablets and capsules for oral administration may contain conventional excipients such as binding agents, fillers, lubricants, disintegrants, or wetting agents. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils), or preservatives. When desired, the above described formulations may be adapted to provide sustained release characteristics of the active ingredient(s) in the composition using standard methods well-known in the art.

In the pharmaceutical aspect according to the present invention, the compound(s) according to the present invention is formulated preferably in admixture with a pharmaceutically acceptable carrier. In general, it is preferable to administer the pharmaceutical composition orally, but certain formulations may be preferably administered parenterally and in particular, in intravenous or intramuscular dosage form, as well as via other parenteral routes, such as transdermal, buccal, subcutaneous, suppository or other route, including via inhalation, including intranasally. Oral dosage forms are preferably administered in tablet or capsule (preferably, hard or soft gelatin) form or as solutions and/or suspensions. Intravenous and intramuscular formulations are preferably administered in sterile saline. Of course, one of ordinary skill in the art may modify the formulations within the teachings of the specification to provide numerous formulations for a particular route of administration without rendering the compositions of the present invention unstable or compromising their therapeutic activity.

In particular, the modification of the present compounds to render them more soluble in water or other vehicle, for example, may be easily accomplished by minor modifications (such as salt formulation, etc.) which are well within the ordinary skill in the art. It is also well within the routineer's skill to modify the route of administration and dosage regimen of a particular compound or composition in order to manage the pharmacokinetics of the present compounds for maximum beneficial effect to the patient.

Formulations containing the compounds of the invention may take the form of solid, semi-solid, lyophilized powder, or liquid dosage forms, such as, for example, tablets, capsules, powders, sustained-release formulations, solutions, suspensions, emulsions, suppositories, creams, ointments, lotions, aerosols or the like, preferably in unit dosage forms suitable for simple administration of precise dosages.

The compositions typically include a conventional pharmaceutical carrier, additive or excipient and may additionally include other medicinal agents, carriers, and the like. Preferably, the composition will be about 0.05% to about 75-80% by weight of an extract or extracts of the invention, with the remainder consisting of suitable pharmaceutical additives, carriers and/or excipients. For oral administration, such excipients include pharmaceutical grades of mannitol, lactose, starch, magnesium stearate, sodium saccharine, talcum, cellulose, glucose, gelatin, sucrose, magnesium carbonate, and the like. If desired, the composition may also contain minor amounts of non-toxic auxiliary substances such as wetting agents, emulsifying agents, or buffers.

Liquid compositions can be prepared by dissolving or dispersing the extracts in liquid, semi-solid or solid form (often about 0.5% to about 20%), and optional pharmaceutical additives, in a carrier, such as, for example, aqueous saline, aqueous dextrose, glycerol, or ethanol, to form a solution or suspension. For use in oral liquid preparation, the composition may be prepared as a solution, suspension, emulsion, or syrup, being supplied either in liquid form or a dried form suitable for hydration in water or normal saline.

When the composition is employed in the form of solid preparations for oral administration, the preparations may be tablets, granules, powders, capsules or the like. In a tablet formulation, the composition is typically formulated with additives, e.g. an excipient such as a saccharide or cellulose preparation, a binder such as starch paste or methyl cellulose, a filler, a disintegrator, and other additives typically used in the manufacture of medical preparations.

An injectable composition for parenteral administration will typically contain the compound in a suitable i.v. solution, such as sterile physiological salt solution. The composition may also be formulated as a suspension in a lipid or phospholipid, in a liposomal suspension, or in an aqueous emulsion.

The pharmaceutical compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Methods for preparing such dosage forms are known or will be apparent to those skilled in the art; for example, see "Remington's Pharmaceutical Sciences" (17th Ed., Mack Pub. Co, 1985). The person of ordinary skill will take advantage of favorable pharmacokinetic parameters of the pro-drug forms of the present invention, where applicable, in delivering the present compounds to a patient suffering from a viral infection to maximize the intended effect of the compound.

The pharmaceutical compositions according to the invention may also contain other active ingredients in the treatment of any one or more of the disease states or conditions which are treated with herbal extracts according to the present invention. Effective amounts or concentrations of each of the active compounds of these herbal extracts may be included within the pharmaceutical compositions according to the present invention.

The individual components of such combinations may be administered either sequentially or simultaneously in separate or combined pharmaceutical formulations. These include especially, for example, one or more of aloe-emodin, emodin, chrysophanol, rhein, sennoside-A, sennoside-C, sennoside-D, gallic acid, epigallocatechin (EGC) gallocatechin (GC), quercetin, keampferol, epigallocatechin gallate (EPCG) and mixtures thereof.

When one or more of the compounds according to the present invention is used in combination with a second therapeutic agent active the dose of each compound may be either the same as or differ from that when the compound is used alone. Appropriate doses will be readily appreciated by those skilled in the art.

In method aspects according to the present invention, one or more pharmaceutical compositions according to the present invention may be administered to a patient in the treatment or prevention of any disease state or condition previously mentioned. An effective amount of an herbal extract as otherwise described herein is administered to a patient exhibiting symptoms of a disease state or condition as otherwise described herein in order to treat the symptoms of the disease states and/or conditions and reduce or eliminate the likelihood that the disease state or condition will deteriorate.

Pharmaceutical compositions according to the present invention comprise an effective amount of one or more of the extracts in liquid, semi-liquid or solid form, otherwise described herein, optionally in combination with a pharmaceutically acceptable carrier, additive or excipient, and further optionally in combination with at least one additional agent useful in treating a disease state or condition which is related to or modulated through androgen receptor (AR) protein. In this aspect of the invention, multiple compounds may be advantageously formulated to be coadministered for the prophylactic and/or therapeutic treatment of any one or more of the disease states or conditions described hereinabove.

The individual components of such combinations as described above may be administered either sequentially or simultaneously in separate or combined pharmaceutical formulations. When one or more of the extracts according to the present invention is used in combination with a second therapeutic agent active the dose of each may be either the same as or differ from that when the compound is used alone. Appropriate doses will be readily appreciated by those skilled in the art.

General Method

Eleven (11) herbs, including *Aloe barbadensis* (*Aloe Vera*) (蘆薈:F3), *Rheum palmatum* L. (大黃:B6), *Stephania tetrandra* (汉防己:C4), *Phellodendron chinense* Schneid. (黃柏:D8), *Euphorbia humifusa* (地錦草:S6), *Eclipta prostrata* (墨旱蓮:I2), *A. venetum* L. (羅布麻:F1) 羅布麻*Portulaca oleracea* L. (马齿苋:F5), *Sanguisorba officinalis* L. (地榆:E5), (*Camelia sinensis* var. *assamica* (Mast.) Kitamura (普洱:PE) and *Punica granatum*. (石榴:PG) were found to have inhibitory effect on androgen receptor and could be used for the prevention or treatment of prostate hyperplasia or prostate cancer as well as diseases caused by hyperactivity of androgen receptor.

These 11 herbs, either individually or in any combination could be used for the treatment of both AR-positive and AR-negative prostate cancers as well as other type of cancers.

Among the eleven (11) herbs, Aloe-emodin of *Aloe barbadensis* and gallic acid of *Euphorbia humifusa* were found to play key role in inhibiting androgen receptor activity. Herbs or herbal formulations contain aloe-emodin and gallic acid (Table 3, below) will have potential for the prevention or treatment of prostate hyperplasia or prostate cancer as well as diseases caused by over activity of androgen receptor. In addition to aloe-emodin and gallic acid, epigallocatechin (EGC), gallocatechin (GC), quercetin, keampferol, epigallocatechin gallate (EGCG) or the polyphenol fraction of *Camellia assamica* also exhibit inhibitory effect on androgen receptor activity and each alone or in any combination may be used to reduce the likelihood, inhibit and/or treat prostate hyperplasia, prostate cancer or other diseases caused by over activity of androgen receptor.

TABLE 3

List of gallic acid containing herbs.

| Chinese name | English name |
|---|---|
| 大叶桉 | *Eucalyptus robusta* Sm. |
| 山茱萸 | *Comusofficinalis* Sieb. et Zucc. |
| 千屈菜 | *Lythrumsalicaria* L. |
| 马桑 | *Coriaria sinica* Maxim. |
| 化香树 | *Platycarya strobilacea* Sieb. et Zucc. |
| 乌桕 | *Sapium sebiferum* (L)Roxb. |
| 石榴 | *Punica granatum* L. |
| 阿拉伯相思树 | *Acaciagrabica* Willd. |
| 西西里漆树 | *Rhus coriaria* Linn. |
| 月季 | *Rosa chinensis* Jacq. |
| 普洱茶 | puer tea |
| 五倍子 | *Galla Chinensis* |
| 景天三七 | *Stedum Aizoom* L. |
| 茶条槭(叶) | amur maple |
| 余甘子 | *Phyllanthus emblica* L. |
| 当归 | *Angelica sinensis* |
| 赤芍药 | *Paeonia lactiflora* Pall. P.veitchii Lynch |
| 甜草 | *Oldenlandia cantonensis* How |
| 葡萄籽 | grape seed |
| 枇杷 | *Loquat* |
| 白芍 | *Paeortialactiflora* |
| 猴耳环 | *Pithecellobium clypearia* Benth. |
| 黄海棠 | *hypericum ascyron* |
| 诃子 | *Fructus Chebulae* |
| 盘龙七 | tsingling bergenia rhizome |
| 菱角壳 | hull of water chestnut |
| 柞树皮 | *Quercus mongolicus* |
| 草原老鹳草 | *Geranium wilfordii* Maxim |
| 矮地茶 | *Herba Ardisiae Japorticae* |
| 番石榴叶 | guava leaf |
| 虎耳草 | *Saxifrage* |
| 广枣 | *Choerospondias axillaris* |
| 青龙衣 | *Qinglongyi* |
| 核桃楸叶 | *Juglans mandshwrica* leaves |
| 刺玫果 | Wild Rose Hip |
| 白蔹 | *ampelopsis japonica* |
| 芡实 | *Euryale ferox* Salisb. |
| 宽叶重楼 | broadleaf paris |
| 绿玉树 | *Euphorbia tirucalli* L. |
| 艾叶 | chinese mugwort leaf |
| 拳参 | *Polygonum bistorta* L. |
| 绿茶 | green tea |
| 地榆 | Garden Burnet |
| 头花蓼 | *Polygonum capitatum* |
| 叶下珠 | *Phyllaothus urinarla* L. |
| 菱角 | *Trapa manshurica* |
| 地棯 | *Melastoma dodecandrum lour.* |
| 柿蒂 | *Calyx kaki* |
| 地锦草 | *Humifuse Euphorbia* |
| 青果 | *Canarium album* Raeusch. |

TABLE 3-continued

List of gallic acid containing herbs.

| Chinese name | English name |
|---|---|
| 紫地榆 | *Geranium strictipe* |
| 老鹳草 | *Geranium carolinianum* L. |
| 红景天 | Red Common Stonecrop Herb |
| 铁苋菜 | Copperleaf |
| 倍花 | Chinese *gall Beihua* |
| 红绒毛羊蹄甲 | *Bauhinia aurea* |

Epigallocatechin, gallocatechin, quercetin and keampferol of F1 showed inhibition on DHT induced androgen receptor activity of 22Rv1 cells. These chemicals could be used for the prevention or treatment of prostate hyperplasia or prostate cancer as well as diseases caused by over activity of androgen receptor.

Results

Figure 2:
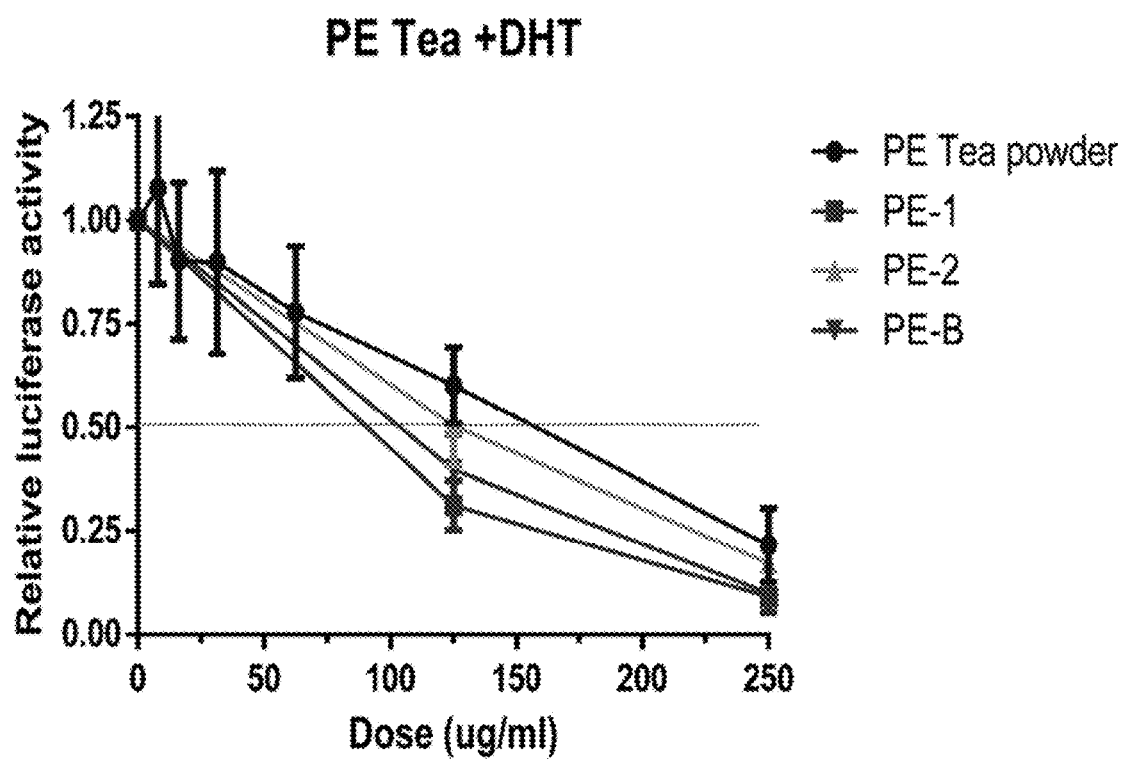
FIG. 2 shows the effect of different batches of PE tea (puer tea) water on the androgen receptor mediated transcription activity of 22RV1 AR-luciferase reporter cells in condition with DHT.

Based on a comprehensive database (STAR) evolved from our own research—studying the effects of herbal water extracts from over 250 formulations, across 25 signaling pathways, using primary luciferase reporter assay and other enzymatic reactions. The inventors selected 9 herbs: *Aloe vera* (芦荟:F3), *Rheum palmatum* L. (大黄:B6), *Stephania tetrandra*(汉防己:C4), *Phellodendron chinense* Schneid. (黄柏:D8), *Euphorbia humifusa* (地锦草:S6), *Eclipta prostrata* (墨旱莲:I2), *A. venetum* L. (罗布麻:F1) *Portulaca oleracea* L. (马齿苋:F5) *Sanguisorba officinalis* L. (地榆:E5) which shown anti-androgen receptor (AR) activity in the luciferase receptor assay (FIG. 1). In addition, *Camellia assamica* (Mast) Chang (puer tea, 普洱茶:PE) and *Punica granatum* (石榴:PG, pomegranate) were shown to have inhibitory activity on androgen receptor mediated transcription activity of 22RV1 AR-luciferase reporter cells in condition with DHT (FIGS. 2 and 31). To further validate their effect on androgen receptor target genes (PSA, KLK2) mRNA expression. All these herbs could inhibit DHT induced PSA and KLK2 mRNA expression (FIGS. 3 and 31).

Different herbs may have different mechanism of actions against AR signaling. F3 and F5 could down regulate both AR protein and mRNA (FIGS. 4 and 5). B6, C4 and DS could only down regulate AR protein but had weak effect on AR mRNA (FIGS. 4 and 5). S6, I2, F1, E5 and PE had no effect on AR protein and mRNA (FIGS. 4 and 5) and they may directly act on the AR.

A DNA pull down assay was used to access if herbal water can inhibit the interaction between Androgen receptor and DNA. Androgen receptor-DNA interaction pull down assay was performed by mixing biotin label DNA 5'-gtaat-tgcAGAACAgcaAGTGCTagctctc-3' (SEQ ID NO: 1) (with androgen binding site) and nuclear lysis with androgen receptor protein (extracted from 22RV1 cells pre-stimulated with DHT 25 nM for overnight). Streptavidin-Dynabead was used to trap down the DNA-AR complex under magnetic condition. Western blotting was used to detect the amount of pull down AR protein. Inhibition between DNA and androgen receptor binding will reduce the amount of AR protein pull down. As shown in FIG. 6, F3 and C4 did not inhibit DNA-AR protein interaction while F1, S6, E5, F5, I2, PE1 could inhibit DNA-AR protein interaction with different potency. Possible mechanism actions of these herbs are listed on table 1.

9 herbs showed cytotoxic effect on two prostate cancer cells: 1 22RV1 cells which express expresses the full-length AR and the constitutively active, truncated AR, which is responsible for bicalutamide and enzalutamide resistance. 22RV1 cell growth is partially dependent on androgen and its growth can be reduced by down regulating both AR isoforms. 2. Du145 cells which do not express AR protein, and its growth is androgen independent. As shown in Table 2, F3, B6, C4, S6, I2, F1, show stronger effect on inhibiting the growth of 22RV1 cells than Du145 cells. These herbs may have advantage for targeting prostate cancer cells with AR protein expression. However, D8 and E5 were more toxic towards Du145 cells than 22RV1 This suggests that D8 and E5 may have other target sites, which is independent on AR, for inhibiting the growth of Du145. Overall, all these herbs may have potential for treatment of prostate cancer with or without expressing AR protein.

Figure 7:
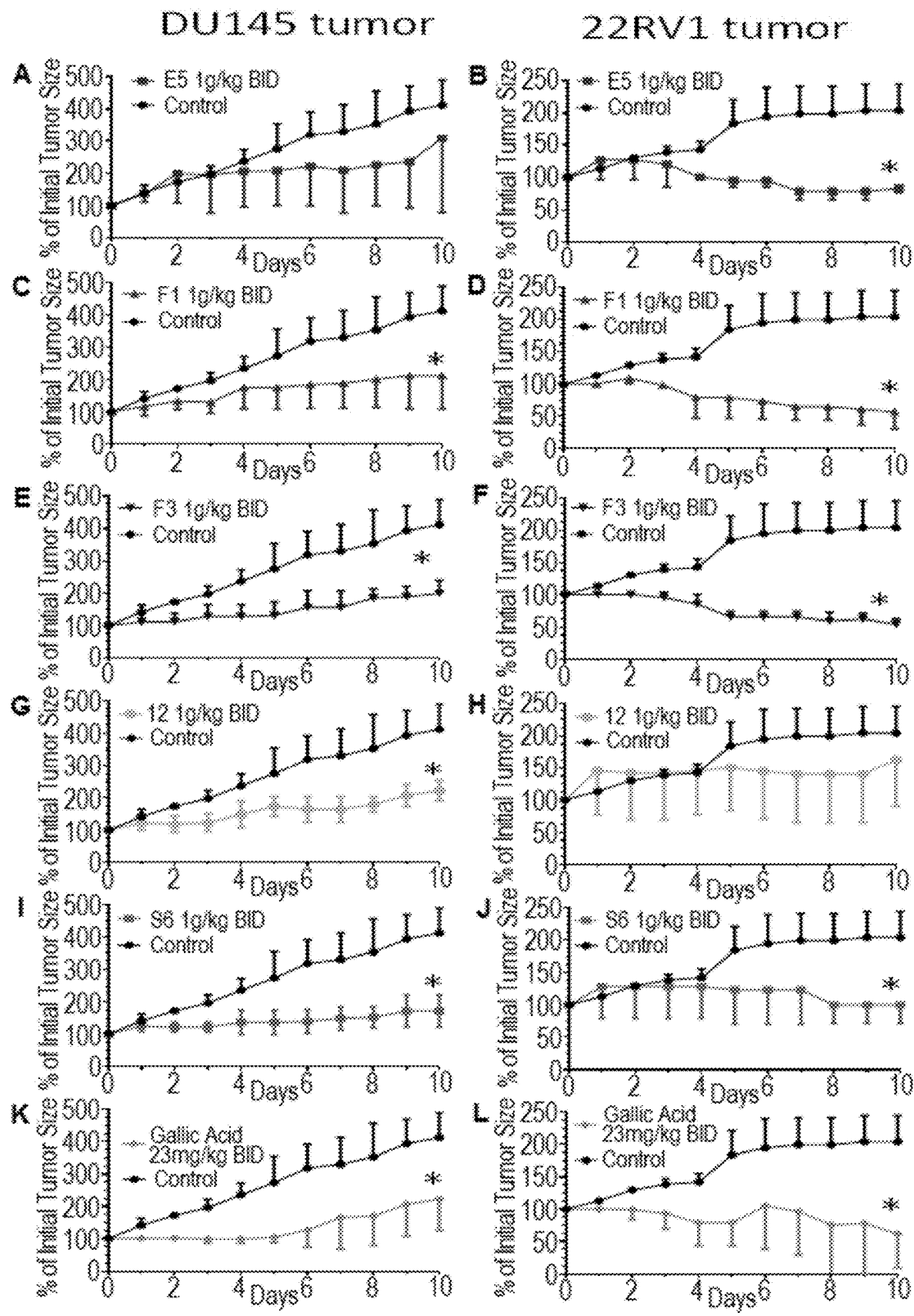

As shown in FIG. 7, water extract of E5 (1 g/kg BID), F1 (1 g/kg BID), F3 (1 g/kg BID), I2 (1 g/kg BID), S6 (1 g/kg BID) and Gallic acid (23 mg/kg BID; equivalent dose to S6 1 g/kg BID) were feed orally to mouse implanted with 22RV (AR-ve) and DU145 (AR-ve) xenografts. F1, F3, I2, S6 showed significant inhibition on the DU145 tumor growth while E5, F1, F3, S6, showed significant inhibition on the 22RV1 tumor growth (FIG. 7). E5 may have higher selectively to inhibit prostate cancer with AR protein in vivo. I2 may have higher selectively to inhibit prostate cancer without AR protein expression in vivo.

Figure 8:
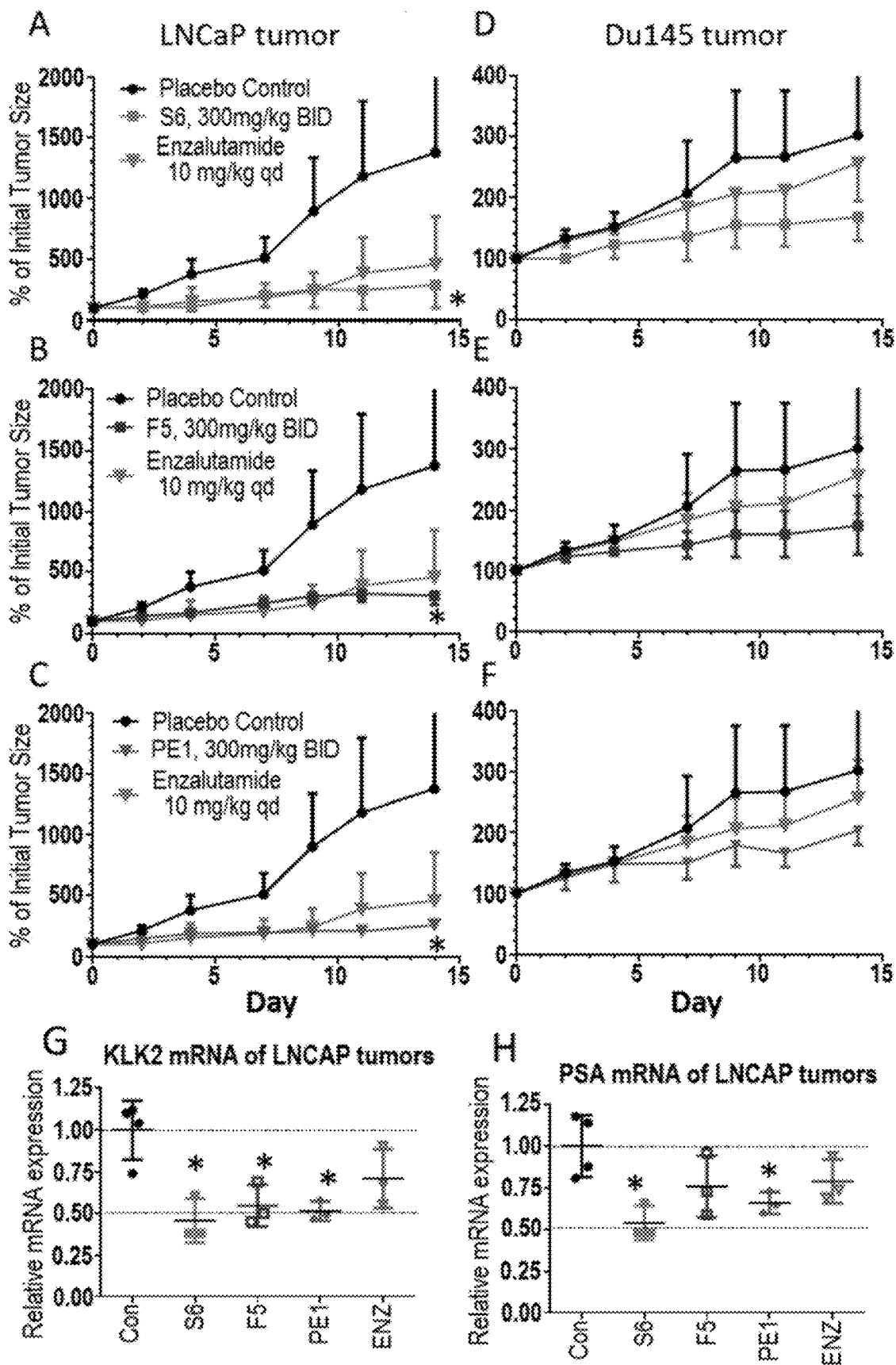

In another animal experiment, we compared the anti-prostate tumor growth effect of S6, F5, and PE1 (each 300 mg/kg bid) to enzalutamide (10 mg/kg qd) (targeting on AR) on LNCaP (androgen dependent) xenograft tumor and Du145 xenograft tumor in nude mice for two weeks. As predicted that enzalutamide effectively inhibited the growth of LNCaP tumors but not Du145 tumors (FIG. 8 A-F). S6, F5 and PE1 showed significant inhibition on the growth of LNCaP (P<0.05) but S6, F5 and PE1 have no significant inhibition on the growth of Du145 tumors (FIG. 8A-F). qRT-PCR results further supported that S6, F5, PE1 could down regulate the AR target genes, KLK2 or PSA of LNCaP tumor (FIG. 8G, 8H). In conclusion, S6, F5, PE1 appears to have selectivity on inhibiting the growth of androgen dependent tumor thought targeting AR.

Further experiments were conducted pursuant to the present invention. The results of these experiments are presented in FIGS. 20-30 and described herein.

As shown in FIG. 20, preparative HPLC was conducted to fractionalize S6 water extract. To that end, 10 ul of S6 water extract was subjected to HPLC with a C18 preparative column running with an increasing gradient of acetonitrile. Fraction 9 (star) from the preparative HPLC fractions evidenced the strongest anti-androgen receptor activity in AR luciferase report assay. Fraction 9 was collected and then subjected to LC-MS analysis using negative mode scanning from MW160 to MW800. Fraction 9 (red) contained gallic acid (MW170). The small insert panel depicted in FIG. 21 evidenced that pure gallic acid was active (IC50 was about 28 uM) against AR activity of 22RV1 cells in the luciferase report assay.

Several tea extracts were tested for cytotoxicity against 22RV1 and Du145 cells. The results are presented in FIG. 22. In particular, the cytotoxicity of each of F1 (*Apocynum venetum*) and the teas labelled as Chinese "Luo-bu-ma" (LBM tea) (which is sometimes *Apocynum venetum* or "*Apocynum pictum*" in China) and LBM mix tea which contains the leaf, flower and green tea was tested. All of these teas exhibited cytotoxicity on 22RV1 cells and Du145 cells (which don't express androgen receptor) as shown. F1 showed stronger cytotoxicity than LBM tea or LBM mix tea. Methylene blue was used to stain the total cells following 3-day treatment with the water extracts.

FIG. 23 shows a comparison of polyphenol extracts (PE). PE-powder from Yunnan taslydee pure biological tea group co.ltd. or PE-1, PE-2, PE-B from Gaoligongshan Co. Ltd was tested for their anti-androgen receptor activity using 22RV1 luciferase reporter cell assay. The results are shown in FIG. 23, with all extracts exhibiting activity and PE-1 exhibiting the strongest activity.

A preparative HPLC was conducted to fractionalize a further PE1 water extract. 1 ml of S6 (100 mg/ml) was subjected to HPLC using a C18 preparative column running with an increasing gradient of acetonitrile. Fractions 13, 21, 32 (star) from the preparative HPLC fractions had relative stronger anti-androgen receptor activity in AR luciferase report assay. These fractions were subjected to further analysis. This is show in FIG. 24. HPLC analysis of fraction 13 (red) of PE1 from preparative HPLC and PE1 crude water extract (FIG. 25) showed that 5-Galloylquinic acid could be found in identifiable quantities in fraction 13, evidencing that this compound was most likely responsible for the activity exhibited by the fraction. HPLC analysis for fraction 21 (red) of PE1 from the preparative HPLC of PE1 crude water extract showed that 1-Galloyl-beta-glucose could be found in identifiable quantities in fraction 21 and was likely responsible for the activity of fraction 21. See FIG. 26. HPLC analysis of fraction 31 (red) of the PE1 water extract from the preparative HPLC evidenced identifiable quantities of epigallocatechin (EGC) as the likely active component. This is shown in FIG. 27. HPLC analysis of fraction 33 (red) of PE1 from the preparative HPLC also evidenced identifiable quantities of EGC as the likely active component. This is show in FIG. 28. HPLC analysis of fraction 43 (red) and 44 (green) of PE1 extract from preparative HPLC showed that fraction 43 had identifiable quantities of EGC and fraction 44 had identifiable quantities of epigallocatechin gallate (EGCG). Results indicated that fraction 44 contained EGCG in identifiable quantities. The fraction also appeared to contain kaempferol-3-O—R-L-rhamnopyranosyl (1f6)-β-D-galactopyranoside, quercetin-3-O-β-D-glucopyranoside or gallic acid-3-O-(60-O-galloyl)-β-D-glucoside in appreciable quantities. This is indicated in FIG. 29.

Various extracts according to the present invention were tested for cytotoxicity of different on different cancer cell lines, for example, 22RV1, HepG2, KB, KB-MDR (multi-drug resistant), KB-300(CPT1 resistant) as indicated in FIG. 30. The average $IC_{50}$ from three independent experiments is presented in the figure. A methylene blue assay was used to determine the cell growth following the treatment of different herb water extracts for 3 days.

Potential Active Chemical(s)

*Aloe barbadensis* (F3):

Preparative HPLC was used to fractionize water extract of F3. As shown in FIGS. 9A and 9B, fraction 31 and 32 showed similar inhibitory effect on AR action. LC-MS result indicated that fraction 31 and 32 contained similar amount of Aloe-emodin MW271 and compound with MW686.1 which could be Elgonica-dimer. Standard Aloe-emodin was purchased and was confirmed to have anti-AR activity using luciferase reporter assay (FIG. 10). The equivalent amount of aloe-emodin was compared to crude water extract of F3 using luciferase report assay (FIG. 10, insert figure). Result indicated that aloe-emodin is key ingredient of F3 for inhibiting AR activity. However, Aloe-emodin are relative weaker than the whole herbal mixture of F3. This suggests that other chemicals in F3 may be also active against AR.

Different similar structure to aloe-emodin were selected to tested for their inhibitory effect on AR using luciferase reporter assay. Result indicated that in addition to aloe-emodin, emodin and sennoside A, but no chrysophanol, sennoside C or sennoside D, also activity in against AR (FIG. 11)

*Euphorbia humifusa* (S6):

Solid phase extraction column was used to fractionate S6 water extract. Water and 10% ethanol elution had relative stronger inhibitory effect on AR using luciferase reporter assay (FIG. 12 insert). LC-MS detected gallic acid in water elution and 10% ethanol elution. Equivalent dose of gallic acid (as compare to S6) were shown to have inhibitory effect of androgen receptor mediated transcriptional activity (FIG. 13A). Gallic acid was shown to have inhibitory effect on KLK2 and PSA but no AR (FIG. 1133, 13C, 13D). These result indicated that they are key ingredient of S6 for inhibiting AR activity. However, gallic acid are relative weaker than the whole herbal mixture of S6. This suggests that other chemicals in S6 may be also active against AR or other chemicals may enhance the action of gallic acid against AR. Furthermore, gallic acid exhibit in vivo anti-tumor activity in against the growth of 22RV1 and Du145 tumor in nude mice (FIGS. 13E and 13F).

*A. venetum* L. (羅布麻:F1):FIG. 14, F1 (*Apocynum venetum*) and other tea label with Chinese "Luo-bu-ma:LBM" which could be *Apocynum venetum* or "*Apocynum pictum*" in China were compared for their anti-AR activity using luciferase reporter assay. Some LBM tea may also contain its leaf, its flower and green tea. All these teas had anti-androgen receptor activity, but F1 had higher anti-androgen receptor than the others (3M, LBM mix tea and LBM mix tea-Nile). F1, LBM and LBM tea mix showed inhibition on KLK2 and PSA mRNA expression (FIG. 1413, 14C).

Solid phase extraction C18 column was used to fractionate F1 water extract (FIG. 15A). 10%, 20%, 40% ethanol elution were found to have relative high anti-AR activity using luciferase reporter assay. LC-MS detect Catechin/Epicatechin. Epigallocatechin or gallocatechin, caffiec, Chlorogenic acid, Isoquercetin, Hyperoside, Astragalin, Trifolin, Acetylated hyperoside Or Acetylated Isoquercetin, quercetin, Keampferol in those fractions (FIG. 1513). Epigallocatechin, gallocatechin, quercetin and Keampferol were shown to have different potency on inhibiting AR using luciferase reporter assay (FIG. 15C).

*Camellia assamica* (Mast) Chang (puer tea, 普洱茶:PE) Polyphenols (PP) (extract from PE) obtained from obtained from Gaoligongshan co.ltd showed anti-androgen receptor using 22RV1 luciferase reporter cell assay (FIG. 16A). When PE1 or PP water extract passing though C18 solid phase extraction column, 30% elution (arrow) showed the most potent anti-androgen receptor activity us using 22RV1 luciferase reporter cell assay (FIG. 16B 16C). Since the potency of PE1 and PP is about 5:1, 1 ml of 100 mg/ml PE1 or 1 ml of 20 mg/ml PP were chosen as the input for solide phase extraction. LC_MS showed that 30% ethanol elution of PE1 or PP, some mass peaks (black) showed very similar intensity and some peaks (highlight as green) had different intensity. The common peaks should be more related to the anti-androgen receptor activity (FIG. 17). But we don't exclude if the green highlighted compounds are also active.

Five pure compounds, epicatechin, catechin, gallocatechin (GC), Epigallocatechin (EGC) and epigallocatechin gallate EGCG which exist in F1 were tested for their anti-androgen receptor activity in present of DHT 10 nM using luciferase reporter assay. GC, EGC, EGCG were found to have anti-androgen receptor activity. EGC showed highest potency against AR (FIG. 18). When LC-MS scanning parameter was set to have low molecular weight scan. Gallic acid could be detected in PE (FIG. 19). For PE tea IC50 125 ug/ml contains about 4.8 uM Gallic acid which may partially play a role in inhibiting AR.

*Punica granatum* or common name pomegranate (石榴:PG) extract was found to have inhibitory effect on DHT induced androgen receptor activity of 22RV1 cells (FIG. 31A). PC also inhibited DHT induced KLK2 and PSA mRNA expression of 22RV1 cells (FIGS. 31B and C). PG reduced the basal level of androgen receptor protein and DHT induced androgen receptor protein of 22RV1 cells (FIG. 31D). In addition, PG showed inhibition on AR mRNA expression (FIG. 31E).

a. Novelty and Major Advantages:

1. The 11 herbs including *Aloe barbadensis* (蘆薈:F3), *Rheum palmatum* L. (大黄:B6), *Stephania tetrandra* (汉防己:C4), *Phellodendron chinese* Schneid. (黄柏:D8), *Euphorbia humifusa* (地錦草:S6), *Eclipta prostrata* (墨旱蓮:I2), *A. venetum* L. (羅布麻:F1), *Portulaca oleracea* L. (马齿苋:F5), *Sanguisorba officinalis* L. (地榆:E5), or *Camellia sinensis* var. *assamica* (Mast.) Kitamura (普洱:PE), *Punica granatum* (石榴:PG) and/or extracts of these herbs and/or their active components (which can suppress AR receptor activity, can be used alone or in combination for the prevention or treatment of prostate hyperplasia or prostate cancer as well as diseases caused by hyperactivity of androgen receptor.

2. Herbs or the formulation containing those herbs listed above in combination with other chemicals such as Aloe-emodin, Gallic acid, Epigallocatechin, gallocatechin, epigallocatechin gallate, quercetin and Keampferol which could be useful for targeting disease or symptoms caused by hyperactivity of androgen receptor.

3. Some of those herbs can be developed as high-end food supplements with scientific evidence for prostate cancer prevention. For example, F1 is commonly used as an herbal tea for controlling the blood pressure in China. F5 is commonly used as vegetable in many places including Europe, the middle east, Asia, and Mexico. PE is a tea which commonly be used. These herbs are considered safe to consume.

4. Aloe-emodin, Gallic acid, Epigallocatechin, gallocatechin, epigallocatechin gallate, quercetin and Keampferol containing herbs or vegetable (table 3) could be developed for the prevention or treatment of prostate hyperplasia or prostate cancer as well as diseases caused by overactivity of androgen receptor.

5. Since these herbs can inhibit the growth of 22RV1 cells which resistance to bicalutamide and enzalutamide, these herbs or their active ingredient can be developed to target bicalutamide and enzalutamide resistant prostate cancer.

Experimental Procedures

The goal of this study by the present inventors was to investigate what effects, if any, herbal medicines have on androgen receptor activity, then to delve further to isolate the specific effects these herbs have on the androgen receptor activity and identify active compounds in these herbs responsible for that activity. This was done in three parts, the first of which was an initial dose-response screening of about 250 herbal medicines for androgen receptor activity using luciferase reporter cells (22RV1 cells transfected with PSA promoter luciferase reporter). RT-qPCR for KLK2 and PSA, which are target genes of androgen reporter, was used to confirm the action of those herbal extracts.

Materials and Methods

PSA Luciferase Reporter Cells—

22RV1 prostate cancer cells were used in the screening study. 22RV1 cell lines were stably transfected with PSA promoter-PGL4.2 luciferase reporter. 25 nM) H T was used to induce androgen receptor for 24 h.

Luciferase Screening—

22RV1 androgen reporter cells were treated with herbal extracts at 30, 100, 300, and 1000 µg/ml for 24 h in a 37° C.-CO2 incubator with or without 25 nM DHT which was used androgen receptor activity. Cells were lysed using luciferase lysis buffer after which luciferase buffer with luciferin was added to generate luminescence. Luminescence was recorded using a luminescence microplate reader.

Real Time Quantitative PCR (RT-qPCR) of NR F2 and Downstream Genes—

RNA was extracted from herb treated cells using the Roche High Pure RNA isolation kit. cDNA was then generated from RNA samples using Bio-rad iScript Advanced cDNA synthesis kit for RT-qPCR. qPCR was performed using human NRF2, 101, NQO1 and β-actin primer (as shown in the table below) and iTaq™ Universal SYBR® Green Supermix in CFX PCR machine (Bio-rad). Relative mRNA expression was calculated based on the change of the threshold cycle relative to the internal control, β-actin, using a standard curve generated by purified PCR products.

TABLE 4

Primer Sequences for RT-qPCR

| | | | |
|---|---|---|---|
| Human AR | F1 R1 | CCTGGCTTCCGCAACTTACAC GGACTTGTGCATGCGGTACTCA | (SEQ ID NO: 2) (SEQ ID NO: 3) |
| Human KLK2 | F1 R1 | GGTGGCTGTGTACAGTCATGGAT TGTCTTCAGGCTCAAACAGGTTG | (SEQ ID NO: 4) (SEQ ID NO: 5) |
| Human PSA | F1 R1 | ACCAGAGGAGTTCTTGACCCCAAA CCCCAGAATCACCCGAGCAG | (SEQ ID NO: 6) (SEQ ID NO: 7) |
| Human β-actin | F1 R1 | GCCACGGCTGCTTCCAGCTCC TTGTGCTGGGTGCCAGGGCAGTGA | (SEQ ID NO: 8) (SEQ ID NO: 9) |

Western Blot Protocol—

Total cell lysis was prepared using 2×SDS sample buffer (62.5 mM Tris-HCl, 2% SDS, 10% glycerol, 50 mM DTT, and 0.05% bromphenol blue) and sonicated for 10 s to shear DNA. Cell nuclei were isolated using Tris buffer saline with 0.4% NP40. Cell extracts were then electrophoresed through 10% SDS-polyacrylamide gels and transferred to 0.2 um nitrocellulose membranes (Bio-Rad Laboratories, Hercules, CA) with a Miniprotein II transferring apparatus (Bio-Rad). The membranes were blocked and probed in TBS-T buffer (1×TBS buffer, 0.2% Tween 20) containing 5% non-fat milk. Monoclonal rabbit anti-AR (1:5000), was used to detect androgen receptor (Abcam #133273) and a monoclonal actin antibody diluted 1:2500 (Sigma, St. Louis, MO) was used to detect β-actin as the internal control to confirm equal protein loading. The membranes were then incubated with horseradish peroxidase-conjugated anti-mouse IgG and anti-rabbit IgG (1:5,000; Sigma). Enhanced chemiluminescence reagents (Perkin-Elmer Life Science Products, Boston, MA) were used to visualize the immunoreactive bands and the densities of protein bands were scanned using and analyzed using ImageJ software from the NIH.

Standardized Preparation of Herbal Extracts

An often expressed concern of holistic medicinal treatments is a lack of standardization when preparing herbal reagents for testing. In order to maintain consistency between preparations for direct quantitative comparisons in functional assays, a standard aqueous extraction protocol was designed. Extracts were prepared by heating dried, powdered herbs (0.5 g) in ultra-pure water (10 ml, >15 megaΩ resistance) at 85° C. for 30 minutes. The aqueous fraction was then filter sterilized and stored at 4° C. in the dark until use. Adherence to this standard protocol not only permits accurate quantitative comparisons between herbal extracts, but also affords the opportunity to compare different harvests of the same teas to account for seasonal variations. In addition, after freeze-drying and reconstituting the most active tea, described later, consistent values were obtained in bioactivity screens, suggesting that the active ingredients in this tea are stable and that this method is a reliable method for standardizing teas.

The invention claimed is:

1. A method for treating, inhibiting, preventing, reducing the incidence of, ameliorating or resolving prostate cancer in a patient or subject in need comprising administering to said patient or subject a medicament comprising an effective amount of an extract of *Euphorbia humifusa* (S6) in combination with an effective amount of at least one extract selected from the group consisting of an extract of *Apocynum venetum* L. (F1), an extract of *Aloe barbadensis* (F3), an extract of *Eclipta prostrata* (I2) and an extract of *Camellia sinensis* var. *assamica* (Mast.) Kitamura (PE).

2. The method according to claim 1 wherein said prostate cancer is androgen dependent or androgen independent prostate cancer.

3. The method according to claim 1 wherein said medicament comprises an extract of *Euphorbia humifusa* (S6) and an extract of *Aloe barbadensis* (F3).

4. The method according to claim 1 wherein said medicament comprises an extract of *Euphorbia humifusa* (S6),an extract of *Aloe barbadensis* an extract of *Eclipta prostrata* (I2), an extract of *Apocynum venetum* L. (F1) and an extract of *Camellia sinensis* var. *assamica* (Mast.) Kitamura (PE).

5. The method according to claim 1 wherein said medicament comprises an extract of *Euphorbia humifusa* (S6), an extract of *Aloe barbadensis* (F3), an extract of *Eclipta prostrata* (I2) and an extract of *Camellia sinensis* var. *assamica* (Mast.) Kitamura (PE).

6. The method according to claim 1 wherein said medicament comprises an extract of *Euphorbia humifusa* (S6), an extract of *Aloe barbadensis* (F3), an extract of *Apocynum venetum* L. (F1) and an extract of *Camellia sinensis* var. *assamica* (Mast.) Kitamura (PE).

7. The method according to claim 1 wherein said medicament comprises an extract of *Euphorbia humifusa* (S6), an extract of *Eclipta prostrata* (I2), an extract of *Camellia sinensis* var. *assamica* (Mast.) Kitamura (PE) and an extract of *A. venetum* L. (F1).

8. The method according to claim 1 wherein said medicament comprises an extract of *Euphorbia humifusa* (S6), an extract of *Aloe barbadensis* (F3), an extract of *Eclipta prostrata* (I2) and an extract of *Apocynum venetum* L. (F1).

9. The method according to claim 1 wherein said medicament comprises an extract of *Euphorbia humifusa* (S6) and at least one extract selected from the group consisting of an extract of *Apocynum venetum* L. (F1), an extract of *Eclipta prostrata* (I2) and an extract of *Aloe barbadensis* (F3).

10. The method according to claim 9 wherein said medicament comprises an extract of *Euphorbia humifusa* (S6) and an extract of *Eclipta prostrata* (I2).

11. The method according to claim 9 wherein said medicament comprises an extract of *Euphorbia humifusa* (S6), an extract of *Eclipta prostrata* (I2) and an extract of *Aloe barbadensis* (F3).

12. The method according to claim 9 wherein said medicament comprises an extract of *Euphorbia humifusa* (S6), an extract of *Aloe barbadensis* (F3) and an extract of *A. venetum* L. (F1).

13. The method according to claim 9 wherein said medicament comprises an extract of *Euphorbia humifusa* (S6), an extract of *Eclipta prostrata* (I2), and an extract of *Apocynum venetum* L. (羅布麻F1).

14. The method according to claim 1 wherein said extract(s) is/are prepared by exposing said herb(s) to an effective amount of water or aqueous alcohol.

15. The method according to claim 14 wherein said alcohol is ethanol.

16. The method according to claim 1 wherein said medicament includes at least one additional antiandrogen compound.

17. The method according to claim 1 wherein said medicament includes at least at least one GNRh modulator.

18. The method according to claim 1 wherein said medicament includes at least one agent selected from the group consisting of flutamide, bicalutamide, nilutamide, cyproterone acetate, ketoconazole, aminoglutethimide, abarelix, leuprolide, goserelin, triptorelin, buserelin, abiraterone acetate and sorafenib.

19. The method according to claim 1 wherein said medicament is combined with an additional agent selected from the group consisting of eulexin, flutamide, goserelin, leuprolide, lupron, nilandron, nilutamide, zoladex and mixtures thereof.

20. The method according to claim 1 wherein said medicament is formulated in oral dosage form.

21. The method according to claim 1 wherein said medicament is formulated in topical dosage form.

22. The method according to claim 1 wherein said prostate cancer is drug resistant prostate cancer.

23. The method according to claim 22 wherein said prostate cancer is drug resistant cancer associated with androgen receptor splice variants (AR-VS).

24. The method according to claim 22 wherein said prostate cancer is bicalutamide and/or enzalutamide resistant prostate cancer.

25. The method according to claim 22 wherein said prostate cancer is castration resistant prostate cancer.

\* \* \* \* \*